US009801824B2

(12) United States Patent
Ault et al.

(10) Patent No.: US 9,801,824 B2
(45) Date of Patent: *Oct. 31, 2017

(54) METHOD FOR DELIVERING A PHARMACEUTICAL COMPOSITION TO PATIENT IN NEED THEREOF

(71) Applicants: POZEN INC., Chapel Hill, NC (US); HORIZON PHARMA USA, INC., Deerfield, IL (US)

(72) Inventors: Brian Ault, Wilmington (DE); Everardus Orlemans, Chapel Hill, NC (US); John R. Plachetka, Chapel Hill, NC (US); Mark Sostek, Wilmington, DE (US)

(73) Assignees: Pozen Inc., Chapel Hill, NC (US); Horizon Pharma USA, Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/207,623

(22) Filed: Jul. 12, 2016

(65) Prior Publication Data

US 2017/0071861 A1    Mar. 16, 2017

Related U.S. Application Data

(63) Continuation of application No. 14/980,639, filed on Dec. 28, 2015, now Pat. No. 9,393,208, which is a continuation of application No. 12/553,107, filed on Sep. 3, 2009, now Pat. No. 9,220,698.

(60) Provisional application No. 61/095,584, filed on Sep. 9, 2008.

(51) Int. Cl.
| | |
|---|---|
| *A61K 9/24* | (2006.01) |
| *A61K 9/28* | (2006.01) |
| *A61K 31/192* | (2006.01) |
| *A61K 31/4439* | (2006.01) |
| *A61K 9/00* | (2006.01) |

(52) U.S. Cl.
CPC ........... *A61K 9/209* (2013.01); *A61K 9/0053* (2013.01); *A61K 31/192* (2013.01); *A61K 31/4439* (2013.01)

(58) Field of Classification Search
CPC .............................. A61K 9/209; A61K 9/2806
See application file for complete search history.

(56) References Cited

U.S. PATENT DOCUMENTS

| | | |
|---|---|---|
| 4,198,390 A | 4/1980 | Rider |
| 4,255,431 A | 3/1981 | Junggren et al. |
| 4,344,929 A | 8/1982 | Bonsen et al. |
| 4,508,905 A | 4/1985 | Junggren et al. |
| 4,554,276 A | 11/1985 | LaMattina |
| 4,562,261 A | 12/1985 | Hirata et al. |
| 4,619,934 A | 10/1986 | Sunshine et al. |
| 4,676,984 A | 6/1987 | Wu et al. |
| 4,704,278 A | 11/1987 | Wu et al. |
| 4,726,951 A | 2/1988 | Panoz et al. |
| 4,738,974 A | 4/1988 | Brandstrom |
| 4,757,060 A | 7/1988 | Lukacsko et al. |
| 4,758,579 A | 7/1988 | Kohl et al. |
| 4,766,117 A | 8/1988 | Crawford et al. |
| 4,786,505 A | 11/1988 | Lovgren et al. |
| 4,853,230 A | 8/1989 | Lovgren et al. |
| 4,865,847 A | 9/1989 | Gosswein |
| 4,948,581 A | 8/1990 | Sawayanagi et al. |
| 4,965,065 A | 10/1990 | Lukacsko et al. |
| 5,026,560 A | 6/1991 | Makino et al. |
| 5,035,899 A | 7/1991 | Saeki et al. |
| 5,037,815 A | 8/1991 | Lukacsko et al. |
| 5,043,358 A | 8/1991 | Lukacsko et al. |
| 5,051,262 A | 9/1991 | Panoz et al. |
| 5,093,132 A | 3/1992 | Makino et al. |
| 5,204,118 A | 4/1993 | Goldman et al. |
| 5,260,333 A | 11/1993 | Lukacsko et al. |
| 5,364,616 A | 11/1994 | Singer et al. |
| 5,373,022 A | 12/1994 | Fawzi et al. |
| 5,409,709 A | 4/1995 | Ozawa et al. |
| 5,417,980 A | 5/1995 | Goldman et al. |
| 5,466,436 A | 11/1995 | Stables |
| 5,514,663 A | 5/1996 | Mandel |
| 5,601,843 A | 2/1997 | Gimet |
| 5,631,022 A | 5/1997 | Mandel et al. |
| 5,643,960 A | 7/1997 | Breitner et al. |
| 5,667,802 A | 9/1997 | Grimberg |
| 5,679,376 A | 10/1997 | Stevens et al. |
| 5,686,105 A | 11/1997 | Kelm et al. |
| 5,690,960 A | 11/1997 | Bengtsson et al. |
| 5,702,723 A | 12/1997 | Griffin |
| 5,714,504 A | 2/1998 | Lindberg et al. |
| 5,716,648 A | 2/1998 | Halskov et al. |
| 5,750,531 A | 5/1998 | Lee et al. |
| 5,817,338 A | 10/1998 | Bergstrand et al. |
| 5,817,340 A | 10/1998 | Roche et al. |
| 5,840,737 A | 11/1998 | Phillips |
| 5,872,145 A | 2/1999 | Plachetka |

(Continued)

FOREIGN PATENT DOCUMENTS

| | | |
|---|---|---|
| AU | 2006235929 | 11/2006 |
| CA | 2139653 | 7/2001 |

(Continued)

OTHER PUBLICATIONS

"A 12 month, phase 3, open-label, multi-center study to evaluate the long-term safety of PN 400," ClinicalTrials.gov, Sep. 11, 2007, accessed from <http://clinicaltrials.gov/ct2/show/NCT00527904> on Sep. 6, 2012.

(Continued)

*Primary Examiner* — Gina Justice
(74) *Attorney, Agent, or Firm* — Parker Highlander PLLC

(57) ABSTRACT

The present disclosure is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof.

20 Claims, 9 Drawing Sheets

(56) References Cited

U.S. PATENT DOCUMENTS

| | | |
|---|---|---|
| 5,877,192 A | 3/1999 | Lindberg et al. |
| 5,900,424 A | 5/1999 | Kallstrom et al. |
| 5,955,451 A | 9/1999 | Lichtenberger et al. |
| 6,013,281 A | 1/2000 | Lundberg et al. |
| 6,025,395 A | 2/2000 | Breitner et al. |
| 6,060,499 A | 5/2000 | Plachetka |
| 6,093,734 A | 7/2000 | Garst et al. |
| 6,132,768 A | 10/2000 | Sachs et al. |
| 6,132,771 A | 10/2000 | Depui et al. |
| 6,136,344 A | 10/2000 | Depui et al. |
| 6,160,020 A | 12/2000 | Ohannesian et al. |
| 6,162,816 A | 12/2000 | Bohlin et al. |
| 6,183,776 B1 | 2/2001 | Depui et al. |
| 6,183,779 B1 | 2/2001 | Ouali et al. |
| 6,207,188 B1 | 3/2001 | Gustavsson et al. |
| 6,231,888 B1 | 5/2001 | Lerner et al. |
| 6,287,600 B1 | 9/2001 | Ouali et al. |
| 6,365,184 B1 | 4/2002 | Depui et al. |
| 6,369,085 B1 | 4/2002 | Cotton et al. |
| 6,372,255 B1 | 4/2002 | Saslawski |
| 6,387,410 B1 | 5/2002 | Woolfe |
| 6,395,298 B1 | 5/2002 | Flanagan et al. |
| 6,428,810 B1 | 8/2002 | Bergstrand et al. |
| 6,485,747 B1 | 11/2002 | Flanagan et al. |
| 6,489,346 B1 | 12/2002 | Phillips |
| 6,544,556 B1 | 4/2003 | Chen et al. |
| 6,599,529 B1 | 7/2003 | Skinhoj et al. |
| 6,610,323 B1 | 8/2003 | Lundberg et al. |
| 6,613,354 B2 | 9/2003 | Depui et al. |
| 6,632,451 B2 | 10/2003 | Penhasi et al. |
| 6,641,838 B2 | 11/2003 | Pather et al. |
| 6,645,988 B2 | 11/2003 | Phillips |
| 6,673,819 B2 | 1/2004 | Bergman et al. |
| 6,685,964 B1 | 2/2004 | Bartholomaeus et al. |
| 6,699,885 B2 | 3/2004 | Phillips |
| 6,713,089 B1 | 3/2004 | Bertelsen et al. |
| 6,749,867 B2 | 6/2004 | Robinson et al. |
| 6,780,882 B2 | 8/2004 | Phillips |
| 6,787,164 B2 | 9/2004 | Gelber et al. |
| 6,797,283 B1 | 9/2004 | Edgren et al. |
| 6,869,615 B2 | 3/2005 | Chen et al. |
| 6,875,872 B1 | 4/2005 | Lindberg et al. |
| 6,926,907 B2 | 8/2005 | Plachetka |
| 7,029,701 B2 | 4/2006 | Chen |
| 7,030,162 B2 | 4/2006 | Plachetka et al. |
| 7,060,694 B2 | 6/2006 | Plachetka et al. |
| 7,094,425 B2 | 8/2006 | Scott et al. |
| 7,332,183 B2 | 2/2008 | Plachetka et al. |
| 7,399,772 B2 | 7/2008 | Phillips |
| 7,411,070 B2 | 8/2008 | Cotton et al. |
| 7,488,497 B2 | 2/2009 | Depui et al. |
| 7,745,466 B2 | 6/2010 | Cotton et al. |
| 7,785,626 B2 | 8/2010 | Pettersson et al. |
| 7,846,914 B2 | 12/2010 | Petrus |
| 8,206,741 B2 | 6/2012 | Plachetka et al. |
| 9,220,698 B2 * | 12/2015 | Ault .................. A61K 31/192 |
| 9,393,208 B2 * | 7/2016 | Ault .................. A61K 31/192 |
| 2001/0025107 A1 | 9/2001 | Barberich et al. |
| 2002/0012676 A1 | 1/2002 | Lundberg et al. |
| 2002/0042433 A1 | 4/2002 | Yelle et al. |
| 2002/0044962 A1 | 4/2002 | Cherukuri et al. |
| 2002/0045184 A1 | 4/2002 | Chen |
| 2002/0051814 A1 | 5/2002 | Chen |
| 2002/0086029 A1 | 7/2002 | Lundberg et al. |
| 2002/0090395 A1 | 7/2002 | Woolfe et al. |
| 2002/0111370 A1 | 8/2002 | Bergman et al. |
| 2002/0155153 A1 | 10/2002 | Depui et al. |
| 2002/0160046 A1 | 10/2002 | Robinson et al. |
| 2003/0008903 A1 | 1/2003 | Barberich et al. |
| 2003/0040537 A1 | 2/2003 | Plachetka et al. |
| 2003/0069255 A1 | 4/2003 | Plachetka |
| 2003/0113375 A1 | 6/2003 | Lundberg et al. |
| 2003/0129235 A1 | 7/2003 | Chen et al. |
| 2003/0215527 A1 | 11/2003 | Phillips |
| 2003/0232080 A1 | 12/2003 | Pather et al. |
| 2003/0232876 A1 | 12/2003 | Plachetka |
| 2004/0022846 A1 | 2/2004 | Depui et al. |
| 2004/0048896 A1 | 3/2004 | Phillips |
| 2004/0121004 A1 | 6/2004 | Taneja |
| 2004/0131676 A1 | 7/2004 | Taneja |
| 2004/0171646 A1 | 9/2004 | Phillips |
| 2004/0180089 A1 | 9/2004 | Plachetka et al. |
| 2005/0004171 A1 | 1/2005 | Phillips |
| 2005/0042304 A1 | 2/2005 | Phillips |
| 2005/0054682 A1 | 3/2005 | Phillips |
| 2005/0147668 A1 | 7/2005 | Bertelsen et al. |
| 2005/0163847 A1 | 7/2005 | Cheng et al. |
| 2005/0227949 A1 | 10/2005 | Edalatpour et al. |
| 2005/0249806 A1 | 11/2005 | Proehl et al. |
| 2005/0249811 A1 | 11/2005 | Plachetka |
| 2006/0165797 A1 | 7/2006 | Plachetka |
| 2006/0177504 A1 | 8/2006 | Sundharadas |
| 2006/0178348 A1 | 8/2006 | Plachetka |
| 2006/0178349 A1 | 8/2006 | Plachetka |
| 2006/0287284 A1 | 12/2006 | Schutze et al. |
| 2007/0122470 A1 | 5/2007 | Johansson et al. |
| 2007/0154542 A1 | 7/2007 | Tananbaum et al. |
| 2007/0184078 A1 | 8/2007 | Chen |
| 2007/0207200 A1 | 9/2007 | Plachetka et al. |
| 2007/0237820 A1 | 10/2007 | Cheng et al. |
| 2007/0243251 A1 | 10/2007 | Taneja |
| 2008/0031941 A1 | 2/2008 | Pettersson |
| 2008/0031950 A1 | 2/2008 | Sesha |
| 2008/0103169 A1 | 5/2008 | Phillips |
| 2009/0074863 A1 | 3/2009 | Taneja |
| 2009/0075950 A1 | 3/2009 | Taneja |
| 2009/0163551 A1 | 6/2009 | Earnest |
| 2009/0280173 A1 | 11/2009 | Chauhan et al. |
| 2009/0297594 A1 | 12/2009 | Depui et al. |
| 2010/0062064 A1 | 3/2010 | Ault et al. |
| 2010/0172983 A1 | 7/2010 | Plachetka |
| 2010/0178334 A1 | 7/2010 | Johansson et al. |
| 2010/0330179 A1 | 12/2010 | Ault et al. |
| 2012/0064156 A1 | 3/2012 | Plachetka |
| 2013/0078305 A1 | 3/2013 | Plachetka |

FOREIGN PATENT DOCUMENTS

| | | |
|---|---|---|
| DE | 40 35 455 | 5/1992 |
| DE | 198 01 811 | 1/1998 |
| EP | 0 005 129 | 10/1979 |
| EP | 0 124 495 | 11/1984 |
| EP | 0 166 287 | 1/1986 |
| EP | 0 167 958 | 1/1986 |
| EP | 0 174 726 | 3/1986 |
| EP | 0 244 380 | 11/1987 |
| EP | 0 320 550 | 6/1989 |
| EP | 0 320 551 | 6/1989 |
| EP | 0 426 479 A1 | 5/1991 |
| EP | 0 426 479 B1 | 5/1991 |
| EP | 0 550 083 | 7/1993 |
| EP | 1 020 461 | 7/2000 |
| EP | 1 068 867 | 1/2001 |
| EP | 1 726 300 | 11/2006 |
| EP | 1 726 301 | 11/2006 |
| EP | 1 411 900 | 7/2010 |
| GB | 2 105 193 | 3/1983 |
| GB | 2 163 747 | 3/1986 |
| GB | 2 216 413 | 10/1989 |
| JP | 2005-145894 | 6/2005 |
| WO | WO 85/03433 | 8/1985 |
| WO | WO 90/06925 | 6/1990 |
| WO | WO 91/16886 | 11/1991 |
| WO | WO 91/16895 | 11/1991 |
| WO | WO 91/16896 | 11/1991 |
| WO | WO 91/19711 | 12/1991 |
| WO | WO 91/19712 | 12/1991 |
| WO | WO 93/11750 | 6/1993 |
| WO | WO 93/12817 | 7/1993 |
| WO | WO 94/07541 | 4/1994 |
| WO | WO 94/27988 | 12/1994 |
| WO | WO 95/01977 | 1/1995 |
| WO | WO 95/32959 | 12/1995 |
| WO | WO 96/05177 | 2/1996 |

(56) References Cited

FOREIGN PATENT DOCUMENTS

| | | |
|---|---|---|
| WO | WO 96/05199 | 2/1996 |
| WO | WO 96/14839 | 5/1996 |
| WO | WO 96/22780 | 8/1996 |
| WO | WO 97/11701 | 4/1997 |
| WO | WO 97/25064 | 7/1997 |
| WO | WO 98/13073 | 4/1998 |
| WO | WO 98/22117 | 5/1998 |
| WO | WO 98/22118 | 5/1998 |
| WO | WO 98/54171 | 12/1998 |
| WO | WO 99/00380 | 1/1999 |
| WO | WO 99/12524 | 3/1999 |
| WO | WO 99/29320 | 6/1999 |
| WO | WO 99/66919 | 12/1999 |
| WO | WO 00/01368 | 1/2000 |
| WO | WO 00/15195 | 3/2000 |
| WO | WO 00/56339 | 9/2000 |
| WO | WO 00/71122 | 11/2000 |
| WO | WO 00/72838 | 12/2000 |
| WO | WO 00/78293 | 12/2000 |
| WO | WO 01/66088 | 3/2001 |
| WO | WO 01/24777 | 4/2001 |
| WO | WO 02/22108 | 3/2002 |
| WO | WO 02/066002 | 8/2002 |
| WO | WO 02/098352 | 12/2002 |
| WO | WO 03/017980 | 3/2003 |
| WO | WO 2004/062552 | 7/2004 |
| WO | WO 2004/064815 | 8/2004 |
| WO | WO 2005/074536 | 8/2005 |
| WO | WO 2005/074930 | 8/2005 |
| WO | WO 2006/044202 | 4/2006 |
| WO | WO 2007/064274 | 6/2007 |
| WO | WO 2007/078874 | 7/2007 |
| WO | WO 2008/101060 | 8/2008 |
| WO | WO 2009/012393 | 1/2009 |
| WO | WO 2009/145905 | 12/2009 |
| WO | WO 2010/151697 | 12/2010 |

OTHER PUBLICATIONS

"Astrazeneca AB, Astrazeneca LP, KBI-E Inc., and Pozen, Inc. v Dr. Reddy's Laboratories Inc. and Dr. Reddy's Laboratories Ltd.: Dr. Reddy's Laboratories Inc. and Dr. Reddy's Laboratories Ltd's. Invalidity contentions pursuant to L. Pat. R. 3.6(c)," dated Nov. 23, 2011.

"Astrazeneca AB, Astrazeneca LP, KBI-E Inc., and Pozen, Inc. V Lupin Ltd. And Lupin Pharmaceuticals, Inc.: Defendants Lupin Ltd. and Lupin Pharmaceuticals, Inc's Amended Invalidity Contentions Pursuant to L. Pat. R. 3.3 and 3.6(c)," dated Apr. 20, 2012.

"Astrazeneca AB, Astrazeneca LP, KBI-E Inc., and Pozen, Inc. v Lupin Ltd. and Lupin Pharmaceuticals Inc.,: Defendants Lupin Ltd. and Lupin Pharmaceuticals, Inc.'s Invalidity Contentions Pursuant to L. Pat. R. 3.3 and 3.6(c)," dated Nov. 23, 2011.

"Astrazeneca AB, Astrazeneca LP, KBI-E Inc., and Pozen, Inc. v. Anchen Pharmaceuticals, Inc.: Anchen's Initial Invalidity Contentions," dated May 11, 2012.

"*Astrazeneca AB, Astrazeneca LP, KBI-E Inc., and Pozen, Inc. v. Dr. Reddy's Laboratories Inc. and Dr. Reddy's Laboratories Ltd* Plaintiffs' Response to DRL's First Set of Interrogatories to Plaintiffs (Nos. 1-5)," dated Mar. 5, 2012.

"Histamine H2 antagonist," accessed from <drugs.com> on Sep. 6, 2012.

Notice of Paragraph IV Certification Re: Dr. Reddy's Laboratories, Ltd.'s and Dr. Reddy's Laboratories, Inc.'s Naproxen and Esomeprazole Magnesium Delayed Release Tablets; U.S. Pat. No. 6,926,907, from Dr. Reddy's Laboratories, Ltd./Dr. Reddy's Laboratories, Inc., dated Mar. 11, 2011.

"PK Study to evaluate esomeprazole plasma levels following the administration of PN 400," ClinicalTrials.gov, Jan. 11, 2008, accessed from <http://clinicaltrials.gov/ct2/show/NCT00599404> on Sep. 6, 2012.

"Study evaluating the bioavailability of Naproxen 500 mg in three formulations," ClinicalTrials.gov, Apr. 23, 2008, accessed from <http://clinicaltrials.gov/ct2/show/NCT00665743>, on Sep. 6, 2012.

Abelo et al., "Pharmacodynamic modeling of reversible gastric acid pump inhibition in dog and man," *European Journal of Pharmaceutical Sciences*, 14:339-346, 2001.

Alberts et al., "Efficacy and Safety of PA, a Novel Combination of Enteric-Coated Aspirin and Immediate-Release Omeprazole," *International Stroke Conference*, 2009, retrieved from the Internet at: http://www.pozen.com/wp-content/uploads/2011/08/ISC2009Albertsfile.pdf, retrieved Dec. 14, 2012.

Alexander et al., "Pilot evaluation of a novel combination table (PN 400) containing a proton pump inhibitor and a nonsteroidal anti-inflammatory drug in prevention of upper gastrointestinal mucisal injury," *American Journal of Gastroenterology*, 100(9), S68, 135, 2005.

Andersson, "Pharmacokinetics, metabolism and interactions of acid pump inhibitors," *Clin Pharmacokinet.*, 31(1):9-28, 1996.

Anonymous, "Evaluate Relative Bioavailability of PA32540 (Asa/Omeprazole), Its Aspirin Component, and Ecotrin in Healthy Volunteers," ClinicalTrials.gov, Mar. 7, 2008, retrieved from the Internet at: http://www.clinicaltrials.gov/ct2/show/NCT00632086?term=aspirin+omeprazole&rank=18, retrieved on Dec. 28, 2012.

Anonymous, "Pozen's PA32520 Study Data Demonstrated Better Upper Gastrointestinal Protection," Drugs.com, Nov. 11, 2008, retrieved from the Internet at: http://www.drugs.com/clinical_trials/pozen-s-pa32520-study-data-demonstrated-better-upper-gastrointestinal-protection-6195.html, retrieved Dec. 17, 2012.

Anonymous, "Study Evaluating the Effect of Gastroduodenal Muosa of PA32540, A32540 and Celecoxib, and Aspirin with Celecoxib (PA32540-109)," ClinicalTrials.gov, Jan. 9, 2009, retrieved from the Internet at: http://www.clinicaltrials.gov/ct2/show/NCT00700687?term=aspirin+omeprazole&mnk=36, retrieved Dec. 18, 2012.

Anonymous, "Study to Evaluate the Incidence of Gastric Ulcers Following Administration of Either PA32540 or Enteric Coated Aspiring 325 mg in Subjects Who Are at Risk for Developing Aspirin-Associated Ulcers," ClinicalTrials.gov, Aug. 17, 2009, retrieved from the Internet at: http://clinicaltrials.gov/archive/NCT00960869/2009_08_17, retrieved Dec. 18, 2012.

Approval of Amendments/correction filed May 10, 2010 dated Jun. 21, 2010 (European application issued as EP 1 411 900 B1).

Awtry et al., "Aspirin," *Circulation*, 101:1206-1218, 2000.

Bajbouj et al., "A prospective multicenter clinical and endoscopic follow-up study of patients with gastroesophageal reflux disease," *Z. Gastroenterol.*, 43:1303-1307, 2005.

Ballinger et al., "COX-2 inhibitors versus NSAIDs in gastrointestinal damage and prevention," *Exp. Opin. Pharmacother.*, 2(1):31-40, 2001.

Barnett et al., "Effects of SCH 32651 on resting and stimulated acid secretion in guinea-pig isolated fundic mucosa," *Br. J. Pharmac.*, 83:75-82, 1984.

Berardi et al,. "Elevation of gastric pH with rantidine does not affect the release characteristics of sustained release ibuprofen tablets," *Biopharmaceutics & Drug Disposition*, 9:337-347, 1998.

Bergmann et al., "Protection against aspirin-induced gastric lesions by lansoprazole: simultaneous evaluation of functional and morphologic responses," *Clin. Pharmacol. Ther.*, 52:413-416, 1992.

Bianchi Porro et al., "Pantoprazole versus placebo in prevention of NSAID-induced ulcers," *Gastroenterology*, 114(4):A74, 1998.

Bianchi Porro et al., "Prevention of gastroduodenal damage with omeprazole in patients receiving continuous NSAIDs treatment. A double blind placebo controlled study," *Ital. J. Gasfroenterol. Hepatol.*, 30:43-47, 1998.

Bianchi Porro et al., "Why are non-steroidal anti-inflammatory drugs important in peptic ulcers?" *Aliment. Pharmacol. Therap.*, 1:540S-547S, 1987.

Bigard et al., "Complete prevention by omeprazole of aspirin induced gastric lesions in healthy subjects," *Gut*, 29(5):A712, T49, 1988.

(56) References Cited

OTHER PUBLICATIONS

Bigard et al., "Effet protecteur de l'omeprazole sur les lesions gastriques induites par une prise unique d'aspirine chez l'homme," *Gastroenterol. Clin. Biol.*, 12:770-771, 1998.

Bombardier et al., "Comparison of upper gastrointestinal toxicity of rofecoxib and naproxen in patients with rheumatoid arthritis," *N. Engl. J. Med.*, 343:1520-1528, 2000.

Brown et al., "Aspirin- and indomethacin-induced ulcers and their antagonism by antihistamines," *Euro. J. Pharm.*, 51:275-283, 1978.

Brown et al., "Prevention of the gastrointestinal adverse effects of nonsteroidal anti-inflammatory drugs," *Pract. Drug Safety*, 21:503-512, 1999.

Byrn et al., "Pharmaceutical solids: A strategic approach to regulatory considerations," *Pharm. Res.*, 12(7): 945-954, 1995.

Carrasco-Portugal et al., "Bioavailability of a formulation containing a diclofenac-rantidine combination," *Proc. West. Pharmacol. Soc.*, 45:8-10, 2002.

Chan et al., "Clopidogrel versus Aspirin and Esomeprazole to prevent recurrent ulcer bleeding," *New Eng. J. Med.*, 352:238-244, 2005.

Chan et al., "Eradication of H. Pylori versus maintenance acid suppression to prevent recurrent ulcer hemorrhage in high risk NSAID users: A prospective randomized study," *Gastroenterology*, 114: A87, G0356, 1998.

Chandramouli et al., "Prevention and management of NSAID-Induced gastropathy," *Journal of Pharmaceutical Pain and Symptom Control*, 8(4):27-40, 2000.

Chang et al., "Polymetharcrylates," In: Handbook of Pharmaceutical Excipients, Fifth Edition, Ed. Raymond C. Rowe, Paul J. Sheskey and Sian C. Owen, London: Pharmaceutical Press, pp. 553-560, 2006.

Chen et al., "Esomeprazole tablet vs. omeprazole capsule in treating erosive esophagitis," *World Journal of Gastroenterology*, 11(20):3112-3117, 2005.

Cullen et al., "Primary gastroduodenal prophylaxis with omeprazole for non-steroidal anti-inflammatory drug users," *Aliment. Pharmacol. Ther.*, 12:135-140, 1998.

Dajani, "Perspective on the gastric antisecretory effects of misoprostol in man," *Prostaglandins*, 33:68-77, 1987.

Daneshmend et al., "Abolition by omeprazole of aspirin induced gastric mucoasal injury in man," *Gut*, 31:514-517, 1990.

Daneshmend et al., "Use of microbleeding and an ultrathin endoscope to assess gastric mucosal protection by famotidine," *Gastroenterology*, 97:944-9, 1989.

Data sheet for "Arthrotec," 2009. (Document D8 from Letter to European Patent Office for counterpart European Application No. 02 734 602.2, regarding Oral Proceedings dated Dec. 18, 2009).

Dent, "Why proton pump inhibition should heal and protect against nonsteroidal anti-inflammatory drug users," *Am. J. Med.*, 104:52S-55S, 1998.

Ehsanullah et al., "Prevention of gastroduodenal damage induced by non-steroidal anti-inflammatory drugs: controlled trial of ranitidine," *BMJ* 297:1017-1021, 1998.

Ekstrom et al., Prevention of peptic ulcer and dyspeptic symptoms with omeprazole in pateitns receiving continuous non-steroidal anti-inflammatory drug therapy, *Scand. J. Gastroenterol.*, 31:753-758, 1996.

Ene et al., "A study of the inhibitory effects of SCH 28080 on gastric secretion in man," *Br. J. Pharmac.*, 76:389-391, 1982.

English translation of Bigard, et al., *Gastroenterol. Clin. Biol.*, 12:770-771, 1998.

English translation of Muller et al, *Arzneimittel Forschung*, 47:758-760, 1997.

English translation of Muller et al., *Arzneimittel-Forschung/Drug Res.*, 41(1):638-639, 1991.

English translation of Simon et al., *Arzneimittel Forschung*, 45:701-703, 1995.

Erlandsson et al., "Resolution of the enantiomers of omeprazole and some of its analogues by liquid chromatography on a trisphenycarbamoylcellulose-based stationary phase," *J. Chromatog.*, 532:305-319, 1990.

European Search Report and Opinion issued in European application No. EP 09 17 8773, dated Feb. 11, 2010.

European Search Report issued in European application No. EP 02 734 602.2, dated May 29, 2007.

Extended European Search Report issued in European Patent Application No. 10792681.8, dated Jan. 4, 2013.

Fass, "Erosive Esophagitis and Nonerosive Reflux Disease (NERD): Comparison of Epidemiologic, Physiologic, and Therapeutic Characteristics," *J. Clin. Gastroenterol.*, 41(2):131-137, 2007.

Feldman and Carlstedt, "Effect of antacid on absorption of enteric-coated aspirin," *JAMA*, 227(6):660-1, 1974.

Florence and Jani, "Novel oral drug formulations their potential in modulating adverse effects," *Drug Safety*, 10(3):233-66, 1994.

Fort et al., "Pa, a novel combination of delayed release (DR) aspirin (ASA) and immediate-release (IR) omeprazole, is associated with a decreased risk of gastroduodenal mucosal injury: Pooled data from three Phase I, 4-week endoscopic studies," *American Journal of Gastroenterology*, 103(Suppl. S):S487-S488, 2008.

Frank et al., "Reduction of indomerthacin induced gastrduodenal muclosal injury and gastrointestinal symptoms with cimetidine in normal subjects," *J. Rheum.*, 16:1249-1252, 1989.

Gengo et al., "Prevalence of platelet nonresponsiveness to aspirin in patients treated for secondary stroke prophylaxis and in patients with recurrent isochemic events," *J. Clin. Pharmacol.*, 48:335-343, 2008.

Goldstein et al, "PN400 significantly reduces the incidence of gastric ulcers compared with enteric-coated naproxen in patients requiring chronic NSAID therapy regardless of low-dose aspirin use: Results from two prospective, randomized controlled trials," POZEN Inc. sponsored study, 2009. (Document D16 from Letter to European Patent Office for counterpart European Application No. 02 734 602.2, regarding Oral Proceedings dated Dec. 18, 2009).

Goldstein et al., "116 a single table multilayer formulation of enteric-coated naproxen coupled with no-enteric-coated omeprazole is associated with a significantly reduced incidence of gastric ulcers vs. enteric-coated naproxen: A prospective, randomized double-blind study," 134(4), Supplement 1, A-19, 2008.

Goldstein et al., "PA32540 (Enteric-coated aspirin 325 mg + immediate-release omeprazole 40mg) is associated with significantly fewer gastric ulcers and significantly less endoscopic erosive esophagitis than enteric-coated aspirin (EC-ASA) alone: Results of two phase 3 studies," *The American Journal of Gastroenterology*, vol. 107, Suppl. 1, pp. S53-S54, 2012.

Goldstein et al., "PN400 significantly improves upper gastrointestinal tolerability compared with enteric-coated naproxen alone in patients requiring chronic NSAID therapy: Results from Two Prospective, Randomized, Controlled Trials," POZEN Inc. sponsored study, 2009. (Document D15 from Letter to European Patent Office for counterpart European Application No. 02 734 602.2, regarding Oral Proceedings dated Dec. 18, 2009).

Graham et al., "Duodenal and gastric ulcer prevention with misoprostol in arthritis pateitns taking NSAIDs," *Ann. Intern. Med.*, 119(4):257-262, 1993.

Grosser et al., "Thromboxane generation," In: Platelets, Alan Michelson Ed., pp. 565-574, Elseiver Science, 2007.

Gurbel et al., "Abstract 4267; PA32520 (Single-tablet of enteric-coated aspirin 325 mg + Immediate-release Omerpazole 20 mg); Aspirin therapy combining greater thrombozne suppression and lower upper gastrointestinal damage," *Circulation*, 118:S_855, 2008.

Gurbel et al., "PA32520 (Single-tablet of Immediate-Release Omeprazole 20 mg + Enteric-Coated Aspirin 325 mg): Safer Aspirin Therapy with Greater Thromboxane Suppression," Jul. 2009, retrieved from the Internet at: http://www.pozen.com/wp-content/themes/pozen/images/podf/ISTH2009%20Pozen%20draft0701.pdf, retrieved Dec. 18, 2012.

Hart et al., "Aspirin dosage and thromboxane synthesis in patients with vascular disease," *Pharmacotherapy*, 23(5):579-584, 2003.

(56) References Cited

OTHER PUBLICATIONS

Hassan-Alin et al., "Lack of drug-drug interaction between esomeprazole and naproxen in healthy subjects," *Gastroenterology*, 124(4), Supp.1, A541, 2003.
Hawkey et al., "Omeprazole anti-inflammatory compared with misoprostol for ulcers associated with nonsteroidal drugs," *N. Eng. J. Med.*, 338:727-734, 1998.
Hawkey et al., "Prophylaxis of aspirin-induced gasf ric mucosal bleeding with ranitidine," *Aliment. Pharmacol. Therap.*, 2:245-252, 1988.
Hawkey et al., "Strategies for preventing aspirin-induced gastric bleeding," *Scandinavian Journal of Gastroenterology*, vol. 21, Supplement 125, pp. 170-173, 1986.
Hawkey, "Non-steroidal anti-inflammatory drug gastropathy: causes and treatment," *Scan. J. Gastroenterol.*, 31 Suppl. 220:124-7, 1996.
Hawkey, "Progress in prophylaxis against nonsteroidal anti-inflammatory drug-associated ulcers and erosions," *Am. J. Med.*, 104:67S-74S, 1998.
Hawkins et al., "The Gastroduodenal Toxicity of Nonsteroidal Anti-Inflammatory Drugs. A Review of the Literature," *J. Pain and Symptom Management*, 20(2):140-151, 2000.
Helander et al., "Structure and function of rat parietal cells during treatment with omeprazole, SCH 28080, SCH 32651, or ranitidine," *Scan. J. Gastroenterol.*, 25:799-809, 1990.
Hogan et al., "Prescription of nonsteroidal anti-inflammatory drugs for elderly people in Alberta," *Can. Med. Assoc.*, 151(3):315-322,
Howden, "Clinical pharmacology of omeprazole," *Clin. Pharmacokinet.*, 20:38-49, 1991.
Ife et al., "Reversible inhibitors of the Gastric ($H^+/K^+$)-ATpase. 3. 3-Substituted-4-(phenylamino)quinolines," *J. med. Chem.*, 35:3413-3422, 1992.
Jacques et al., "Final purification, enrichment, of partially resolved enantiomer mixtures" In: Enantiomers, Racemates, and Resolutions, 423-434, 1981.
Jiranek et al., "Misoprostol reduces gastroduodenal injury from one week of aspirin: An endoscopic study," *Gastroenterology*, 96:656-661, 1989.
Johnson et al., "Esomeprazole once daily for 6 months is effective therapy for maintaining healed erosive esophagitis and for controlling gastroesophageal reflux disease symptoms: A randomized, double-blind, placebo-controlled study of efficacy and safety," *The American Journal of Gastroenterology*, 96(1):27-34, 2001.
Katz et al., "Gastric acidity and acid breakthrough with twice-daily omeprazole or iansoprazole," *Aliment. Pharmacol. Ther.*, 14:709-714, 2000.
Keeling et al.,"SK&F 96067 is a reversible, lumenally acting inhibitor of the gastric ($H^+ + K^+$)-ATPase," *Biochemical Pharmacology*, 42(1):123-130, 1991.
Kephart et al., "Coprescribing of nonsteroidal anti-inflammatory drugs and cytoprotective and antiulcer drugs in Nova Scotia's senior populations," *Clin. Ther.*, 17:1159-1173, 1995.
Kimmey et al., "Role of $H_2$-receptor blockers in the prevention of gastric injury resulting from nonsteroidal anti-inflammatory agents," *Am. J. Med.*, 84:49-52, 1988.
Kitchingman et al., "Enhanced gastric mucosal bleeding with doses of aspirin used for prophylaxis and its reduction by rantidine," *Br. J. Clin. Pharmac.*, 28:581-585, 1989.
Konturek et al., "Effects of omeprazole, a substituted benzimidazole, on gastrointestinal secretions, serum gastrin, and gastric mucosal blood flow in dogs," *Gastroenterology*, 86(1):71-77, 1984.
Labenz et al., "Risk factors for erosive esophagitis: A multivariate analysis based on the proGERD study initiative," *American Journal of Gastroenterology*, 99:1652-1656, 2004.
Lad et al., "Management of nonsteroidal anti-inflammatory drug-induced gastroduodenal disease by acid suppression," *Can. J. Gastroenterol.*, 13:135-142, 1999.

Larvas, "Prevention of aspirin-induced gastroduodenal damage: *H. Pylori* infection eradication versus proton pump inhibitors or both," *Digestive and Liver Disease*, 36:655-657, 2004.
Lanza et al., "A double-blind placebo-controlled comparison of the efficacy and safety of 50, 100, and 200 µg of misoprostol QID in the prevention of ibuprofen-induced gastric and duodenal mucosal lesions and symptoms," *Am. J. Gastroenterol.*, 84(6):633-636, 1989.
Lanza et al., "Double-blinded, placebo-controlled endoscopic comparison of the mucosal protective effects of misoprostol versus cimetidine on tolmetin-induced injury to the stomach and duodenum," *Gastroenterology*, 95:289-294, 1988.
Larsson et al., "Animal pharmadynamics of omeprazole. A survey of its pharmacological 1985.properties in vivo," *Scand J Gastroenterol Suppl.*, 108:23-35, 1985.
Lee et al., "Omeprazole prevents indomethacin-induced gastric ulcers in rabbits" *Aliment. Pharmacol. Ther.*, 10:571-576, 1996.
Leese et al., "Effects of celecoxib, a novel cyclooxygenase-2 inhibitor, on platelet function in healthy Adults: A randomized, controlled trial," *J. Clin. Pharmacol.*, 40:124-132, 2000.
Leonards and Levy, "Reduction or prevention of aspirin-induced occult gastrointestinal blood loss in man," *Clinical Pharmacology and Therapeutics*, 10(4):571-5, 1969.
Letter to European Patent Office for counterpart European Application No. 02 734 602.2, regarding Oral Proceedings dated Dec. 18, 2009.
Lichtenberger et al., "Nonsteroidal anti-inflammatory drug and phospholipid prodrugs: combination therapywith antisecretory agents in rats," *Gastroentereology*, 111:990-995, 1996.
Lin and Lu, "Role of pharmacokinetics and metabolism in drug discovery and development," *Pharmacological Reviews*, 49(4):403-449, 1997.
Maggi et al., "Press-coated tablets for the sequential pulsed administration of two different drugs," *Int. J. Pharm.*, 99:173-179, 1993.
Mason and Winer, "Kinetics of aspirin, salicylic acid, and salicyclic acid, and salicyluric acid following oral administration of aspirin as a tablet and two buffered solutions," *Journal of Pharmaceutical Sciences*, 70(3):262-5, 1981.
Mattsson et al., "Omeprazole provides protection against experimentally induced gastric mucosal lesions," *Eur. J. Pharmacol.*, 91:111-114, 1983.
McKeage et al., "Esomeprazole: a review of its use in the management of gastric acid-related diseases in adults," *Drugs*, 68(11):1571-1607, 2008.
Miner et al., "Clinical trial: evaluation of gastric acid suppression with three doses of immediate-release esomeprazole in the fixed-dose combination of PN 400 (naproxen/esomeprazole magnesium) compared with naproxen 500 mg and enteric-coated esomeprazole 20 mg: a randomized, open-label, Phase I study in healthy volunteers," *Aliment. Pharmacol. Ther.*, 32(3):414-424, 2010.
Miner et al., "PA32540, a tablet containing enteric-coated (EC) aspirin 325 mg and unbuffered immediate-release omeprazole 40 mg, provides percent time gastric pH >4 significantly less than EC omeprazole 40 mg, but with faster onset and less exposure to omeprazole," *Gastroenterology*, vol. 142, Issue 5, Supplement 1, p. S-3, 2012.
Miner et al., "T1969 Gastric acid suppression with PN400, a single-tablet, multilayer, fixed dose formulation combining an immediate-release esomeprazole layer and an enteric-coated (EC) naproxen core," *Gastroenterology*, 136(5), Suppl. 1, A-611, 2009.
Miner et al., "T1972 Pharmacokinetics of naproxen and esomeprazole in pn400, a single-tablet, multilayer formulation of enteric-coated naproxen coupled with immediate-release esomeprazole," *Gastroenterology*, 136(5), Suppl. 1, A-612, 2009.
Morgner et al., "Esomeprazole: prevention and treatment of NSAID-induced symptoms and ulcers," *Expert Opin Pharmacother.*, 8(7):975-988, 2007.
Morris et al., "Gastric cytoprotection is secondary to increased mucosal fluid secretion: A study of six cytoprotective agents in the rat," *J. Clin. Gastroenterol.*, 27(Suppl. 1):S53-63, 1998.
Morrison et al., "The optimal analgesic dose of rofecoxib: overview of six randomized controlled trials," *JADA*, 131:1729-1737, 2000.

(56) References Cited

OTHER PUBLICATIONS

Muller et al., "Untersuchungen zur schutzwirkung von lansoprazol auf die menschliche magenschleimhaut gegenuber niedrig dosierter acetylsalicylsaure," *Arzneimittel Forschung*, 47:758-760, 1997.

Muller et al., "Verbesserung der gastroduodenalen vertraglichkeit von azetylsalizylsaure durch ranitidine," *Arzneimittel-Forschung/Drug Res.*, 41(1):638-639, 1991.

Naesdal et al., "Gastro-duodenal protection in an era of cyclo-oxygenase-2-selective nonsteroidal anti-inflammatory drugs," *European Journal of Gastroenterology & Hepatology*, 13(12):1401-1406, 2001.

Nefesoglu et al., "Interaction of omeprazole with enteric-coated Salicylate tablets," *International Journal of Clinical Pharmacology and Therapeutics*, 36(10):549-553, 1998.

Neuvonen and Kivisto, "Enhancement of drug absorption by antacids," *Clin. Pharmacokinet.*, 27(2):120-8, 1994.

Notice of Allowance issued in U.S. Appl. No. 10/158,216, dated Mar. 29, 2005.

Notice of Allowance issued in U.S. Appl. No. 11/129,320, dated May 11, 2012.

Notice of Opposition to a European Patent, submitted against European Patent application No. EP 1 411 900 dated Apr. 15, 2011.

Notice of Opposition to a European Patent, submitted against European Patent application No. EP 1 411 900 dated Apr. 20, 2011.

Oddsson et al., "Comparison between ranitidine and omeprazole for protection against gastroduodenal damage caused by naproxen," *Scand. J. Gastroenterol.*, 27:1045-1048, 1992.

Oddsson et al., "Endoscopic findings in the stomach and duodenum after treatment with enteric-coated and plain naproxen tablets in healthy subjects," *Scand. J. Gastroenterol.*, 25:231-234, 1990.

Office Communication issued in Australian Patent Application No. 2010266026, dated Dec. 11, 2013.

Office Communication issued in Canadian Patent Application No. 2,449,098, dated Nov. 6, 2008.

Office Communication in Chinese Patent Application No. 201080037566.1, dated Jan. 10, 2014. (English translation of Chinese text).

Office Communication issued in Egyptian Patent Application No. 2121/2001, dated Apr. 13, 2013.

Office Communication issued in Eurasian Patent Application No. 201270071, dated Aug. 5, 2013. (English translation of Russian text).

Office Communication issued in European Patent Application No. 02 734 602.2, dated Jun. 30, 2008.

Office Communication issued in European Patent Application No. 02 734 602.2, dated Dec. 18, 2007.

Office Communication issued in European Patent Application No. 02 734 602.2, dated Feb. 22, 2010.

Office Communication issued in European Patent Application No. 02 734 602.2, dated Apr. 29, 2010.

Office Communication issued in European Patent Application No. 10 177 150.9, dated Nov. 12, 2010.

Office Communication issued in Israeli Patent Application No. 159129, dated Aug. 22, 2010. (English translation).

Office Communication issued in Israeli Patent Application No. 159129, dated Feb. 16, 2010. (English translation).

Office Communication issued in Israeli Patent Application No. 159129, dated Jul. 22, 2009. (English translation).

Office Communication issued in Israeli Patent Application No. 159129, dated Aug. 8, 2007. (English translation).

Office Communication issued in Japanese Patent Application No. 2003-501394, dated Jul. 25, 2008. (English translation).

Office Communication issued in Japanese Patent Application No. 2003-501394, dated Jan. 5, 2010. (English translation).

Office Communication issued in Norwegian Patent Application No. 20035275, dated Jul. 14, 2011. (English Translation).

Office Communication issued in U.S. Appl. No. 10/158,216, dated Apr. 22, 2004.

Office Communication issued in U.S. Appl. No. 10/158,216, dated Oct. 20, 2004.

Office Communication issued in U.S. Appl. No. 13/215,855, dated Feb. 28, 2013.

Office Communication issued in U.S. Appl. No. 13/215,855, dated Jun. 6, 2012.

Office Communication issued in U.S. Appl. No. 11/129,320, dated Oct. 25, 2010.

Office Communication issued in U.S. Appl. No. 11/129,320, dated Nov. 19, 2009.

Office Communication issued in U.S. Appl. No. 11/129,320, dated Mar. 30, 2009.

Office Communication issued in U.S. Appl. No. 11/129,320, dated Sep. 22, 2008.

Office Communication issued in U.S. Appl. No. 11/129,320, dated Jun. 16, 2011.

Office Communication issued in U.S. Appl. No. 11/129,320, dated Jan. 17, 2012.

Office Communication issued in U.S. Appl. No. 12/823,082, dated Jul. 18, 2013.

Office Communication issued in U.S. Appl. No. 12/823,082, dated Sep. 17, 2012.

Office Communication issued in U.S. Appl. No. 11/129,320, dated Nov. 15, 2011.

Office Communication issued in U.S. Appl. No. 11/129,320, dated Mar. 7, 2012.

Office Communication issued in U.S. Appl. No. 11/129,320, dated Apr. 19, 2012.

Office Communication issued in U.S. Appl. No. 13/475,446, dated Mar. 11, 2013.

Office Communication issued in U.S. Appl. No. 12/822,612, dated Jul. 18, 2013.

Office Communication issued in U.S. Appl. No. 12/822,612, dated Sep. 14, 2012.

Office Communication issued in U.S. Appl. No. 13/215,855, dated Dec. 12, 2012.

Office Communication issued in U.S. Appl. No. 12/553,107, dated Jul. 30, 2012.

Office Communication issued in U.S. Appl. No. 12/553,107, dated Jan. 5, 2012.

Office Communication issued in U.S. Appl. No. 14/753,195, dated Aug. 14, 2015.

Office Communication issued in U.S. Appl. No. 12/553,107, dated Jun. 16, 2014.

Office Communication issued in U.S. Appl. No. 12/533,107, dated Mar. 26, 2015.

Office Communication issued in U.S. Appl. No. 12/553,107, dated Oct. 9, 2015.

Office Communication issued in U.S. Appl. No. 14/980,639, dated Apr. 4, 2016.

Okabe et al., "Antisecretory effect of leminoprazole on histamine-stimulated gastric acid secretion in dogs: potent local effect," *Jpn. J. Pharmacol.*, 69:91-100, 1995.

Okabe et al., "Pharmacological regulation of gastric acid secretion in the apical membrane of parietal cells; a new target for antisecretory drugs," *Journal of Physiology and Pharmacology*, 52(4):639-656, 2001.

Panara et al., "Effects of the novel anti-inflammatory compounds, N-[2-(cyclohexyloxy)-4-nitrophenyl] methanesulphonamide (NS-398) and 5-methanesulphonamido-6-(2,4-difluorothio-phenyl)-1-inda none (L-745,337), on the cyclo-oxygenase activity of human blood prostaglandin endoperoxide synthases," *British Journal of Pharmacology*, 116:2429-2434, 1995.

Pang et al., "Modeling of intestinal drug absorption: roles of transporters and metabolic enzymes (for the Gillette review series)" *Drug Metabolism and Disposition*, 31(12): 1507-1519, 2003.

Pasero et al., "Aceclofenac versus naproxen in the treatment of ankylosing spondylitis: A double-blind, controlled study," *Current Therapeutic Research*, 55(7):833-842, 1994.

Patrono et al., "Low-dose aspirin for the prevention of Atherothrombosis," *New Eng. J. Med.*, 353:2373-2383, 2005.

PCT International Preliminary Examination Report, issued in International Application No. PCT/US2002/017105, dated May 7, 2003.

(56) References Cited

OTHER PUBLICATIONS

PCT International Preliminary Report on Patentability issued in International Application No. PCT/US2009/003281, dated Nov. 30, 2010.
PCT International Preliminary Report on Patentability issued in International Application No. PCT/GB2009/051108, dated Mar. 24, 2011.
PCT International Preliminary Report on Patentability issued in International Application No. PCT/SE2010/050712, dated Jan. 4, 2012.
PCT International Search Report and Written Opinion issued in International Application No. PCT/US10/39864, dated Aug. 30, 2010.
PCT International Search Report and Written Opinion issued in International Patent Application No. PCT/GB2009/051108, dated Nov. 13, 2009.
PCT International Search Report and Written Opinion issued in International Patent Application No. PCT/SE2010/050712, dated Sep. 20, 2010.
PCT International Search Report issued in International Application No. PCT/US02/17105, dated Mar. 14, 2003.
PCT Supplemental International Search Report issued in International Patent Application No. PCT/GB2009/051108, dated Sep. 28, 2010.
PCT Supplementary International Search Report issued in International Patent Application No. PCT/SE2010/050712, dated Oct. 20, 2011.
Petersen, "Doubts are raised on the safety of 2 popular arthritis drugs," *NY Times*, p. C1, Published May 22, 2001.
Pilbrant et al., "Development of an oral formulation of omeprazole," *Scand. J. Gastroenterol.*, 20(Suppl. 109):113-120, 1985.
Pirmohamed et al., "Adverse drug reactions as cause of admission to hospital: prospective analysis of 18,820 patients," *Br. Med. J.*, 329:15-19, 2004.
Porter S.C., "Coating of Pharmaceutical Dosage Forms," in: A. Gennaro (Ed.), *Remington: the Science and Practice of Pharmacy*, 19th edition. 1650-1651, 1995.
Preliminary Amendment filed in U.S. Appl. No. 13/475,446, filed May 18, 2012.
Press Release for Vimovo, Oct. 16, 2009. (Document D14 from Letter to European Patent Office for counterpart European Application No. 02 734 602.2, regarding Oral Proceedings dated Dec. 18, 2009).
Qureshi et al., "Pharmacokinetics of two enteric-coated ketoprofen products in humans with or coadministration of omeprozole and comparison with dissolution findings," *Pharmaceutical Research*, 11(11):1669-1672, 1994.
Ramage et al., "Inhibition of food stimulated acid secretion by misoprostol, an orally active synthetic E1 analogue prostaglandin," *Br. J. Clin. Pharmac.*, 19:9-12, 1985.
Raskin et al., "Misprostol dosage in the prevention of nonsteroidal anti-inflammatory drug-induced gastric and duodenal ulcers: a comparison of three regiments," *Ann. Intern. Med.*, 123(5):344-350, 1995.
*Remington's Pharmaceutical Sciences*, 17th ed., University of Sciences in Philadelphia, 1985.
Reply to EPO communication of Apr. 29, 2010, dated May 10, 2010 (German and French translation of claims omitted).
Richardson et al., "Proton pump inhibitors, pharmacology and rationale for use in gastrointestinal disorders," *Drugs*, 56(3):307-35, 1998.
Robinson et al., "Effects of ranitidine gastroduodenal mucosal damage induced by nonsteroidal anti-inflammatory drugs," *Dig. Disc. Sci.*, 34(3):424-428, 1989.
Roche Naproxen EC label, copyright 1999.
Roth et al., "Cimetidine therapy in nonsteroidal anti-inflammatory drug gastropathy: double-blind long-term evaluation," *Arch. Intern. Med.*, 147:1798-1801, 1987.

Rubinstein, "Gastrointestinal anatomy physiology and permeation pathways," *Enhancement in Drug Discovery*, CRC Press, 3-35, 2007.
Sangiah et al., "Effects of misoprostol and omeprazole on basal gastric pH and free acid content in horses," *Res. Vet. Sci.*, 47(3):350-354, 1989.
Savarino et al., "Effect of one-month tratment with nonsteroidal anti-inflammatory drugs (NSAIDs) on gastric pH of rheumatoid arthiritis patients," *Digestive Diseases and Sciences*, 43:459-463, 1998.
Scarpignato et al., "Towards a GI safer anti-inflammatory therapy," *Gastroenterology International*, 186-215, 1999.
Scheiman et al., "Omeprazole ameliorates aspirin-induced gastroduondenal injury," *Digestive Diseases and Sciences*, 39(1):97-103, 1994.
Scheiman, "NSAID-induced peptic ulcer disease: a critical review of pathogenesis and management," *Dig. Dis.*, 12:210-222, 1994.
Scheiman, "Pathogensis of gastroduoduenal injury due to nonsteroidal and anti-inflammatory drug: Implications for prevention and therapy," *Seminars in Arthritis and Rheumatism*, 21(4):259-268, 1992.
Scott and Sundell, "Inhibition of H+K+ ATPase by SCH 28080 and SCH 32651," *European Journal of Pharmacology*, 112:268-270, 1985.
Seitz et al., "Tablet Coating," In: The Theory and Practice of Industrial Pharmacy. Eds. Leon Lachman, Herbert A. Lieberman and Joseph L. Kanig. Philadelphia: Lea & Febiger, pp. 346-373, 1986.
Selway, "Potential hazards of long-term acid suppression," *Scand. J. Gastroenterol.*, 25(Suppl. 178):85-92, 1990.
Sharma et al., "Comparison of 24-hour intragastric pH using four liquid formulations of lansoprazole and omerprazole," *Am. J. Health-Syst. Pharm.*, 56(Suppl. 4):518-21, 1999.
Silverman, *The Organic Chemistry of Drug Design and Drug Action*, 2nd Edition, Academic Press, p. 102 & p. 527, 2004.
Silverstein et al., "Gastrointestinal toxicity with Celecoxib versus nonsteroidal anti-inflammatory drugs for osteoarthritis and rheumatoid arthritis; the Class study: A randomized controlled trial," *JAMA*, 284:1247-1255, 2000.
Silverstein et al., "Misoprostol reduces serious gastrointestinal complications in paetints with rheumatoid arthritis receiving nonsteroidal anti-inflammatory drugs," *Ann. Intern. Med.*, 123(4):241-249, 1995.
Simon et al.,"Schutzwirkung von omeprazol genguber niedrig dosierter acetylsalicylsaure," *Arzneimittel Forschung*, 45:701-703, 1995.
Summons to Attend Oral Proceedings Pursuant to Rule 116(1): EPC, dated Sep. 3, 2009, issued in European Patent Application No. 02, 734 602.2.
Sung, "Management of nonsteroidal anti-inflammatory drug-related peptic ulcer bleeding," *Am. J. Med.*, 110(1A): 29S-32S, 2001.
Taha et al., "Famotidine for the prevention of peptic ulcers and oesophagitis in patients taking low-dose aspirin (Famous): a phase III, randomized, double-blind, placebo-controlled trial," *Lancet*, 374:119-25, 2009.
Takeuchi et al., "Effects of topical application of acidified omeprazole on acid secretion and transmucosal potential difference in anesthetized rat stomachs," *Japan J. Pharmacol.*, 47:397-408, 1988.
Tronstad et al., "Gastroscopic findings after treatment with enteric-coated and plain naproxen tablets in healthy subjects," *Scand. J. Gastroenterol.*, 20:239-242, 1985.
Vane et al., "The future of NSAID therapy: selective COX-2 inhibitors," *IJCP*, 54(1):7-9, Jan./Feb. 2000.
von Unge et al., "Stereochemical assignment of the enantiomers of omeprazole from X-ray anaylysis of a fenchyloxymethyl derivative of (+)-(R)- omeprazole," *Tetrahedron*, 8(12):1967-1970, 1997.
Wagner et al., "Effects of nonsteroidal anti-inflammatory drugs on ulcerogensis and gastric secretion in pylorus-ligated rat," *Digestive Diseases and Sciences*, 40:134-140, 1995.
Wakitani et al., "Profile of JTE-522 as a human cyclooxygenase-2 inhibitor," *Jpn. J. Pharmacol.*, 78:365-371, 1998.

(56) References Cited

OTHER PUBLICATIONS

Wallmark et al., "The relationship between gastric acid secretion and gastric $H^+$, $K^+$-ATPase activity," *J. Biol.Chem..*, 260(25): 13681-13684, 1985.

Warner et al., "Nonsteroidal drug selectives for cyclo-oxygenase-1 rather than cyclo-oxygenase-2 are associated with human gastrointestinal toxicity: a full in vitro analysis," *Proc. Natl. Acad. Sci. USA*, 96:7563-7568, 1999.

Weil et al, "Prophylactic aspirin and risk of peptic ulcer bleeding," *BMJ*, 310: 827-830, 1995.

Wilson et al., "Effects of misoprostol on gastric acid and mucus secretion in man," *Digestive Diseases and Sciences*, 31(2): 126S-129S, 1986.

Wolfe et al., "Acid suppression: optimizing therapy for gastroduodenal ulcer healing, gastroesophageal reflux disease, and stress related erosive syndrome," *Gastroenterology*, 18(2):S9-S31, 2000.

Wolfe et al., "Gastrointestinal toxicity of nonsteroidal anti-inflammatory drugs," *N. Engl. J. Med.*, 340:1888-1899, 1999.

Yeomans et al., "A comparison of omeprazole with rantidine for ulcers associated with nonsteroidal anti-inflammatory drugs," *N. Engl. J. Med.*, 338:719-726, 1998.

Yeomans et al., "Efficacy of esomeprazole (20 mg once daily) for reducing the risk of gastroduodenal ulcers associated with continuous use of low-dose aspirin," *American Journal of Gastroenterology*, 103:1-9, 2008.

Yeomans et al., "New data on healing of nonsteroidal anti-inflammatory drug-associated ulcers and erosions," *Am. J. Med.*, 104:56S-61S, 1998.

\* cited by examiner

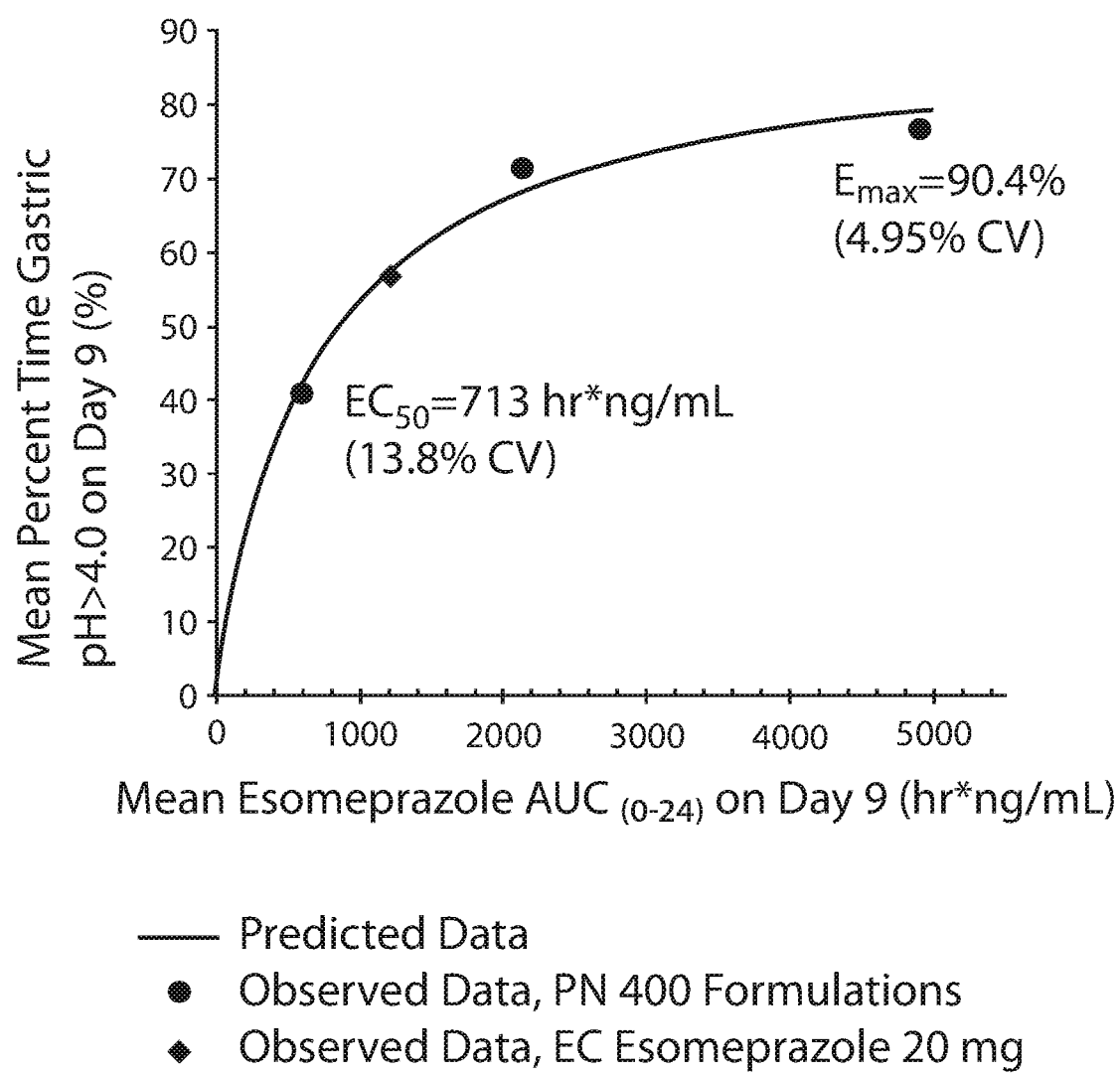

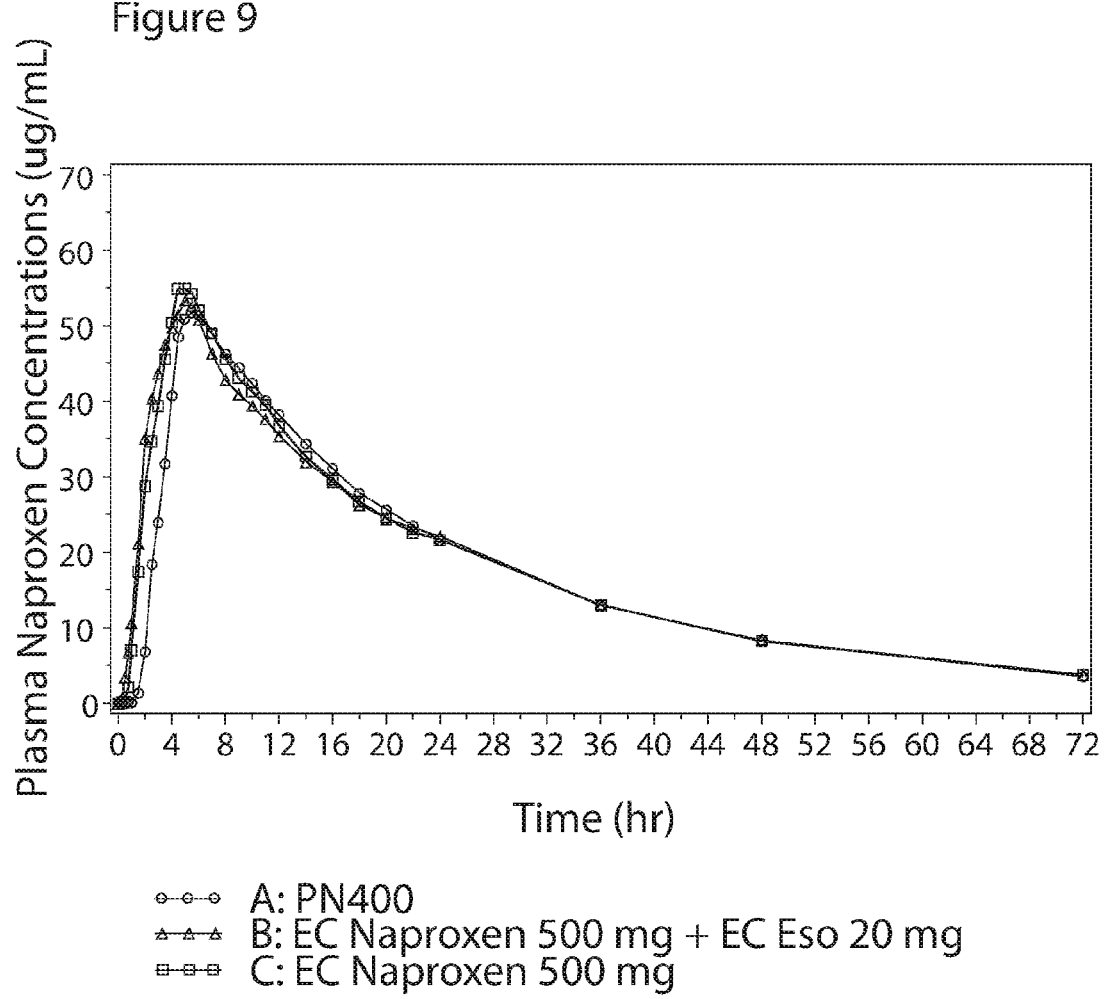

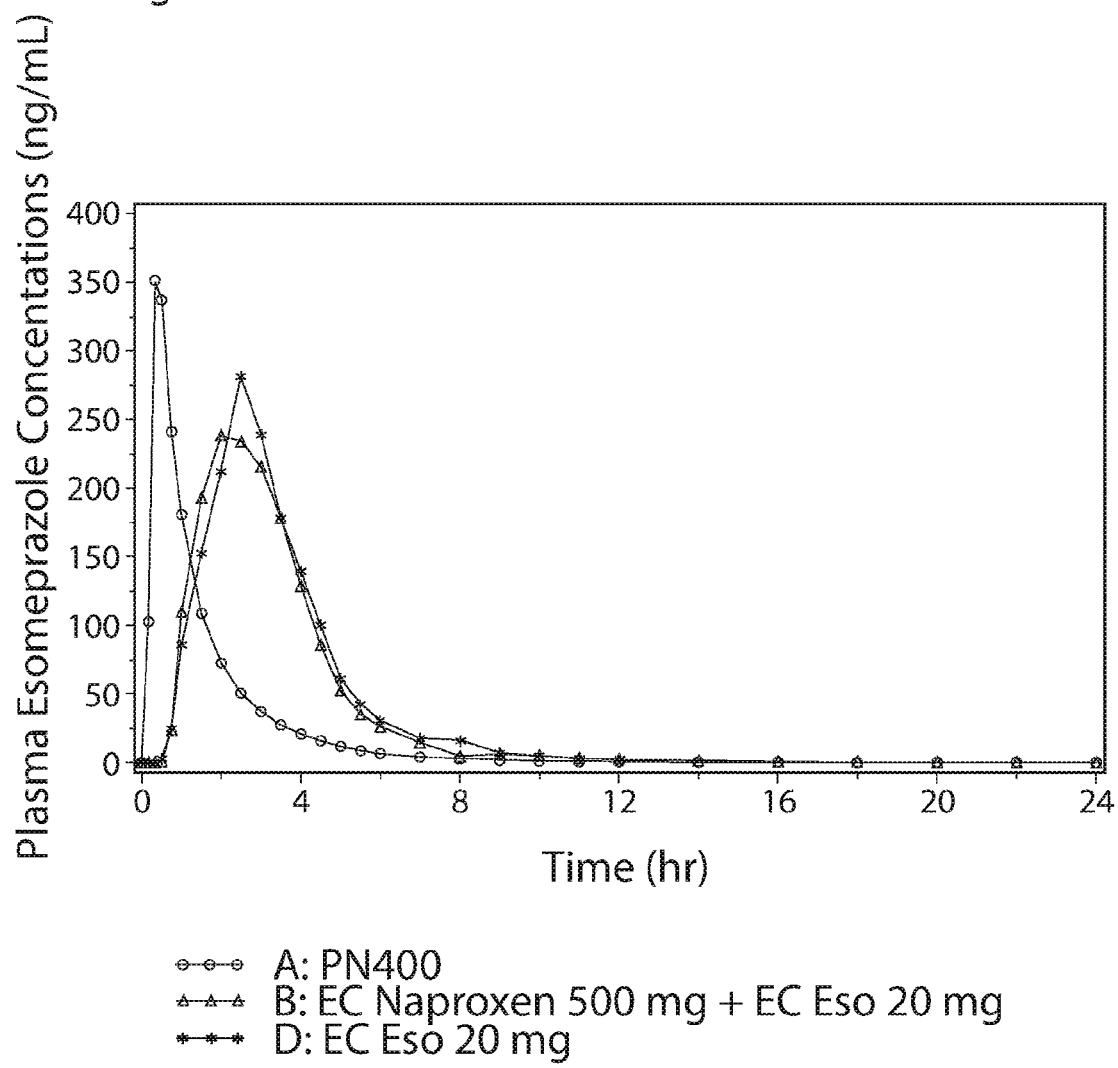

METHOD FOR DELIVERING A PHARMACEUTICAL COMPOSITION TO PATIENT IN NEED THEREOF

This application is a continuation application of U.S. patent application Ser. No. 14/980,639, filed Dec. 28, 2015, which is a continuation application of U.S. patent application Ser. No. 12/553,107, filed Sep. 3, 2009, now U.S. Pat. No. 9,220,698, issued on Dec. 29, 2015, which claims priority to U.S. Provisional Patent Application No. 61/095,584, filed Sep. 9, 2008. The entire contents of the above-referenced disclosures are specifically incorporated herein by reference.

The present disclosure is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof.

Over 15 million Americans take nonsteroidal anti-inflammatory drugs (NSAIDs) each day as a treatment for pain or inflammation. Unfortunately, many of these NSAIDs are associated with a high incidence of gastrointestinal complications, including gastritis, dyspepsia, gastroduodenal ulcers, perforations, and bleeding. A major factor contributing to the development of gastrointestinal lesions appears to be the presence of acid in the stomach and upper small intestines.

During recent years, attempts have been made to reduce the gastrointestinal risk associated with taking NSAIDs by administering agents that inhibit stomach acid secretion, such as, for example, proton pump inhibitors with the NSAID. For example, U.S. Pat. No. 6,926,907 is directed to at least one drug dosage form comprising a proton pump inhibitor that raises the pH of a patient's gastrointestinal tract, followed by an NSAID. This, and similar, formulations can be effective in improving NSAID tolerability through dosages of esomeprazole and naproxen that produce the desired pharmacodynamic response and pharmacokinetic values. Parameters that may influence the desired pharmacodynamic response and pharmacokinetic values include, but are not limited to, for example, the dosage of each; extent of drug absorption; extent of drug distribution, and the duration of drug administration.

There is a need for a clinically effective therapy that delivers to a patient in need thereof a pharmaceutical composition in a unit dose form comprising naproxen, or pharmaceutically acceptable salt thereof, and esomeprazole, or pharmaceutically acceptable salt thereof, for a duration sufficient to achieve an instragastric pH of about 4 or greater and a plasma level of naproxen that is efficacious.

In one aspect, the disclosure is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater to target: a mean % time at which intragastric pH remains at about 4.0 or greater for about a 24 hour period of at least about 41%.

In another aspect, the disclosure is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target
  i) a pk profile for naproxen where:
    a) the AM dose has a mean $C_{max}$ of about 81 μg/ml and a median time to maximum concentration ($T_{max}$) of from about 2.5 to about 4 hours, and
    b) the PM dose has a mean $C_{max}$ of about 76.2 μg/ml and a median $T_{max}$ of from about 10 to about 14 hours; and
  ii) a pk profile for esomeprazole where:
    a) the AM dose has a mean area under the plasma concentration-time curve from time zero when the AM dose is administered to about 10 hours after the AM dose is administered ($AUC_{0-10,am}$) is about 850 hr*ng/mL, and
    b) the PM dose has a mean area under the plasma concentration-time curve from time zero when the PM dose is administered to about 14 hours after the PM dose is administered ($AUC_{0-14,pm}$) is about 650 hr*ng/mL.

Yet another aspect is directed to delivering a pharmaceutical composition in unit dose form that provides the pharmacodynamic response and/or pharmacokinetic values disclosed herein to a patient being treated for a disease or disorder selected from pain and inflammation.

A further aspect is directed to delivering a pharmaceutical composition in unit dose form that provides the pharmacodynamic response and/or pharmacokinetic values disclosed herein to a patient being treated for osteoarthritis, rheumatoid arthritis, ankylosing spondylitis, or a combination thereof.

A still further aspect is directed to delivering a pharmaceutical composition in unit dose form that provides the pharmacodynamic response and/or pharmacokinetic values disclosed herein to an at risk patient.

Another aspect is directed to delivering a pharmaceutical composition in unit dose form that provides the pharmacodynamic response and/or pharmacokinetic values disclosed herein to an at risk patient being treated for a disease or disorder selected from pain and inflammation.

A further aspect is directed to delivering a pharmaceutical composition in unit dose form that provides the pharmacodynamic response and/or pharmacokinetic values disclosed herein to an at risk patient being treated for osteoarthritis, rheumatoid arthritis, ankylosing spondylitis, or a combination thereof.

Yet another aspect is directed to delivering a pharmaceutical composition in unit dosage form that provides the pharmacodynamic response and/or pharmacokinetic values disclosed herein via a multilayer tablet comprising at least one core and at least a first layer and a second layer, wherein:
  i) said core comprises naproxen, or pharmaceutically acceptable salt thereof;
  ii) said first layer is a coating that at least begins to release the naproxen, or pharmaceutically acceptable salt thereof, when the pH of the surrounding medium is at about 3.5 or greater; and
  iii) said second layer is esomeprazole, or pharmaceutically acceptable salt thereof, wherein said esomeprazole, or pharmaceutically acceptable salt thereof, is released at a pH of from about 0 or greater.

BRIEF DESCRIPTION OF THE DRAWINGS

FIG. 7: Correlation of plasma exposure to esomeprazole with effect on intragastric pH on day 9.

FIG. 9: Time course of plasma naproxen concentration.

FIG. 10: Time course of plasma esomeprazole concentration.

Figure 1:
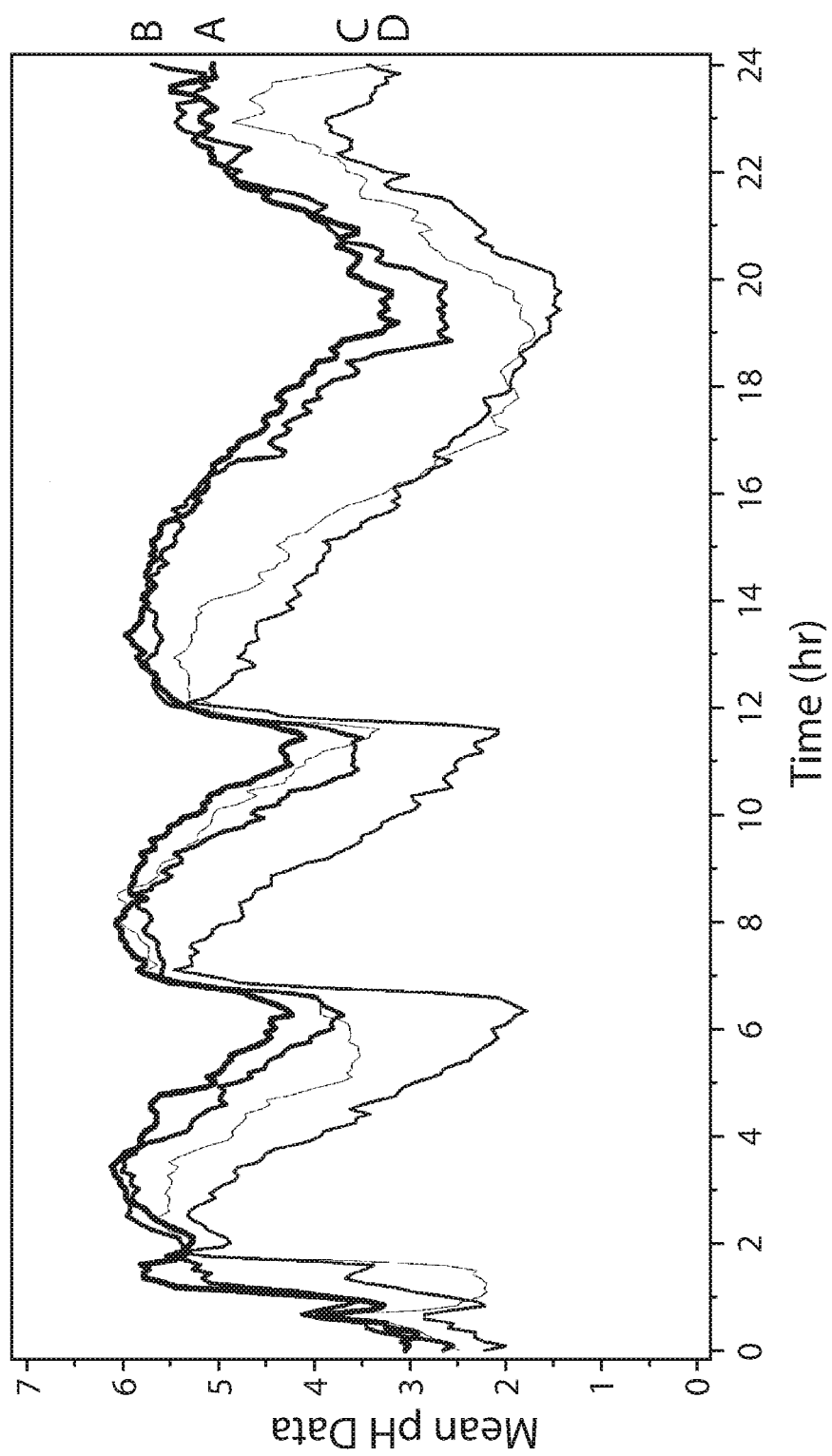
FIG. 1: Mean pH data over 24 hours on day 9 per protocol population. Treatment A=PN400/E30; B=PN400/E20; C=PN400/E10; D=EC E20+naproxen.

Abbreviations and/or special terms that may be used herein are set forth in Table 1 and the text that follows.

TABLE 1

Abbreviations and Special Terms

| Abbreviation | Explanation |
|---|---|
| ANOVA | analysis of variance |
| AUC | area under the plasma concentration-time curve |
| $AUC_{0-10,am}$ | AUC from time zero (time of AM dosing) to 10 hours after the AM dose |
| $AUC_{0-14,pm}$ | AUC from time zero (time of PM dosing) to 14 hours after the PM dose |
| $AUC_{0-24}$ | AUC from time zero (time of AM dosing) to 24 hours after the AM dose |
| $AUC_{0-t,am}$ | AUC from time zero to the last time point with measurable drug concentration following AM dosing |
| $AUC_{0-t,pm}$ | AUC from time zero to the last time point with measurable drug concentration following PM dosing |
| Bid | twice daily |
| BQL | below the lower limit of quantification |
| CBC | complete blood count |
| CI | confidence interval |
| $C_{max,am}$ | maximum plasma concentration after the AM dose |
| $C_{max,pm}$ | maximum plasma concentration after the PM dose |
| CV | coefficient of variation |
| GCP | Good Clinical Practice |
| EC | enteric-coated |
| ECG | electrocardiogram |
| eCRF | electronic case report form |
| $E_{max}$ | maximal response or pharmacodynamic effect |
| GI | Gastrointestinal |
| GLSM | Geometric least-squares mean |
| HPLC/MS/MS | high pressure liquid chromatography tandem mass spectrometry |
| ITT | intent-to-treat |
| LLOQ | lower limit of quantification |
| LS | least square |
| MedDRA | Medical Dictionary for Regulatory Activities |
| MRM | multiple reaction monitoring |
| $\lambda_{z,am}$ | apparent first-order elimination rate constant following AM dosing |
| $\lambda_{z,pm}$ | apparent first-order elimination rate constant following PM dosing |
| Ln | natural log |
| PD | pharmacodynamic(s) |
| PDS | Phoenix Data Systems |
| PK | pharmacokinetic(s) |
| PP | per protocol |
| PPD | Pharmaceutical Product Development |
| PPI | proton pump inhibitor |
| QC | quality control |
| SD | standard deviation |
| SE | standard error |
| SOC | system organ class |
| SPE | solid phase extraction |
| $t_{lag,am}$ | time to the first measurable plasma concentration following the AM dose ($t_{lag,am}$) |
| $t_{lag,pm}$ | time to the first measurable plasma concentration following the PM dose ($t_{lag,am}$) |
| $t_{last}$ | last time point with measurable drug concentration |
| $t_{max}$ | time to maximum plasma concentration |
| $t_{1/2,am}$ | apparent plasma half-life following the AM dose |
| $t_{1/2,pm}$ | apparent plasma half-life following the PM dose |

The term "at risk patient" refers to patient(s) at risk for NSAID associated ulcer due to age or a documented history of gastric ulcers, or receiving concomitant LDA (low dose aspirin). In one embodiment, the at risk patient is a patient at risk for NSAID associated ulcer due to age greater than or equal to 50 years.

The term "pharmaceutically-acceptable", as employed herein, indicates the subject matter being identified as "pharmaceutically acceptable" is suitable and physiologically acceptable for administration to a patient/subject. For example, the term "pharmaceutically acceptable salt(s)" denotes suitable and physiologically acceptable salt(s).

The phrase "naproxen, or pharmaceutically acceptable salt thereof" refers to the free base of naproxen, pharmaceutically acceptable salt(s) of naproxen, and/or mixtures of the free base of naproxen and at least one pharmaceutically acceptable salt of naproxen.

The phrase "esomeprazole, or pharmaceutically acceptable salt thereof" refers to the free base of esomeprazole, pharmaceutically acceptable salt(s) of esomeprazole, and/or mixtures of the free base of esomeprazole and at least one pharmaceutically acceptable salt of esomeprazole.

The term "unit dosage form" (or "unit dose form") as used herein refers to a single entity for drug administration. For example, a single tablet or capsule containing both esomeprazole and naproxen is a unit dosage form. Unit dosage forms of the present disclosure provide for sequential drug release in a way that elevates gastric pH and reduces the deleterious effects of naproxen on the gastroduodenal mucosa, i.e., the esomeprazole is released first and the release of naproxen is delayed until after the pH in the GI tract has risen to 3.5 or greater. A "unit dosage form" (or "unit dose form") may also be referred to as a "fixed dosage form" (or "fixed dose form") or fixed dosage combination (or "fixed dose combination") and are otherwise interchangeable.

For the values provided herein, the term "about" indicates a given number may vary by at least 5%, with variations of 10%, 15% or 20% being possible.

With regard to the pharmacokinetic and/or pharmacodynamic values provided herein, the degree of variation is reflected in SDs and % CV values. The % CV=SD/mean× 100; the SD=(% CV×mean) divided by 100. It can be expected that approximately 68% of patients will be within one SD of the mean and approximately 95% of patients will be within two SDs of the mean. The pharmacokinetic and pharmacodynamic values presented herein are average values, rounded to the nearest whole number, and are based upon results obtained from multiple individuals. As a result, the values presented herein may vary from one patient to another. This variation is reflected in the term "about."

With regard to the dosages of each of naproxen, or pharmaceutically acceptable salt thereof and/or esomeprazole, or pharmaceutically acceptable salt thereof the term "about" is intended to reflect variations from the specifically identified dosages that are acceptable within the art.

With regard to time periods referred to herein, the term "about" is intended to reflect variations from the specifically identified time periods that are acceptable within the art.

With regard to the numerical % coefficient of variation values and/or ranges used herein, the term "about" is intended to reflect variations above and below the stated numerical value and/or range that that may achieve substantially the same results as the stated number.

With regard to the pH values and/or ranges recited herein, the term "about" is intended to to capture variations above and below the stated number that may achieve substantially the same results as the stated number.

With regard to the term numerical values used in conjunction with the phrase "substantially free", the term is intended to to capture variations above and below the stated number that may achieve substantially the same results as the stated number.

The phrase "substantially free" means from about 95% to about 99.99% free. In one embodiment, substantially free means about 95% free. In another embodiment, the term substantially free means about 96% free. In still another embodiment, the term substantially free means about 97% free. In yet another embodiment, the term substantially free means about 98% free. In a further embodiment, the term substantially free means about 99% free. In still a further embodiment, the term substantially free means about 99.99% free.

In the present disclosure, each of the variously stated ranges is intended to be continuous so as to include each numerical parameter between the stated minimum and maximum value of each range. For Example, a range of about 1 to about 4 includes about 1, 1, about 2, 2, about 3, 3, about 4, and 4.

One embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater to target: a mean % time at which intragastric pH remains at about 4.0 or greater for about a 24 hour period of at least about 41%.

In other embodiments, the mean % time at which intragastric pH remains at about 4.0 or greater for a 24 hour period is at least about 40%, about 45%, about 50%, about 55%, about 60%, about 65%, about 70%, about 71%, about 75%, about 77%, about 80%, about 85%, about 90%, or about 95%.

Another embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater to target: a mean % time at which intragastric pH remains at about 4.0 or greater for about a 24 hour period of at least about 41% and a pharmacokinetic (pk) profile having a mean maximum plasma concentration ($C_{max}$) for naproxen of at least 76 µg/ml with a % coefficient of variation ranging from 17-23.

A further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater to target: a mean % time at which intragastric pH remains at about 4.0 or greater for about a 24 hour period of at least about 41% and a pharmacokinetic (pk) profile having a mean maximum plasma concentration ($C_{max}$) for naproxen of about 76 µg/ml.

Yet another embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from 0 or greater to target: a mean % time at which intragastric pH remains at about 4.0 or greater for about a 24 hour period of at least about 41% and a pharmacokinetic (pk) profile having a mean area under the plasma concentration-time curve from time zero when first dose is administered to about 24 hours after the first dose is administered ($AUC_{0-24}$) for esomeprazole of at least 1500 hr*ng/mL with a % coefficient of variation ranging from 40-80.

Yet a further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from 0 or greater to target: a mean % time at which intragastric pH remains at about 4.0 or greater for about a 24 hour period of at least about 41% and a pharmacokinetic (pk) profile having a mean area under the plasma concentration-time curve from time zero when first dose is administered to about 24 hours after the first dose is administered ($AUC_{0-24}$) for esomeprazole of about 1500 hr*ng/mL.

Still yet another embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater to target: a mean % time at which intragastric pH remains at about 4.0 or greater for about a 24 hour period of at least about 41%; and a pharmacokinetic (pk) profile having a mean maximum plasma concentration ($C_{max}$) for naproxen of at least 76 µg/ml with a % coefficient of variation ranging from 17-23 and a mean area under the plasma concentration-time curve from time zero when first dose is administered to about 24 hours after the first dose is administered ($AUC_{0-24}$) for esomeprazole of at least 1500 hr*ng/mL with a % coefficient of variation ranging from 40-80.

Still even yet another embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater to target: a mean % time at which intragastric pH remains at about 4.0 or greater for about a 24 hour period of at least about 41%; and a pharmacokinetic (pk) profile having a mean maximum plasma concentration ($C_{max}$) for naproxen of about 76 µg/ml and a mean area under the plasma concentration-time curve from time zero when first dose is administered to about 24 hours after the first dose is administered ($AUC_{0-24}$) for esomeprazole of about 1500 hr*ng/mL.

A still even further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater to target: a pharmacokinetic (pk) profile having a mean maximum plasma concentration ($C_{max}$) for naproxen of at least 76 µg/ml with a % coefficient of variation ranging from 17-23.

Yet a further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater to target: a pharmacokinetic (pk) profile having a mean maximum plasma concentration ($C_{max}$) for naproxen of about 76 µg/ml.

A yet still further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater to target: and a pharmacokinetic (pk) profile having mean area under the plasma concentration-time curve from time zero when first dose is administered to about 24 hours after the first dose is administered ($AUC_{0-24}$) for esomeprazole of at least 1500 hr*ng/mL with a % coefficient of variation ranging from 40-80.

A yet even further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater to target: and a pharmacokinetic (pk) profile having mean area under the plasma concentration-time curve from time zero when first dose is administered to about 24 hours after the first dose is administered ($AUC_{0-24}$) for esomeprazole of about 1500 hr*ng/mL.

A further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
 i) a pk profile for naproxen where:
  a) the AM dose has a mean $C_{max}$ of at least 81 µg/ml with a % coefficient of variation ranging from 22-23 and a median time to maximum concentration ($T_{max}$) of from about 2.5 to about 4 hours, and b) the PM dose has a mean $C_{max}$ of at least 76.2 µg/ml with a % coefficient of variation ranging from 18-23 and a median $T_{max}$ of from about 10 to about 14 hours; and
ii) a pk profile for esomeprazole where:
  a) the AM dose has a mean area under the plasma concentration-time curve from time zero when the AM dose is administered to about 10 hours after the AM dose is administered ($AUC_{0-10,am}$) of at least 850 hr*ng/mL with a % coefficient of variation ranging from 45-70, and
  b) the PM dose has a mean area under the plasma concentration-time curve from time zero when the PM dose is administered to about 14 hours after the PM dose is administered ($AUC_{0-14,pm}$) of at least 650 hr*ng/mL with a % coefficient of variation ranging from 50-85.

A yet further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from 0 or greater, wherein one unit dose form is administered as an AM dose and a second dose administered about 10 hours later as a PM dose to target:
i) a pk profile for naproxen where:
  a) the AM dose has a mean $C_{max}$ of about 81 µg/ml and a median time to maximum concentration ($T_{max}$) of from about 2.5 to about 4 hours, and
  b) the PM dose has a mean $C_{max}$ of about 76.2 µg/ml and a median $T_{max}$ of from about 10 to about 14 hours; and
ii) a pk profile for esomeprazole where:
  a) the AM dose has a mean area under the plasma concentration-time curve from time zero when the AM dose is administered to about 10 hours after the AM dose is administered ($AUC_{0-10,am}$) of about 850 hr*ng/mL, and
  b) the PM dose has a mean area under the plasma concentration-time curve from time zero when the PM dose is administered to about 14 hours after the PM dose is administered ($AUC_{0-14,pm}$) of about 650 hr*ng/mL.

A still further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
i) a pk profile for naproxen where:
  a) the AM dose has a mean $C_{max}$ of at least 81 µg/ml with a % coefficient of variation ranging from 22-23 and a median time to maximum concentration ($T_{max}$) of from about 2.5 to about 4 hours, and
  b) the PM dose has a mean $C_{max}$ of at least 76.2 µg/ml with a % coefficient of variation ranging from 18-23 and a median $T_{max}$ of from about 10 to about 14 hours.

A yet still further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
i) a pk profile for naproxen where:
  a) the AM dose has a mean $C_{max}$ of about 81 µg/ml and a median time to maximum concentration ($T_{max}$) of from about 2.5 to about 4 hours, and
  b) the PM dose has a mean $C_{max}$ of about 76.2 µg/ml and a median $T_{max}$ of from about 10 to about 14 hours.

A yet even still further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
i) a pk profile for esomeprazole where:
  a) the AM dose has a mean area under the plasma concentration-time curve from time zero when the AM dose is administered to about 10 hours after the AM dose is administered ($AUC_{0-10,am}$) is at least 850 hr*ng/mL with a % coefficient of variation ranging from 45-70, and
  b) the PM dose has a mean area under the plasma concentration-time curve from time zero when the PM dose is administered to about 14 hours after the PM dose is administered ($AUC_{0-14,pm}$) is at least 650 hr*ng/mL with a % coefficient of variation ranging from 50-85.

A further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
i) a pk profile for esomeprazole where:
  a) the AM dose has a mean area under the plasma concentration-time curve from time zero when the AM dose is administered to about 10 hours after the AM dose is administered ($AUC_{0-10,am}$) is about 850 hr*ng/mL, and
  b) the PM dose has a mean area under the plasma concentration-time curve from time zero when the PM dose is administered to about 14 hours after the PM dose is administered ($AUC_{0-14,pm}$) of about 650 hr*ng/mL.

A yet still even further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
  i) a pk profile for naproxen where:
    a) the AM dose has a mean $C_{max}$ of at least 81 µg/ml with a % coefficient of variation ranging from 22-23 and a median time to maximum concentration ($T_{max}$) of from about 2.5 to about 4 hours, and
    b) the PM dose has a mean $C_{max}$ of at least 76.2 µg/ml with % coefficient of variation ranging from 18-23 and a median $T_{max}$ of from about 10 to about 14 hours;
  ii) a pk profile for esomeprazole where:
    a) the AM dose has a mean area under the plasma concentration-time curve from time zero when the AM dose is administered to about 10 hours after the AM dose is administered ($AUC_{0-10,am}$) is at least 850 hr*ng/mL with a % coefficient of variation ranging from 45-70, and
    b) the PM dose has a mean area under the plasma concentration-time curve from time zero when the PM dose is administered to about 14 hours after the PM dose is administered ($AUC_{0-14,pm}$) is at least 650 hr*ng/mL with a % coefficient of variation ranging from 50-85; and
  iii) a mean % time at which intragastric pH remains at about 4.0 or greater for about a 24 hour period of at least about 41%.

A still even further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
  i) a pk profile for naproxen where:
    a) the AM dose has a mean $C_{max}$ of about least 81 µg/ml and a median time to maximum concentration ($T_{max}$) of from about 2.5 to about 4 hours, and
    b) the PM dose has a mean $C_{max}$ of about 76.2 µg/ml and a median $T_{max}$ of from about 10 to about 14 hours;
  ii) a pk profile for esomeprazole where:
    a) the AM dose has a mean area under the plasma concentration-time curve from time zero when the AM dose is administered to about 10 hours after the AM dose is administered ($AUC_{0-10,am}$) of about 850 hr*ng/mL, and
    b) the PM dose has a mean area under the plasma concentration-time curve from time zero when the PM dose is administered to about 14 hours after the PM dose is administered ($AUC_{0-14,pm}$) of about 650 hr*ng/mL; and
  iii) a mean % time at which intragastric pH remains at about 4.0 or greater for about a 24 hour period of at least about 41%.

Still yet another embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
  i) a pk profile for naproxen where:
    a) the AM dose has a mean $C_{max}$ of at least 81 µg/ml with a % coefficient of variation ranging from 22-23 and a median time to maximum concentration ($T_{max}$) of from about 2.5 to about 4 hours, and
    b) the PM dose has a mean $C_{max}$ of at least 76.2 µg/ml with a % coefficient of variation ranging from 18-23 and a median $T_{max}$ of from about 10 to about 14 hours; and
  ii) a mean % time at which intragastric pH remains at about 4.0 or greater for about a 24 hour period of at least about 41%.

A still yet further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
  i) a pk profile for naproxen where:
    a) the AM dose has a mean $C_{max}$ of about 81 µg/ml and a median time to maximum concentration ($T_{max}$) of from about 2.5 to about 4 hours, and
    b) the PM dose has a mean $C_{max}$ of about 76.2 µg/ml and a median $T_{max}$ of from about 10 to about 14 hours; and
  ii) a mean % time at which intragastric pH remains at about 4.0 or greater for about a 24 hour period of at least about 41%.

Even still yet a further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole is released from said unit dose form at a pH of from 0 or greater, wherein one unit dose form is administered as an AM dose and a second dose administered about 10 hours later as a PM dose to target:
  i) a pk profile for esomeprazole where:
    a) the AM dose has a mean area under the plasma concentration-time curve from time zero when the AM dose is administered to about 10 hours after the AM dose is administered ($AUC_{0-10,am}$) is at least 850 hr*ng/mL with a % coefficient of variation ranging from 45-70, and
    b) the PM dose has a mean area under the plasma concentration-time curve from time zero when the PM dose is administered to about 14 hours after the PM dose is administered ($AUC_{0-14,pm}$) is at least 650 hr*ng/mL with a % coefficient of variation ranging from 50-85; and ii) a mean % time at which intragastric pH remains at about 4.0 or greater for about a 24 hour period of at least about 41%.

An even still further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole is released from said unit dose form at a pH of from 0 or greater, wherein one unit dose form is administered as an AM dose and a second dose administered about 10 hours later as a PM dose to target:
  i) a pk profile for esomeprazole where:
    a) the AM dose has a mean area under the plasma concentration-time curve from time zero when the AM dose is administered to about 10 hours after the AM dose is administered ($AUC_{0-10,am}$) of about 850 hr*ng/mL, and
    b) the PM dose has a mean area under the plasma concentration-time curve from time zero when the PM dose is administered to about 14 hours after the PM dose is administered ($AUC_{0-14,pm}$) of about 650 hr*ng/mL; and
  ii) a mean % time at which intragastric pH remains at about 4.0 or greater for about a 24 hour period of at least about 41%.

A yet still even further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
  i) a pk profile for naproxen where:
    a) the AM dose has a mean $C_{max}$ of at least 81 μg/ml with a % coefficient of variation ranging from 22-23 and a median time to maximum concentration ($T_{max}$) of from about 2.5 to about 4 hours, and
    b) the PM dose has a mean $C_{max}$ of at least 76.2 μg/ml with a % coefficient of variation of ranging from 18-23 and a median $T_{max}$ of from about 10 to about 14 hours;
  ii) a pk profile for esomeprazole where:
    a) the AM dose has a mean area under the plasma concentration-time curve from time zero when the AM dose is administered to 10 hours after the AM dose is administered ($AUC_{0-10,am}$) is at least 850 hr*ng/mL with a % coefficient of variation ranging from 45-70, and
    b) the PM dose has a mean area under the plasma concentration-time curve from time zero when the PM dose is administered to about 14 hours after the PM dose is administered ($AUC_{0-14,pm}$) is at least 650 hr*ng/mL with a % coefficient of variation ranging from 50-85;
  iii) a mean % time at which intragastric pH remains at about 4.0 or greater for about a 24 hour period of at least about 41%; and
  iv) a pharmacokinetic (pk) profile having a mean area under the plasma concentration-time curve from time zero when first dose is administered to about 24 hours after the first dose is administered ($AUC_{0-24}$) for esomeprazole of at least 1500 hr*ng/mL with a % coefficient of variation ranging from 40-80.

Another embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
  i) a pk profile for naproxen where:
    a) the AM dose has a mean $C_{max}$ of about least 81 μg/ml and a median time to maximum concentration ($T_{max}$) of from about 2.5 to about 4 hours, and
    b) the PM dose has a mean $C_{max}$ of about 76.2 μg/ml and a median $T_{max}$ of from about 10 to about 14 hours;
  ii) a pk profile for esomeprazole where:
    a) the AM dose has a mean area under the plasma concentration-time curve from time zero when the AM dose is administered to about 10 hours after the AM dose is administered ($AUC_{0-10,am}$) of about 850 hr*ng/mL, and
    b) the PM dose has a mean area under the plasma concentration-time curve from time zero when the PM dose is administered to about 14 hours after the PM dose is administered ($AUC_{0-14,pm}$) of about 650 hr*ng/mL;
  iii) a mean % time at which intragastric pH remains at about 4.0 or greater for a 24 hour period of at least about 41%; and
  iv) a pharmacokinetic (pk) profile having a mean area under the plasma concentration-time curve from time zero when first dose is administered to about 24 hours after the first dose is administered ($AUC_{0-24}$) for esomeprazole of about 1500 hr*ng/mL.

A further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
  i) a pk profile for naproxen where:
    a) the AM dose has a mean $C_{max}$ of at least 81 μg/ml with a % coefficient of variation ranging from 22-23 and a median time to maximum concentration ($T_{max}$) of from about 2.5 to about 4 hours, and
    b) the PM dose has a mean $C_{max}$ of at least 76.2 μg/ml with a % coefficient of variation ranging from 18-23 and a median $T_{max}$ of from about 10 to about 14 hours;
  ii) a pk profile for esomeprazole where:
    a) the AM dose has a mean area under the plasma concentration-time curve from time zero when the AM dose is administered to about 10 hours after the AM dose is administered ($AUC_{0-10,am}$) is at least 850 hr*ng/mL with a % coefficient of variation ranging from 45-70, and b) the PM dose has a mean area under the plasma concentration-time curve from time zero when the PM dose is administered to about 14 hours after the PM dose is administered ($AUC_{0-14,pm}$) is at least 650 hr*ng/mL with a % coefficient of variation ranging from 50-85; and iii) a pharmacokinetic (pk) profile having a mean area under the plasma concentration-time curve from time zero when first dose is administered to about 24 hours after the first dose is administered ($AUC_{0-24}$) for esomeprazole of at least 1500 hr*ng/mL with a % coefficient of variation ranging from 40-80.

A yet further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:

i) a pk profile for naproxen where:
  a) the AM dose has a mean $C_{max}$ of about 81 μg/ml and a median time to maximum concentration ($T_{max}$) of from about 2.5 to about 4 hours, and
  b) the PM dose has a mean $C_{max}$ of about 76.2 μg/ml and a median $T_{max}$ of from about 10 to about 14 hours;

ii) a pk profile for esomeprazole where:
  a) the AM dose has a mean area under the plasma concentration-time curve from time zero when the AM dose is administered to about 10 hours after the AM dose is administered ($AUC_{0-10,am}$) of about 850 hr*ng/mL, and
  b) the PM dose has a mean area under the plasma concentration-time curve from time zero when the PM dose is administered to about 14 hours after the PM dose is administered ($AUC_{0-14,pm}$) of about 650 hr*ng/mL; and iii) a pharmacokinetic (pk) profile having a mean area under the plasma concentration-time curve from time zero when first dose is administered to about 24 hours after the first dose is administered ($AUC_{0-24}$) for esomeprazole of about 1500 hr*ng/mL.

A still further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:

i) a pk profile for esomeprazole where:
  a) the AM dose has a mean area under the plasma concentration-time curve from time zero when the AM dose is administered to about 10 hours after the AM dose is administered ($AUC_{0-10,am}$) is at least 850 hr*ng/mL with a % coefficient of variation ranging from 45-70, and
  b) the PM dose has a mean area under the plasma concentration-time curve from time zero when the PM dose is administered to about 14 hours after the PM dose is administered ($AUC_{0-14,pm}$) is at least 650 hr*ng/mL with a % coefficient of variation ranging from 50-85; and ii) a pharmacokinetic (pk) profile having a mean area under the plasma concentration-time curve from time zero when first dose is administered to about 24 hours after the first dose is administered ($AUC_{0-24}$) for esomeprazole is at least 1500 hr*ng/mL with a % coefficient of variation ranging from 40-80.

Still a further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:

i) a pk profile for esomeprazole where:
  a) the AM dose has a mean area under the plasma concentration-time curve from time zero when the AM dose is administered to about 10 hours after the AM dose is administered ($AUC_{0-10,am}$) of about 850 hr*ng/mL, and
  b) the PM dose has a mean area under the plasma concentration-time curve from time zero when the PM dose is administered to about 14 hours after the PM dose is administered ($AUC_{0-14,pm}$) of about 650 hr*ng/mL; and ii) a pharmacokinetic (pk) profile having a mean area under the plasma concentration-time curve from time zero when first dose is administered to about 24 hours after the first dose is administered ($AUC_{0-24}$) for esomeprazole of about 1500 hr*ng/mL.

Yet another embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:

i) a pk profile for naproxen where:
  a) the AM dose has a mean $C_{max}$ of at least 81 μg/ml with a % coefficient of variation ranging from 22-23 and a median time to maximum concentration ($T_{max}$) of from about 2.5 to about 4 hours, and
  b) the PM dose has a mean $C_{max}$ of at least 76.2 μg/ml with a % coefficient of variation ranging from 18-23 and a median $T_{max}$ of from about 10 to about 14 hours; and ii) a pharmacokinetic (pk) profile having a mean area under the plasma concentration-time curve from time zero when first dose is administered to about 24 hours after the first dose is administered ($AUC_{0-24}$) for esomeprazole is at least 1500 hr*ng/mL with a % coefficient of variation ranging from 40-80.

Yet still another embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:

i) a pk profile for naproxen where:
 a) the AM dose has a mean $C_{max}$ of about 81 µg/ml and a median time to maximum concentration ($T_{max}$) of from about 2.5 to about 4 hours, and
 b) the PM dose has a mean $C_{max}$ of about 76.2 µg/ml and a median $T_{max}$ of from about 10 to about 14 hours; and
ii) a pharmacokinetic (pk) profile having a mean area under the plasma concentration-time curve from time zero when first dose is administered to about 24 hours after the first dose is administered ($AUC_{0-24}$) for esomeprazole of about 1500 hr*ng/mL.

Yet a further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:

i) a pk profile for esomeprazole where:
 a) the AM dose has a mean area under the plasma concentration-time curve from time zero when the AM dose is administered to about 10 hours after the AM dose is administered ($AUC_{0-10,am}$) is at least 850 hr*ng/mL with a % coefficient of variation ranging from 45-70, and
 b) the PM dose has a mean area under the plasma concentration-time curve from time zero when the PM dose is administered to about 14 hours after the PM dose is administered ($AUC_{0-14,pm}$) is at least 650 hr*ng/mL with a % coefficient of variation ranging from 50-85;
ii) a mean % time at which intragastric pH remains at about 4.0 or greater for about a 24 hour period of at least about 41%; and
iii) a pharmacokinetic (pk) profile having a mean area under the plasma concentration-time curve from time zero when first dose is administered to about 24 hours after the first dose is administered ($AUC_{0-24}$) for esomeprazole is at least 1500 hr*ng/mL with a % coefficient of variation ranging from 40-80.

Yet a still further embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:

i) a pk profile for esomeprazole where:
 a) the AM dose has a mean area under the plasma concentration-time curve from time zero when the AM dose is administered to about 10 hours after the AM dose is administered ($AUC_{0-10,am}$) of about 850 hr*ng/mL, and
 b) the PM dose has a mean area under the plasma concentration-time curve from time zero when the PM dose is administered to about 14 hours after the PM dose is administered ($AUC_{0-14,pm}$) of about 650 hr*ng/mL;
ii) a mean % time at which intragastric pH remains at about 4.0 or greater for about a 24 hour period of at least about 41%; and
iii) a pharmacokinetic (pk) profile having a mean area under the plasma concentration-time curve from time zero when first dose is administered to about 24 hours after the first dose is administered ($AUC_{0-24}$) for esomeprazole of about 1500 hr*ng/mL.

Yet another embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:

i) a pk profile for naproxen where:
 a) the AM dose has a mean $C_{max}$ of at least 81 µg/ml with a % coefficient of variation ranging from 22-23 and a median time to maximum concentration ($T_{max}$) of from about 2.5 to about 4 hours, and
 b) the PM dose has a mean $C_{max}$ of at least 76.2 µg/ml with a % coefficient of variation ranging from 18-23 and a median $T_{max}$ of from about 10 to about 14 hours;
ii) a mean % time at which intragastric pH remains at about 4.0 or greater for about a 24 hour period of at least about 41%; and
iii) a pharmacokinetic (pk) profile having a mean area under the plasma concentration-time curve from time zero when first dose is administered to about 24 hours after the first dose is administered ($AUC_{0-24}$) for esomeprazole is at least 1500 hr*ng/mL with a % coefficient of variation ranging from 40-80.

Yet still another embodiment is directed to a method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:

i) a pk profile for naproxen where:
 a) the AM dose has a mean $C_{max}$ of about 81 µg/ml and a median time to maximum concentration ($T_{max}$) of from about 2.5 to about 4 hours, and
 b) the PM dose has a mean $C_{max}$ of about 76.2 µg/ml and a median $T_{max}$ of from about 10 to about 14 hours;
ii) a mean % time at which intragastric pH remains at about 4.0 or greater for about a 24 hour period of at least about 41%; and iii) a pharmacokinetic (pk) profile having a mean area under the plasma concentration-time curve from time zero when first dose is administered to about 24 hours after the first dose is administered ($AUC_{0-24}$) for esomeprazole is about 1500 hr*ng/mL.

In another embodiment, naproxen can be present as the free base in an amount of from about 500 mg.

In still another embodiment, naproxen can be present as the free base in an amount of about 500 mg.

In yet another embodiment, naproxen can be present in equivalent amounts of pharmaceutically acceptable salts of naproxen, e.g., sodium naproxen.

In a further embodiment, esomeprazole can be present as a magnesium salt.

In an even further embodiment, esomeprazole, or pharmaceutically acceptable salt thereof, can be present in an amount to provide from about 10 mg to about 30 mg of esomeprazole.

In a further embodiment, esomeprazole, or pharmaceutically acceptable salt thereof, can be present in an amount to provide about 15 mg of esomeprazole.

In yet an even further embodiment, esomeprazole, or pharmaceutically acceptable salt thereof, can be present in an amount to provide about 20 mg of esomeprazole.

In still yet another embodiment, esomeprazole, or pharmaceutically acceptable salt thereof, can be present in an amount to provide about 30 mg of esomeprazole.

In still another embodiment, the mean % time at which intragastric pH remains at about 4.0 or greater for about a 24 hour period is at least about 60%.

In yet another embodiment, the mean % time at which intragastric pH remains at about 4.0 or greater for about a 24 hour period is at least about 71%.

In still yet an even further embodiment, the mean % time at which intragastric pH remains at about 4.0 or greater for about a 24 hour period is at least about 77%.

In an even still further embodiment, the mean maximum plasma concentration ($C_{max}$) for naproxen is at least 79 µg/ml with a % coefficient of variation ranging from 17-23.

In a further embodiment, the mean maximum plasma concentration ($C_{max}$) for naproxen is about 79 µg/ml.

In yet an even still further embodiment, the mean area under the plasma concentration-time curve from time zero when first dose is administered to about 24 hours after the first dose is administered ($AUC_{0-24}$) for esomeprazole is 2134 hr*ng/mL with a % coefficient of variation of 74.

In another embodiment, the mean area under the plasma concentration-time curve from time zero when first dose is administered to about 24 hours after the first dose is administered ($AUC_{0-24}$) for esomeprazole is about 2134 hr*ng/mL.

In yet another embodiment, the mean area under the plasma concentration-time curve from time zero when first dose is administered to about 24 hours after the first dose is administered ($AUC_{0-24}$) for esomeprazole is about 2000 hr*ng/mL with a % coefficient of variation ranging from 40-80.

In yet another embodiment, the mean area under the plasma concentration-time curve from time zero when first dose is administered to about 24 hours after the first dose is administered ($AUC_{0-24}$) for esomeprazole is about 2000 hr*ng/mL.

In still another embodiment, the mean area under the plasma concentration-time curve from time zero when first dose is administered to about 24 hours after the first dose is administered ($AUC_{0-24}$) for esomeprazole is about 1500 hr*ng/mL.

In a still further embodiment, the mean area under the plasma concentration-time curve from time zero when first dose is administered to about 24 hours after the first dose is administered ($AUC_{0-24}$) for esomeprazole is 4911 hr*ng/mL with a % coefficient of variation of 42.

In yet still a further embodiment, the mean area under the plasma concentration-time curve from time zero when first dose is administered to about 24 hours after the first dose is administered ($AUC_{0-24}$) for esomeprazole is about 4911 hr*ng/mL.

In one embodiment, the pharmaceutical composition in unit dose form comprises about 500 mg of said naproxen, or pharmaceutically acceptable salt thereof, and about 20mg of said esomeprazole, or pharmaceutically acceptable salt thereof.

In another embodiment, the pharmaceutical composition in unit dose form comprises about 500 mg of said naproxen, or pharmaceutically acceptable salt thereof, and about 30 mg of said esomeprazole, or pharmaceutically acceptable salt thereof.

In yet another embodiment, the unit dose form is administered twice a day for at least 6 days.

In still another embodiment, the unit dose form is administered twice a day for at least 9 days.

In still yet another embodiment, the patient in need thereof is an at risk patient.

In yet another embodiment, the at risk patient is being treated for a disease or disorder selected from pain and inflammation.

In a further embodiment, the at risk patient is being treated for osteoarthritis, rheumatoid arthritis, ankylosing spondylitis, or a combination thereof.

In another embodiment, the patient in need thereof is being treated for a disease or disorder selected from pain and inflammation.

In yet another embodiment, the patient in need thereof is being treated for osteoarthritis, rheumatoid arthritis, ankylosing spondylitis, or a combination thereof.

In yet another embodiment, the mean $C_{max}$ for said AM dose of naproxen is 86.2 µg/ml with a % coefficient of variation of 22 and said median $T_{max}$ is about 3.0 hours; and the mean $C_{max}$ for said PM dose is 76.8 µg/ml with a % coefficient of variation of 18 and said median $T_{max}$ is about 10 hours.

In another embodiment, the mean $C_{max}$ for said AM dose of naproxen is about 86.2 µg/ml and said median $T_{max}$ is about 3.0 hours; and the mean $C_{max}$ for said PM dose is about 76.8 µg/ml and said median $T_{max}$ is about 10 hours.

In still another embodiment, the mean $C_{max}$ for said AM dose of naproxen is 80.9 µg/ml with a % coefficient of variation of 23 and said median $T_{max}$ is about 3.0 hours; and b) the mean $C_{max}$ for said PM dose is 76.2 µg/ml with a % coefficient of variation of 23 and said median $T_{max}$ is about 10.4 hours.

In still yet another embodiment, the mean $C_{max}$ for said AM dose of naproxen is about 80.9 µg/ml and said median $T_{max}$ is about 3.0 hours; and b) the mean $C_{max}$ for said PM dose is about 76.2 µg/ml and said median $T_{max}$ is about 10.4 hours.

In yet still another embodiment, the mean area under the plasma concentration-time curve from time zero when the AM dose is administered to about 10 hours after the AM dose is administered ($AUC_{0-10,am}$) for said AM dose of esomeprazole is 1216 hr*ng/mL with a % coefficient of variation of 69, and the mean area under the plasma concentration-time curve from time zero when the PM dose is administered to about 14 hours after the PM dose is administered ($AUC_{0-14,pm}$) for said PM dose of esomeprazole is 919 hr*ng/mL with a % coefficient of variation of 84.

In a further embodiment, the PM dose has a mean area under the plasma concentration-time curve from time zero when the PM dose is administered to about 14 hours after the PM dose is administered ($AUC_{0-14,pm}$) is at least 900 hr*ng/mL with a % coefficient of variation ranging from 50-85.

In a still further embodiment, the PM dose has a mean area under the plasma concentration-time curve from time zero when the PM dose is administered to about 14 hours after the PM dose is administered ($AUC_{0-14,pm}$) of about 900 hr*ng/mL.

In a still even further embodiment, the PM dose has a mean area under the plasma concentration-time curve from time zero when the PM dose is administered to about 14 hours after the PM dose is administered ($AUC_{0-14,pm}$) of about 2100 hr*ng/mL.

In yet another embodiment, the mean area under the plasma concentration-time curve from time zero when the AM dose is administered to about 10 hours after the AM dose is administered ($AUC_{0-10,am}$) for said AM dose of esomeprazole is about 1216 hr*ng/mL, and the mean area under the plasma concentration-time curve from time zero when the PM dose is administered to about 14 hours after the PM dose is administered ($AUC_{0-14,pm}$) for said PM dose of esomeprazole is about 919 hr*ng/mL.

In an even further embodiment, the AM dose has a mean area under the plasma concentration-time curve from time zero when the AM dose is administered to about 10 hours after the AM dose is administered ($AUC_{0-10,am}$) is at least 1200 hr*ng/mL with a % coefficient of variation ranging from 45-70.

In a still even further embodiment, the AM dose has a mean area under the plasma concentration-time curve from time zero when the AM dose is administered to about 10 hours after the AM dose is administered ($AUC_{0-10,am}$) of about 1200 hr*ng/mL.

In a till even further embodiment, the AM dose has a mean area under the plasma concentration-time curve from time zero when the AM dose is administered to about 10 hours after the AM dose is administered ($AUC_{0-10,am}$) of about 2800 hr*ng/mL.

In still yet a further embodiment, the mean area under the plasma concentration-time curve from time zero when the AM dose is administered to about 10 hours after the AM dose is administered ($AUC_{0-10,am}$) for said AM dose of esomeprazole is 2779 hr*ng/mL with a % coefficient of variation of 45, and the mean area under the plasma concentration-time curve from time zero when the PM dose is administered to about 14 hours after the PM dose is administered ($AUC_{0-14,pm}$) for said PM dose of esomeprazole is 2066 hr*ng/mL with a % coefficient of variation of 53.

In an even further embodiment, the mean area under the plasma concentration-time curve from time zero when the AM dose is administered to about 10 hours after the AM dose is administered ($AUC_{0-10,am}$) for said AM dose of esomeprazole is about 2779 hr*ng/mL, and the mean area under the plasma concentration-time curve from time zero when the PM dose is administered to about 14 hours after the PM dose is administered ($AUC_{0-14,pm}$) for said PM dose of esomeprazole is about 2066 hr*ng/mL.

In an even further embodiment, the pharmaceutical composition in unit dose form is a multilayer tablet comprising at least one core and at least a first layer and a second layer, wherein said core comprises naproxen, or pharmaceutically acceptable salt thereof; said first layer is a coating that at least begins to release the naproxen, or pharmaceutically acceptable salt thereof, when the pH of the surrounding medium of about 3.5 or greater; said second layer is esomeprazole, or pharmaceutically acceptable salt thereof, wherein said esomeprazole, or pharmaceutically acceptable salt thereof, is released at a pH of from about 0 or greater.

In an even further embodiment, esomeprazole, or pharmaceutically acceptable salt thereof, is released at a pH of from 0 or greater.

In another embodiment, esomeprazole, or pharmaceutically acceptable salt thereof, is released at a pH of from about 1 or greater.

In a further embodiment, esomeprazole, or pharmaceutically acceptable salt thereof, is released at a pH of from 1 or greater.

In still another embodiment, esomeprazole, or pharmaceutically acceptable salt thereof, is released at a pH of from about 0 to about 2.

In yet a further embodiment, esomeprazole, or pharmaceutically acceptable salt thereof, is released at a pH of from 0 to 2.

In yet still another embodiment, at least a portion of said esomeprazole, or pharmaceutically acceptable salt thereof, is not coated with an enteric coating.

In even yet still another embodiment, the first layer is an enteric coating.

In an even further embodiment, the pharmaceutical composition in unit dose form is a multilayer tablet comprising a core comprising naproxen, or pharmaceutically acceptable salt thereof, and a first layer comprising a coating that at least begins releasing the naproxen when the pH of the surrounding medium is about 3.5 or greater and a second layer comprising esomeprazole, or pharmaceutically acceptable salt thereof, wherein at least a portion of said esomeprazole, or pharmaceutically acceptable salt thereof, is not surrounded by an enteric coating.

In another embodiment, the first layer is a coating that at least begins to release the naproxen when the pH of the surrounding medium is about 4.0, 4.5, 5.0 or greater.

In still yet another embodiment, said first layer begins to release the naproxen when the pH of the surrounding medium is at about 4.0 or greater.

In a further embodiment, said first layer begins to release the naproxen when the pH of the surrounding medium is at about 4.5 or greater.

In yet a further embodiment, said first layer begins to release the naproxen when the pH of the surrounding medium is at about 5.0 or greater.

In one embodiment, at least about 95% of the esomeprazole, or pharmaceutically acceptable salt thereof, is not surrounded by an enteric coating.

In another embodiment, at least about 99% of the esomeprazole, or pharmaceutically acceptable salt thereof, is not surrounded by an enteric coating. In yet another embodiment, at least about 99.5% of the esomeprazole, or pharmaceutically acceptable salt thereof, is not surrounded by an enteric coating.

In yet another embodiment, the multilayer tablet is substantially free of sodium bicarbonate.

In still another embodiment, the multilayer tablet is completely (i.e., 100%) free of sodium bicarbonate.

In one embodiment, the dosing regimen is twice a day.

In another embodiment, the doses can be separated by a period of at least about 10 hours.

In another embodiment, the pharmaceutical composition in unit dose form is given about 1 hour before a patient ingests a meal.

In another embodiment, the pharmaceutical compositions of the present disclosure may be administered therapeutically to patients either short term or over a longer period of time, for example chronically.

In other embodiments, long term or chronic administration of the pharmaceutical compositions disclosed herein can result in intragastric pH being at least about 4.0 or greater a higher percentage of time per 24 hour period versus short-term administration. For example, administration of certain pharmaceutical compositions may result in a higher percentage time of intragastric pH being greater than about 4.0 on Day 9 versus Day 1 of treatment.

In another embodiment, the method for delivering a pharmaceutical composition to a patient in need thereof, comprises administering to the patient a pharmaceutical composition in unit dose form comprising naproxen, or pharmaceutically acceptable salt thereof, and esomeprazole, or pharmaceutically acceptable salt thereof, wherein intragastric pH is increased to at least about 4.0 within one hour of administration.

In another embodiment, intragastric pH is increased to at least about 4.0 or greater within 30 or 45 minutes of administration The pharmaceutical compositions disclosed herein include, but are not limited to, for example, tablets and capsules that can be made in accordance with methods that are standard in the art (see, e.g., *Remington's Pharmaceutical Sciences*, 16$^{th}$ ed., A Oslo editor, Easton, Pa. (1980)).

Suitable carriers include, but are not limited to: water; salt solutions; alcohols; gum arabic; vegetable oils; benzyl alcohols; polyethylene glycols; gelatin; carbohydrates such as lactose, amylose or starch; magnesium stearate; talc; silicic acid; paraffin; perfume oil; fatty acid esters; hydroxymethylcellulose; polyvinyl pyrrolidone; etc.

The pharmaceutical compositions disclosed herein can be sterilized and, if desired, mixed with, for example, auxiliary agents, such as, for example, preservatives; stabilizers; buffers; coloring agents; and flavoring agents.

In one embodiment, at least one of the layers comprising the pharmaceutical compositions disclosed herein may be applied using standard coating techniques. The layer materials may be dissolved or dispersed in organic or aqueous solvents. The layer materials may include, but are not limited to, for example, one or more of the following materials: methacrylic acid copolymers, shellac, hydroxypropylmethcellulose phthalate, polyvinyl acetate phthalate, hydroxypropylmethyl-cellulose trimellitate, carboxymethylethyl-cellulose, cellulose acetate phthalate, and/or other suitable polymer(s). The pH at which the first layer dissolves can be controlled by the polymer or combination of polymers selected and/or ratio of pendant groups. For example, dissolution characteristics of the polymer film can be altered by the ratio of free carboxyl groups to ester groups. The layers may also contain pharmaceutically acceptable plasticizers, such as, for example, triethyl citrate, dibutyl phthalate, triacetin, polyethylene glycols, polysorbates or other plasticizers. Additives, such as, for example, dispersants, colorants, anti-adhering, and anti-foaming agents may also be used.

In one embodiment, the pharmaceutical compositions disclosed herein can be in the form of a bi- or multi-layer tablet. In a bi-layer tablet, one portion/layer of the tablet contains the esomeprazole, or pharmaceutically acceptable salt thereof, in the required dose along with appropriate excipients, agents to aid dissolution, lubricants, fillers, etc.; and a second portion/layer of the tablet contains the NSAID in the required dose along with other excipients, dissolution agents, lubricants, fillers, etc.

In another embodiment, the naproxen portion/layer is surrounded by a polymeric coating that dissolves at a pH of at least about 3.5 or greater.

In yet another embodiment, the naproxen portion/layer is surrounded by a polymeric coating that dissolves at a pH of at least about 4 or greater.

The naproxen, or pharmaceutically acceptable salt thereof, may be granulated by methods such as slugging, low- or high-shear granulation, wet granulation, or fluidized-bed granulation. Of these processes, slugging generally produces tablets of less hardness and greater friability. Low-shear granulation, high-shear granulation, wet granulation and fluidized-bed granulation generally produce harder, less friable tablets.

EXAMPLE(S)

The invention is further defined in the following Example(s). It should be understood the Example(s) are given by way of illustration only. From the above discussion and the Example(s), one skilled in the art can ascertain the essential characteristics of the invention, and without departing from the spirit and scope thereof, can make various changes and modifications to adapt the invention to various uses and conditions. As a result, the invention is not limited by the illustrative example(s) set forth hereinbelow, but rather defined by the claims appended hereto.

Example 1

A randomized, open-label, 4-way cross-over study to evaluate the effect on days 1 and 9 of twice daily oral administration of three PN 400 formulations (enteric coated naproxen 500 mg combined with non-enteric coated esomeprazole 10, 20, or 30 mg) versus the effect of twice daily oral administration of a separate 500 mg non-enteric coated naproxen tablet and once daily oral administration of a separate EC esomeprazole (20 mg) capsule (Nexium® 20mg capsule) on the 24-hour intragastric pH and pharmacokinetic parameters (i.e., $C_{max}$, $T_{max}$, $AUC_{0-10,am}$, $AUC_{0-14,pm}$, $AUC_{0-24}$, $AUC_{0-t,am}$, and $AUC_{0-t,pm}$) of healthy volunteers. The PN400 tablet is a multilayer tablet comprising an inner core of naproxen surrounded by a first layer comprising an enteric coating and a second layer comprising non-enteric coated esomeprazole.

The study was designed to compare the pharmacodynamic (PD) measurements of intragastric pH (percent time of pH>4.0) on Day 9 of three PN 400 formulations following twice daily (BID) administration versus a combination of non-enteric coated naproxen taken BID and EC esomeprazole (20 mg) taken once daily.

The study was also designed to compare the PD measurement of intragastric pH (percent time of pH>4.0) on Day 1 of three PN 400 formulations following BID administration versus a combination of non-enteric coated naproxen taken BID and EC esomeprazole taken once daily; and assess the pharmacokinetics of esomeprazole and naproxen on Day 1 and Day 9 in each of the treatment groups.

This was a single-center study in 28 healthy adults. The study consisted of four 9-day treatment periods. The first, second and third treatment periods were followed by a washout period of at least 12 days. Eligible subjects reported to the Phase 1 unit in the PM of Day 0 for screening.

Screening procedures included procurement of informed consent, medical and drug history, physical examination, vital signs, 12-lead electrocardiogram (ECG), clinical laboratory testing, urine drug screen, pregnancy test for females of childbearing potential, and helicobacter pylori breath test. Clinical laboratory tests, physical examination, and measurement of vital signs were performed at Screening and the Final Visit. A 12-lead electrocardiogram (ECG) and 13C-urea breath test to screen for possible helicobacter pylori infection were performed at Screening. A urine drug screen for all subjects and a urine pregnancy test for women of childbearing potential were performed on Days 0 and 8 of each treatment period. On Days 1 and 9 of each treatment period, 24-hour blood sampling was performed for pharmacokinetic (PK) assessments. Subjects were instructed to report to the Phase 1 unit within 14 days of the initiation of screening procedures.

28 subjects were planned, randomized and treated, and data for 25 subjects were analyzed as the Per-Protocol (PP) population; the Intent-to-Treat (ITT), Safety and PK populations included all 28 subjects. Subjects were healthy males or non-lactating, non-pregnant females 18 to 55 years of age with a body mass index of 19-32 kg/m², were helicobacter pylori (H. pylori) negative, and were generally in good health with no history of peptic ulcer disease or other acid-related gastrointestinal (GI) symptoms.

Subject enrollment and disposition are summarized in Table 2. Twenty-eight subjects were randomized and treated at one investigational center; these subjects comprised the PK population. One subject dropped out of the study for personal reasons after completing 3 treatment periods (Treatments A [PN 400/E30], B [PN 400/E20] and D [EC E20+naproxen]). The PP population included 25 subjects.

TABLE 2

Subject Enrollment and Disposition - All Subjects

|  | Subjects (%) N = 28 |
| --- | --- |
| Subjects Randomized and Treated | 28 (100) |
| Safety Population | 28 (100) |
| Intent-to-Treat Population | 28 (100) |
| Per Protocol Population | 25 (89) |
| PK Population | 28 (100) |
| Subjects Completed | 27 (96) |
| Subjects Withdrawn Prematurely | 1 (4) |
| Adverse event | 0 |
| Withdrew consent | 0 |
| Lost to follow-up | 0 |
| Other | 1 (4) |

The demographic characteristics of the ITT population at Screening are summarized in Table 3. The study population was 68% male and had a mean age of approximately 25 years. All subjects were white and non-Hispanic.

TABLE 3

Demographic Characteristics - ITT Population

|  | Total Subjects N = 28 |
| --- | --- |
| Age (years) |  |
| n | 28 |
| Mean (SD) | 24.9 (3.9) |
| Median | 24 |
| Range | 18-34 |
| Gender - n (%) |  |
| Males | 19 (68) |
| Females | 9 (32) |
| Race - n (%) |  |
| White | 28 (100) |
| Black/African American | 0 |
| Asian | 0 |
| Other | 0 |
| Ethnicity - n (%) |  |
| Hispanic or Latino | 0 |
| Not Hispanic or Latino | 28 (100) |
| Height (in) |  |
| n | 28 |
| Mean (SD) | 70.1 (4.1) |
| Median | 70.0 |
| Range | 63-79 |
| Weight (lb) |  |
| n | 28 |
| Mean (SD) | 177.9 (34.6) |
| Median | 178.0 |
| Range | 112-250 |

At any time during Screening but at least prior to Day 1 of the first treatment period, subjects had their lower esophageal sphincter (LES) located to determine accurate placement of the pH probe.

Subjects were randomized on Day 1 of the first treatment period into 1 of 4 dosing sequences to receive a 9-day course of each one of the following daily treatment regimens in a crossover fashion:

Treatment A: 1 tablet PN 400/E30 (EC naproxen 500 mg and non-EC esomeprazole 30 mg) BID.

Treatment B: 1 tablet PN 400/E20 (EC naproxen 500 mg and non-EC esomeprazole 20 mg) BID.

Treatment C: 1 tablet PN 400/E10 (EC naproxen 500 mg and non-EC esomeprazole 10 mg) BID.

Treatment D: EC E20+naproxen (1 tablet non-EC naproxen 500 mg and 1 capsule EC esomeprazole 20 mg in the AM and 1 tablet non-EC naproxen 500 mg in the PM)

All treatments were administered by study personnel 60 minutes prior to meals (i.e. doses were taken 60 minutes prior to breakfast (after an over night fast, for the AM dose) and/or 60 minutes prior to dinner (for the PM dose) for 9 days). The study medications administered BID were administered approximately 10 hours apart. Prior to administration of the Day 1 AM dose of study drug, the pH probe was placed to monitor intragastric pH for a period of 24 hours. The distal electrode was placed 10 cm below the LES with the proximal electrode placed 5 cm above the LES using the LES locator and/or by use of formal esophageal manometry by the investigator. The position of the distance of the electrode from the nostrils was recorded to facilitate the 24-hour intragastric pH assessments.

In addition, a pre-AM dose blood sample was collected. Post-AM dose blood samples were drawn approximately: 10, 20, 30 and 45 minutes and 1, 1.5, 2, 2.5, 3, 4, 6, 8, 10 (pre-PM dose blood sample), 10.17, 10.33, 10.5, 10.75, 11, 11.5, 12, 12.5, 13, 14, 16, 18, 20 and 24 hours for PK assessments. After AM dosing on Day 2, subjects were discharged from the Phase 1 unit and instructed to return for the next dosing in the PM of Day 2 and on Days 3-8 to receive the AM and PM doses. Subjects were confined to the Phase 1 unit in the PM of Day 8 in preparation for the 24-hour PK and pH assessments on Day 9. Monitoring of pH and blood sample collection on Day 9 was as described above for Day 1. The pH probe was removed in the AM on Day 10. Final PK samples were collected in the AM of Day 10.

Subjects were instructed to return to the Phase 1 unit for subsequent treatment periods and reminded of the timing for the next treatment period (i.e., the wash-out period of at least 12 days between treatments). In each subsequent treatment period, the same procedures were performed as during the first period, and final study procedures were performed on Day 10 of the last treatment period or whenever a subject discontinued from the study.

The PK measurements used in this study are assessments commonly used in Phase I studies.

Measuring Intragatric pH

The procedure used to measuring intragastric pH is standard commonly used in assessing the pharmacodynamic effect of acid-suppressing drugs. A Medtronics Digitrapper pH data logger (Medtronics, Minneapolis, Minn.) was used to record pH. The 24-hour pH assessments were performed on Days 1 and 9. The pH recording system measured the difference in potential between the recording and reference electrodes in the tip of the probe and stored this value every couple of seconds. The pH data was provided to a third party blinded to the assigned treatment groups. The third party evaluated the data to determine the validity of the pH recordings based on the following established criteria: At least 20 hours of valid pH data within a pre-specified reference range; No technical failures of the pH recording; and Less than 1 continuous hour with pH data outside the reference range.

Collection of Samples

PK blood samples were collected in 6 mL sodium heparin VACUTAINER tubes and stored on ice until centrifuged within 30 minutes of sample draw for approximately 10 minutes at 3000 rpm (approximately 1800×g) in a refrigerated centrifuge maintained at approximately 4° C. Plasma supernatant was withdrawn and frozen at −20° C. or colder within 60 minutes of collection. Samples were divided into 2 equal aliquots, with 1 tube being used for naproxen analysis and the other for esomeprazole analysis. Samples were kept frozen at −20° C. and shipped overnight to PPD Development, Richmond Va. for analysis at the end of the study.

Analysis of Esomeprazole in Plasma Assay Methods

Esomeprazole is optically stable and the degree of conversion from the S to the R enantiomer in humans is negligible. Thus sample analysis for esomeprazole was performed using the validated high performance liquid chromatography tandem mass spectrometry (HPLC/MS/MS) method for omeprazole. This method was developed and validated by PPD Development, Richmond, Va.

Assay methods were generally performed as essentially described hereinbelow:

A 100 µL aliquot of human plasma containing the anticoagulant (sodium heparin) and the analytes was fortified with the internal standard (deuterated analog of omeprazole). The analytes were isolated by solid phase extraction (SPE) using a Phenomenex Strata-X (10 mg) 96-well SPE plate. The final extract was analyzed by HPLC with MS/MS detection using a Micromass Quattro Micro, triple quadrupole instrument. Chromatographic retention and separation of the analytes were obtained on Betasil Silica-100 analytical column (3×50 mm, 5 µm particle size) using a gradient mobile phase program. Mobile phase A consisted of 0.1% formic acid in acetonitrile and mobile phase B consisted of 0.1% formic acid. The analytes were detected by MS/MS with positive electrospray ionization in the mode of multiple reaction monitoring (MRM), with ions monitored for omeprazole (m/z 346→198) and deuterated omeprazole (m/z 349→198).

Quantification was by analyte to internal standard peak area ratio. The linear range of quantitation was 1 to 1000 ng/mL in human plasma, with a lower limit of quantification (LLOQ) of 1 ng/mL. The assay was validated in terms of specificity, precision, accuracy, and sample stability.

Assay Performance

A set of 8 calibration standards ranging from 1.00 to 1000 ng/mL and quality control (QC) samples at 5 different concentrations (2.60, 8.00, 30.0, 130, and 750 ng/mL) of each analyte were prepared and stored at −20° C. Between-batch precision and accuracy for analysis of the QC samples were determined from batch analyses of clinical samples in this study. Precision was measured as the percent coefficient of variation (% CV) of the set of values obtained for each QC level. Accuracy was expressed as the percent difference of the mean value from the theoretical concentration at each QC level.

The inter-assay CV of the QCs for the omeprazole runs ranged from 3.44% to 5.88%, with mean percent differences from theoretical ranging from 0.329% to 1.80%. The differences of back-calculated calibration curve values from nominal values ranged from −2.87% to 1.54%. For the analytical runs, which contained diluted subject samples, the appropriate level quality control pool was diluted and analyzed in a similar manner to validate the dilution of study samples. The % CV of the diluted QCs for the run ranged from 0.599% to 2.74% with mean percent differences from theoretical ranging from −1.24% to 3.99%.

Analysis of Naproxen in Plasma Assay Methods

Concentrations of naproxen in human plasma were generally determined essentially as described hereinbelow using a validated HPLC method with fluorescence detection developed and validated at PPD Development, Richmond, VA.

A 100 µL aliquot of human plasma containing sodium heparin and the analytes was combined with the internal standard solution (2-naphthylacetic acid) and diluted with potassium chloride. The analyte and the internal standard were isolated using liquid-liquid extraction. Chromatographic retention and separation of the analytes was obtained on a Symmetry C18 column (4.6×150 mm, 5 µm particle size) using an isocratic mobile phase consisting of 45% acetonitrile: 55% 14.8 mM phosphate buffer. The analytes were detected by fluorescence using excitation and emission wavelengths of 230 nm and 370 nm, respectively.

Quantification was by analyte to internal standard peak height ratio. The nominal range of the method was 0.10 to 100 µg/mL for naproxen in human plasma with an LLOQ of 0.10 µg/mL.

Assay Performance

A set of 8 calibration standards ranging from 0.1 to 100 µg/mL and QC samples at 5 different concentrations (0.28, 0.80, 3.0, 12.0 and 76.0 µg/mL) of the analyte were prepared and stored at −20° C. Between-batch precision and accuracy for analysis of the QC samples were determined from batch analyses of clinical samples in this study. Precision was measured as the % CV of the set of values obtained for each QC level. Accuracy was expressed as the percent difference of the mean value from the theoretical concentration at each QC level.

The inter-assay CV of the QCs for the naproxen runs ranged from 2.22% to 9.59%, with mean percent differences from theoretical ranging from −3.59% to 0.933%. The differences of back-calculated calibration curve values from nominal values ranged from −4.73% to 3.79%. For the analytical run that contained diluted subject samples, the appropriate level of QC samples was diluted and analyzed in a similar manner to validate the dilution of study samples. The % CV of the diluted QCs for the run was 4.12% with a mean percent difference from theoretical of −1.54%.

Statistics and Analysis

Data were summarized by reporting the frequency and percentage of subjects in each category for categorical and ordinal measures, and means, standard deviation or standard error, medians, and ranges for continuous measures. All statistical analyses and data listings were completed using the SAS® system, version 8.2 or higher.

Three analysis populations were used for analysis:

1) Intent-to-Treat (ITT) population: all randomized subjects who had valid pH data for at least 1 treatment period. A subject was considered to have valid pH data for each treatment period if the subject received all doses of study medication per protocol, had at least 20 hours of valid pH data determined by the clinical investigator, did not have technical failures of the pH recording, and did not have one continuous hour or more with pH data outside the reference range.

2) Per-Protocol (PP) population: all ITT subjects who had valid pH data for all four treatment periods and did not violate the protocol in a way that would have significantly impacted the evaluation of PD endpoints.

3) PK population: all randomized subjects who received all doses of study medication for at least one treatment period and had adequate blood sampling to determine the PK parameters of the study drugs.

Pharmacodynamic Endpoints

For each Digitrapper session, separate plots of the esophageal and intragastric pH readings for each subject were prepared and reviewed for non-valid pH data. Particular attention was paid to recorded pH values that were outside the range from 0.6 to 8.0. Values considered by the investigator to be unlikely to have occurred due to a reasonable expectation of method variability, and which persisted to such an extent as to suggest possible transient unreliability of the equipment, were identified and excised from the database. Other apparent 'flat-lining' of the pH readings could also result in a determination of non-valid data.

The PD endpoints were summarized by treatment and analyzed by Analysis of Variance (ANOVA). The ANOVA model included sequence, period, and treatment as fixed effects, and subject within sequence as a random effect. The least square (LS) means for each treatment, the difference of LS means between each of the PN 400 treatments and the active control, and 95% confidence intervals (CIs) for all treatment differences were calculated. Both ITT and PP populations were used for the PD analysis. The PP population was the primary analysis population. In addition, the percent time of pH>3.0 and >5.0 on Days 1 and 9 was analyzed in a similar fashion as the percent time of pH>4.0. Mean pH data over 24 hours on Days 1 and 9 were plotted by treatment.

From a previous study, the within-subject standard deviation (SD) of percent time of pH>4.0 was 10%. The current study planned to enroll 28 subjects with the aim to have 24 evaluable subjects for analysis. A total of 24 subjects provides 80% power to reject the null hypothesis that the difference between each of the PN 400 treatments and the active control in percent time of pH>4.0 over 24 hours is ≤−8% using a pairwise t-test with a one-sided significance level of 0.05.

Primary Pharmacodynamic Endpoint: Percent Time Intragastric pH>4.0 on Day 9

Results from Day 9 are set forth in Table 4. On Day 9, both PN 400/E30 and PN 400/E20 treatments resulted in a greater percent time with intragastric pH>4.0 than treatment with EC E20+naproxen. PN 400/E10 had the lowest percent time with intragastric pH>4.0 and was also the most variable treatment as evidenced by the high % CV in Table 4.

TABLE 4

Percent Time of pH Greater than 4.0-Day 9-Per-Protocol Population

| | A<br>PN 400/E30<br>N = 25 | B<br>PN 400/E20<br>N = 25 | C<br>PN 400/E10<br>N = 25 | D<br>EC E20 +<br>naproxen<br>N = 25 |
|---|---|---|---|---|
| % Time of pH >4.0 | | | | |
| Mean (SD) | 76.50 (12.26) | 71.35 (13.01) | 40.85 (22.51) | 56.85 (10.06) |
| Median | 78.79 | 70.42 | 35.76 | 55.14 |
| % Coefficient of variation | 16 | 18 | 55 | 18 |
| Range | 49.79-95.32 | 51.76-97.61 | 10.30-85.26 | 40.63-75.51 |
| LS Mean (SD) | 76.75 (3.02) | 71.46 (3.02) | 41.09 (3.02) | 57.23 (3.02) |

TABLE 4-continued

Percent Time of pH Greater than 4.0-Day 9-Per-Protocol Population

|  | A<br>PN 400/E30<br>N = 25 | B<br>PN 400/E20<br>N = 25 | C<br>PN 400/E10<br>N = 25 | D<br>EC E20 +<br>naproxen<br>N = 25 |
|---|---|---|---|---|
|  | A vs. D | B vs. D | C vs. D |  |
| LS Mean Difference (SE) | 19.52 (3.25) | 14.23 (3.25) | −16.14 (3.25) | — |
| 95% Confidence Interval | 13.04-26.01 | 7.75-20.71 | −22.26--9.66 | — |

On Day 1, the LS mean percent time intragastric pH>4.0 ranged from 13% with PN 400/E10 to 28% with PN 400/E30. Treatment differences compared to EC E20+naproxen were small. Only PN 400/E30 (28%) had a statistically significant, greater percent time with pH>4.0 compared to EC E20+naproxen (21%).

As shown in FIG. 1, there were three increases in pH throughout the day which were associated with food intake at 1, 6 and 11 hours, for breakfast, lunch and dinner, respectively. These increases in pH occurred approximately one hour after each meal for all treatments. Following the AM dose of PN 400 on Day 9, the pH increase occurred approximately one hour earlier than the food induced increase in pH (see also FIG. 2). After the AM dose of EC E20+naproxen, the pH increase occurred at least 30 minutes later than PN 400.

The overall pH profiles on Day 9 showed an esomeprazole dose-related effect on intragastric pH beyond the influence of food intake. The effect on intragastric pH profiles was similar between PN 400/E30 and PN 400/E20, with each of these treatments reflecting a slower return of gastric contents to lower pH levels after food intake than either the PN400/E10 or EC E20+naproxen treatments.

Figure 2:
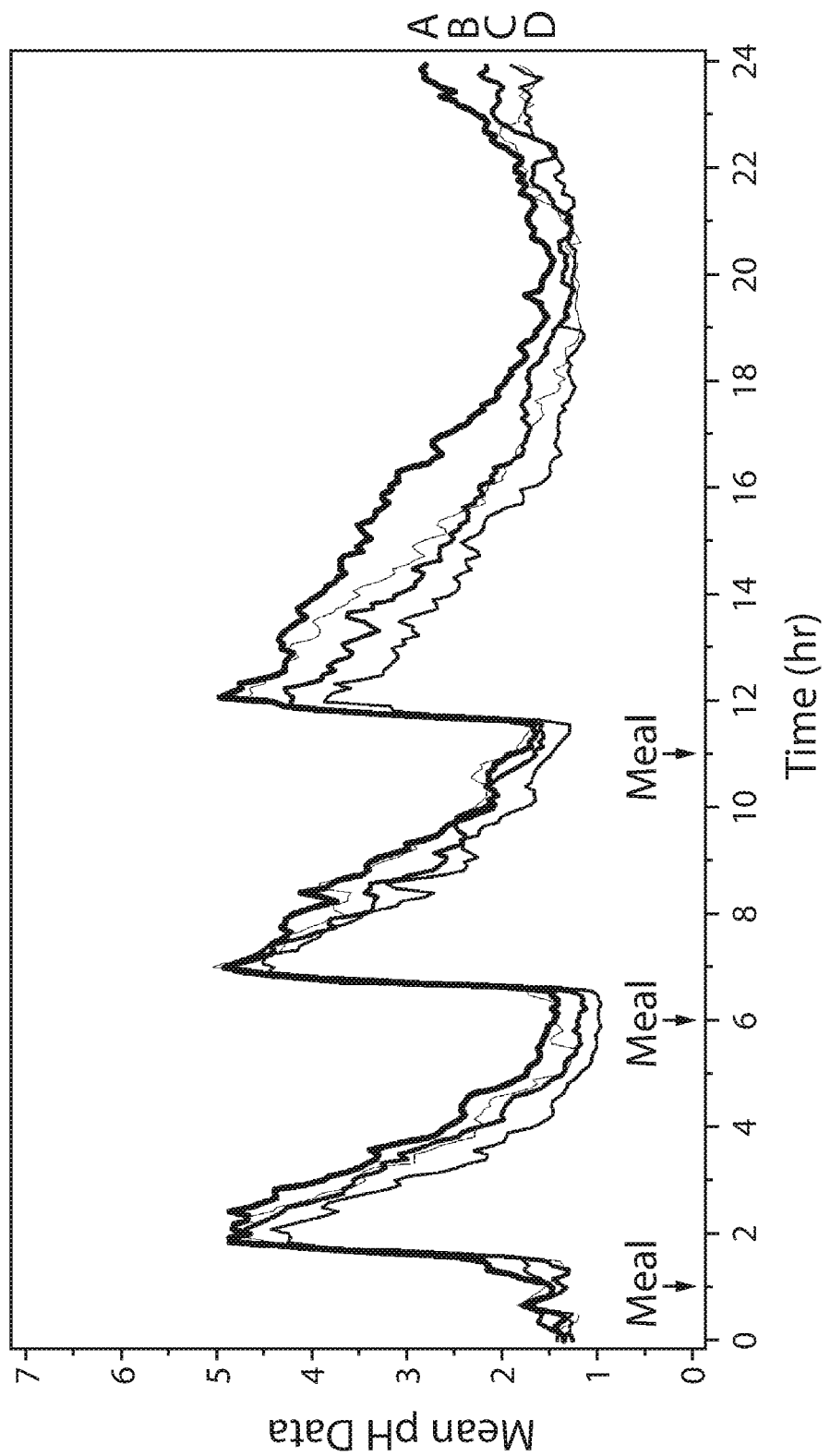
FIG. 2: Mean intragastric pH data over 24 hours on day 1 per protocol population. Treatment A=PN400/E30; B=PN400/E20; C=PN400/E10; D=EC E20+naproxen.

Results on Day 9 for the ITT population were similar to those from the PP population. The initial Day 9 pH measurements from all treatments showed the mean intragastric pH after an overnight fast was between 2.0 and 3.0, which was higher than the initial pH (between 1.0 and 2.0) on Day 1 (FIG. 2).

As shown in Table 4, the primary PD response of this study, i.e., percent time intragastric pH>4.0 on Day 9, increased with esomeprazole dose in the PN 400 treatments. However, a greater increase in the primary PD response was observed when esomeprazole dose increased from 10 to 20 mg in PN 400, i.e., from 40.9 to 76.5%. There was only a small increase in intragastric pH>4.0, from 71.4 to 76.5%, as the esomeprazole dose increased from 20 to 30 mg in PN 400.

Secondary Pharmacodynamic Endpoint: Percent Time Intragastric pH>4.0 on Day 1

Results from Day 1 are set forth in Table 5. The LS mean percent time intragastric pH>4.0 ranged from approximately 13% with PN 400/E10 to approximately 28% with PN 400/E30.

TABLE 5

Percent of Time with Intragastric pH Greater than 4.0-Day 1-Per-Protocol Population

| Treatment | A<br>PN 400/E30<br>N = 25 | B<br>PN 400/E20<br>N = 25 | C<br>PN 400/E10<br>N = 24 | D<br>EC E20 +<br>Naproxen<br>N = 25 |
|---|---|---|---|---|
| % Time of pH >4.0 |  |  |  |  |
| Mean (SD) | 27.79 (22.63) | 20.50 (16.61) | 12.81 (11.11) | 21.34 (13.63) |
| Median | 19.96 | 15.26 | 9.09 | 16.82 |
| % CV | 81 | 81 | 87 | 64 |
| Range | 1.77-89.61 | 4.35-74.40 | 3.00-53.75 | 3.16-58.20 |
| LS Mean (SE) | 27.90 (3.31) | 20.58 (3.31) | 12.66 (3.35) | 21.51 (3.31) |
|  | A vs. D | B vs. D | C vs. D |  |
| LS Mean Difference (SE) | 6.39 (3.18) | −0.92 (3.18) | −8.85 (3.22) | — |
| 95% Confidence Interval | 0.04-12.75 | −7.28-5.43 | −15.28--2.42 | — |

Mean pH data over 24 hours on Day 1 is presented in FIG. 2. The pH profiles on Day 1 showed that following an overnight fast, the mean baseline intragastric pH was low, between 1.0 and 2.0, prior to any treatment. There were three pH increases above pH 4.0 throughout the day that were associated with food intake at 1, 6 and 11 hours. The increase in intragastric pH occurred at approximately one hour after each meal for all treatments. There was only a minimal effect of any of the study treatments on intragastric pH, beyond the effect of food, throughout the first 24 hours on the first day of treatment.

Other Pharmacodynamic Findings

Analysis of percent time of pH>3.0 and >5.0 on Day 9 resulted in a similar pattern statistically as that of the primary endpoint of percent time pH>4 on Day 9 for PP population, with PN 400/E30 and PN 400/E20 showing a greater acid-reducing capacity than EC E20+naproxen, which had a greater capacity than PN 400/E10, based on LS mean differences and 95% CIs. Analysis results of percent time of pH>3.0 and >5.0 on Day 1 were similar as results for the primary endpoint of % time pH>4 on Day 1 based on the PP population. ITT population results were similar to those of the PP population.

As PN 400 is dosed BID, the individual time intervals corresponding to this dosing regimen, i.e., 0-10 hours and 10-24 hours, were analyzed for percent time intragastric pH>4.0 on Day 9. The results indicated that for the 0-10 hours period, PN 400/E30 treatment resulted in a greater percent time with intragastric pH>4.0 (84%) than treatment with EC E20 +naproxen (71%). While PN 400/E20 also had a high percent time intragastric pH>4.0 (79%), the results were not statistically significantly different from the EC E20+naproxen treatment. With BID dosing, both PN400/E30 and PN400/E20 had greater percent time intragastric pH>4.0 (71% and 66%, respectively) compared to treatment with EC E20+naproxen (47%) for the 10-24 hour treatment interval. The PN400/E10 treatment had a lower percent time intragastric pH>4.0 compared to treatment with EC E20 +naproxen for both the 0-10 hours (52%) and the 10-24 hours (33%) treatment interval.

Pharmacokinetic Endpoints

On Day 1, PK data analysis was performed for esomeprazole and naproxen plasma profiles obtained from 28 subjects completing PN 400/E30, PN 400/E20 and EC E20+naproxen; and 27 subjects completing PN 400/E10.

On Day 9, PK data analysis was performed for esomeprazole or naproxen plasma profiles from 28 subjects completing PN 400/E30 and EC E20+naproxen, and 27 subjects completing PN 400/E20 and PN 400/E10.

PK parameters for esomeprazole were determined following the three different PN 400 treatments and PK parameters for naproxen were determined following each of the 4 treatments including peak plasma concentration ($C_{max}$) on Days 1 and 9, time to peak plasma concentration ($t_{max}$) on Days 1 and 9, area under the plasma concentration vs time curve from time zero to the last time point with measurable drug concentration ($AUC_{0-t}$) on Days 1 and 9, and the terminal half-life ($t\frac{1}{2}$), if possible, following both the AM and PM doses on Days 1 and 9. In addition, the AUC from time zero (time of dosing) to 10 hours post-AM dose ($AUC_{0-10,am}$) and AUC from time zero (time of dosing) to 14 hours post-PM dose ($AUC_{0-14,pm}$) and a total daily AUC ($AUC_{0-24}$) were determined on Days 1 and 9. PK parameters for esomeprazole following EC E20+naproxen included $C_{max}$, $t_{max}$, $AUC_{0-t}$, $t\frac{1}{2}$, and $AUC_{0-24}$ following the AM dose on both Days 1 and 9.

Statistical analysis was performed using Analysis of Variance (ANOVA) to determine the point estimate and 90% CI of the Day 9 to Day 1 ratios for the following parameters for both naproxen and esomeprazole $C_{max,am}$, $C_{max, pm}$, $AUC_{0-10, am}$, $AUC_{0-14, pm}$, and $AUC_{0-24}$.

Plasma esomeprazole and naproxen concentration vs. time data are listed by treatment, study day and subject. The concentration data were summarized by treatment and study day at each nominal (or scheduled) sampling time using descriptive statistics including mean, SD, % CV, median, minimum and maximum. Plasma concentrations below the LLOQ (i.e., 1 ng/mL for esomeprazole, and 0.10 μg/mL for naproxen) were treated as a zero value for calculating descriptive statistics. The mean/median value at a time point with one or more below the LLOQ (BQL) values was reported unless the mean/median value was below the LLOQ of the assay, in which case the value was reported as BQL. Individual subject plasma concentration vs time curves were plotted against the actual sampling time, and the mean/median plasma concentration vs. time curves were plotted against nominal sampling time by treatment.

The plasma concentration vs. time data of each analyte were subjected to non-compartmental analysis using WinNonlin version 4.1 (Pharsight Corporation, Mountain View, Calif.). The actual blood sampling time for each sample was used for PK data analysis. For analyte concentrations resulting from BID doses, i.e., esomeprazole in Treatments A, B, and C or naproxen in all 4 treatments, PK analysis was performed separately for the plasma profiles obtained after the AM and PM doses. Thus, the actual post-dose sampling times for concentration vs. time profiles after the PM dose were calculated based on the elapsed time from the actual dosing time of the PM dose.

For PK analysis, plasma concentrations below the LLOQ (BQL value) in individual profiles of each analyte were handled as follows. If the value occurred in a profile during the absorptive phase of the profile, i.e., before the maximum concentration in a profile was observed, it was assigned a value of zero concentration. A single BQL value occurring between two measurable analyte concentrations, not in the absorptive phase of a profile, was generally omitted. If two or more BQL values occurred in succession, post peak time (or during the elimination phase), the profile was determined to have terminated at the last time point with measurable analyte concentration of the profile.

PK parameters calculated for esomeprazole (following each of the three PN 400 treatments) and for naproxen (following each of the 4 treatments) on Days 1 and 9 included the following: Maximum observed plasma concentration following the AM dose ($C_{max,am}$) and following the PM dose ($C_{max,pm}$); Time to peak plasma concentration following the AM dose ($t_{max,am}$) and following the PM dose ($t_{max,pm}$); Time to the first measurable plasma concentration following the AM dose (tlag,am) and following the PM dose ($t_{lag,pm}$); Area under the plasma concentration vs. time curve (AUC) from time zero to the last time point with measurable drug concentration (tlast) following the AM dose ($AUC_{0-t,am}$) and following the PM dose ($AUC_{0-t,pm}$), calculated using the linear-up and log-down trapezoidal method in WinNonlin; Apparent first-order elimination rate constant ($\lambda_{z,am}$ and $\lambda_{z,pm}$), determined, if data permit, by the slope of the apparent terminal log-linear phase of the plasma drug concentration vs. time curve using at least 3 time points; Apparent plasma half-life ($t\frac{1}{2}$), if data permit, determined as $0.693/\lambda_z$ following the AM and PM doses, i.e., $t\frac{1}{2}$,am and $t\frac{1}{2}$,pm, respectively; AUC from time zero (time of AM dosing) to 10 hours after the AM dose ($AUC_{0-10,am}$), if necessary, with extrapolation using $\lambda_{z,am}$ estimate from $t_{last}$ to 10 hrs post the AM dose; AUC from time zero (time of PM dosing) to 14 hours after the PM dose ($AUC_{0-14,pm}$), if necessary, with extrapolation using $\lambda_{z,pm}$ estimate from $t_{last}$ to 14 hrs post PM dose; and Total daily AUC ($AUC_{0-24}$) from time zero (time of AM dosing) to 24 hours after the AM dose, which is determined as $AUC_{0-10,am}+AUC_{0-14,pm}$.

The PK parameters calculated for esomeprazole following Treatment D after the AM dose on Days 1 and 9 included $C_{max}$, $t_{max}$, $AUC_{0-t}$, $t\frac{1}{2}$ and $AUC_{0-24}$. The same methods as described above were applied.

Descriptive statistics, including mean, SD, % CV, median, minimum and maximum, were calculated for all PK parameters of naproxen and esomeprazole by treatment and study day. Geometric mean and associated 95% confidence interval (CI) were also calculated for all PK parameters, except $t_{max}$.

Statistical analysis was performed using ANOVA to determine the point estimate and associated 90% CI of the Day 9 to Day 1 ratios for the following parameters: $C_{max,am}$, $C_{max,pm}$, $AUC_{0-10,am}$, $AUC_{0-14,pm}$, and $AUC_{0-24}$ for esomeprazole data in each of the three PN 400 treatments, and for naproxen data in each of the 4 treatments. For esomeprazole data from Treatment D, the Day 9 to Day 1 ratios for $C_{max}$ and $AUC_{0-24}$ were determined. Natural log-transformed $C_{max}$ and AUC values were used for the analyses, thus geometric least-squares mean ratios for each parameter were determined.

Dose proportionality in the $C_{max,am}$, $C_{max,pm}$, $AUC_{0-10,am}$, $AUC_{0-10,am}$, and $AUC_{0-24}$ of esomeprazole from the three PN400 treatments was analyzed on Days 1 and 9 separately, using the power model as follows:

$$y = a*(\text{dose})^b$$

$$\ln(y) = \ln(a) + b*\ln(\text{dose})$$

where y is the PK parameter value and ln = natural log. The power model included ln(dose) and period as fixed effects and subject as a random effect.

Esomeprazole

Table 6 summarizes the results from the PK analysis that was performed for esomeprazole plasma concentration vs. time data for the 28 subjects who completed PN 400/E30 and EC E20+naproxen treatments and 27 subjects who completed PN 400/E10 treatment on Days 1 and 9, and 28, and 27 subjects who completed PN 400/E20 treatment on Day 1 and Day 9, respectively.

TABLE 6

Summary of Esomeprazole Pharmacokinetic Results

| Treatment | Day/Dose Time | $C_{max}$ (ng/mL) | $t_{max}$ (hr) | $AUC_{0-10,am}$ or $AUC_{0-14,pm}$ (hr * ng/mL) | $AUC_{0-24}$ (hr * ng/mL) | $t_{1/2}$ (hr) |
|---|---|---|---|---|---|---|
| A | 1 AM | 487 (82) | 0.50 (0.33-1.50) | 591 (108) | | 0.892 (35) |
| PN 400/E30 | 1 PM | 187 (132) | 1.50 (0.33-4.00) | 388 (137) | 978 (115) | 1.11 (62) |
| | 9 AM | 1584 (39) | 0.50 (0.17-1.50) | 2779 (45) | | 1.26 (25) |
| | 9 PM | 810 (59) | 1.00 (0.33-8.00) | 2066 (53) | 4911 (42) | 1.46 (34) |
| B | 1 AM | 292 (77) | 0.50 (0.20-1.50) | 350 (113) | | 0.846 (42) |
| PN 400/E20 | 1 PM | 96.6 (104) | 1.49 (0.33-3.00) | 206 (141) | 556 (119) | 0.994 (55) |
| | 9 AM | 715 (52) | 0.50 (0.17-1.50) | 1216 (69) | | 1.12 (33) |
| | 9 PM | 428 (73) | 0.75 (0.33-3.00) | 919 (84) | 2134 (74) | 1.31 (42) |
| C | 1 AM | 138 (71) | 0.33 (0.17-3.10) | 148 (111) | | 0.810 (48) |
| PN 400/E10 | 1 PM | 35.3 (84) | 1.50 (0.33-3.00) | 85.7 (179) | 237 (133) | 0.878 (50) |
| | 9 AM | 278 (57) | 0.33 (0.17-1.00) | 368 (89) | | 0.860 (41) |
| | 9 PM | 97.6 (136) | 1.00 (0.33-2.00) | 223 (134) | 602 (103) | 1.09 (47) |
| D | 1 AM | 282 (66) | 1.50 (1.00-16.0) | 520 (64) | 580 (67) | 1.09 (44) |
| EC E20 + naproxen | 9 AM | 435 (48) | 1.50 (1.00-14.0) | 1046 (54) | 1212 (47) | 1.27 (36) |

Values are mean (% CV) for all parameters, except for tmax, which are median (range).

Following oral administration of PN 400 on Day 1, esomeprazole concentrations were measurable at 10 minutes after the AM dose, and at 20-30 minutes after the PM dose. Plasma esomeprazole concentrations after the PM dose were lower than those after the AM dose on both days. $C_{max}$ and AUCs of esomeprazole increased nearly dose proportionally after the AM dose on Day 1, but more than dose proportionally after the PM dose on Day 1 and both the AM and PM doses on Day 9. Esomeprazole concentrations were much higher on Day 9 than on Day 1 for each PN 400 treatment. The geometric least-squares mean $AUC_{0-24}$ ratios, Day 9 to Day 1, were 7.13, 4.10, and 2.26 for treatment with PN 400/E30, PN 400/E20, and PN 400/E10, respectively.

Following EC E20+naproxen treatment, the first measurable esomeprazole concentration was at 0.5 to 1.5 hrs post dose. To evaluate the effect of esomeprazole in the PN400/E20 treatment group with the EC E20 in the EC E20+naproxen treatment group, the PK parameters from PN400/E20 and EC E20+naproxen treatment groups were compared. On Day 1, esomeprazole $C_{max,am}$ mean values were approximately equal for the PN400/E20 and EC E20+naproxen treatments (292 and 282 ng/ml, respectively). The $AUC_{0-10}$ mean values on Day 1 from the PN400/E20 treatment were approximately two-thirds that of the EC E20+naproxen treatment (350 vs. 520 hr·ng/ml, respectively). By Day 9, however, the esomeprazole $AUC_{0-10}$ for the PN400/E20 treatment group was greater than the EC E20+naproxen treatment group (1216 vs 1046 hr·ng/ml, respectively) and $C_{max,am}$ from the PN400/E20 treatment group was almost double that of the EC E20+naproxen treatment group (715 vs 435 ng/ml, respectively).

Figure 3:
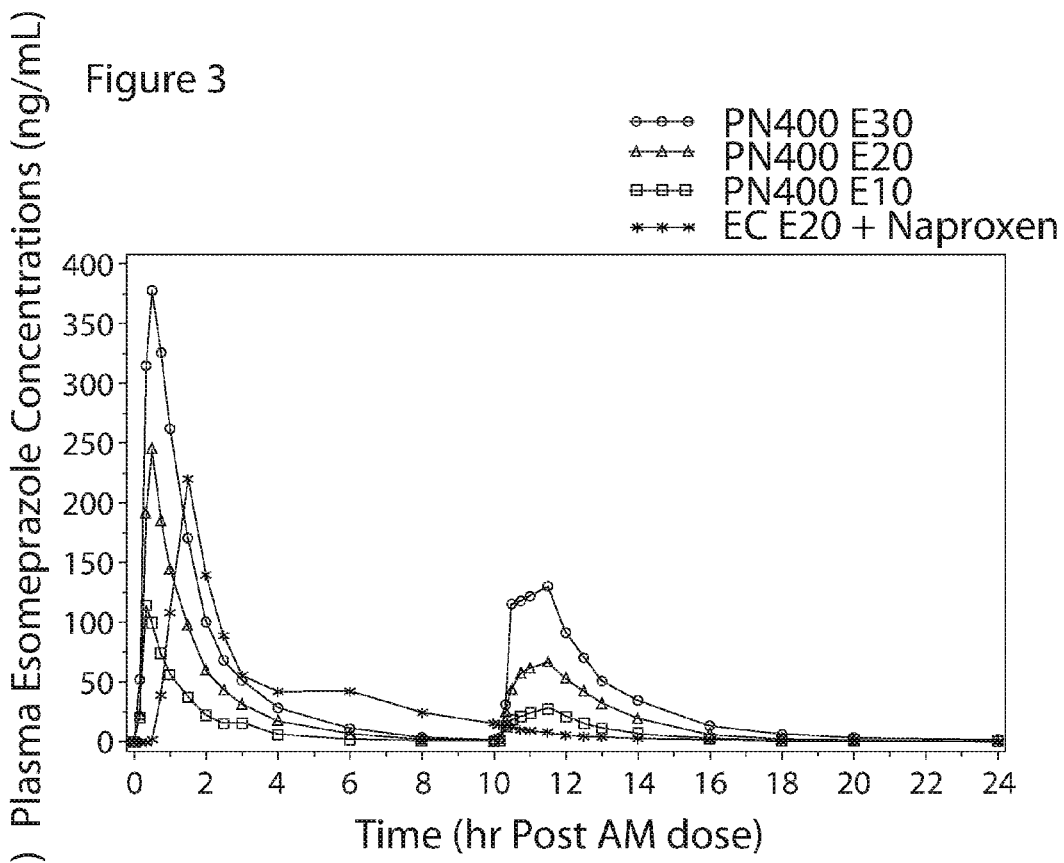
FIG. 3: Mean plasma esomeprazole concentration vs. time curves on day 1.
Figure 4:
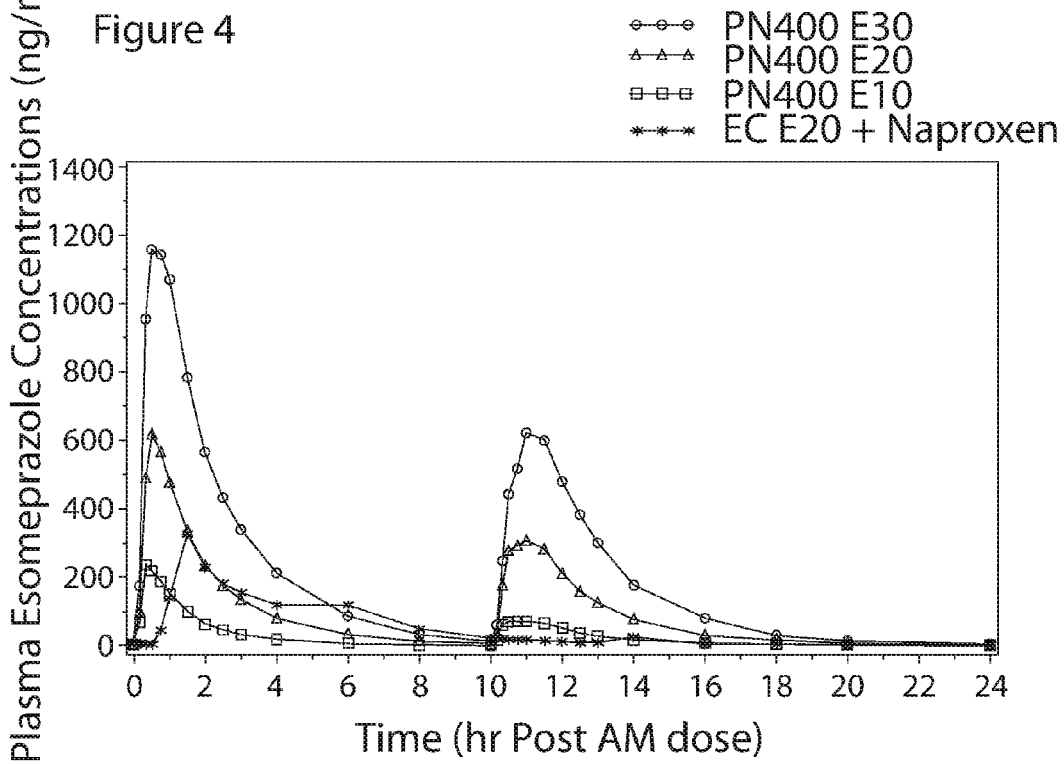
FIG. 4: Mean plasma esomeprazole concentration vs. time curves on day 9.

Mean and median plasma esomeprazole concentration vs time profiles following all four treatments were plotted and the mean plots are presented in FIGS. 3 and 4. These figures demonstrate that esomeprazole concentrations following AM or PM doses on Day 1 or Day 9 increased with the esomeprazole dose in the PN 400 treatments. Furthermore, on both Days 1 and 9, esomeprazole concentrations after the AM dose were higher than those after the PM dose for each PN 400 treatment. Following EC E20+naproxen treatment, the mean profiles demonstrate a delayed absorption peak on both Days 1 and 9 as compared to PN 400. In addition, peak esomeprazole concentrations following EC E20+naproxen treatment were lower than those following PN 400/E20, especially on Day 9 (about 50% lower).

The pharmacokinetic parameters of esomeprazole following the AM and PM doses on Day 1 and Day 9 of each treatment group are summarized in Tables 7 to 10 below.

TABLE 7

Summary of Esomeprazole Pharmacokinetic Parameters by Study Day and Dose Time for Treatment A (PN 400/E30)

| Day | Dose Time | Statistics | $C_{max}$ (ng/ml) | $t_{max}$ (hr) | $AUC_{0-t}$ (hr * ng/mL) | $AUC_{0-10,am}$ or $AUC_{0-14,pm}$ (hr * ng/mL) | $AUC_{0-24}$ (hr * ng/ml) | $t^{1/2}$ (hr) |
|---|---|---|---|---|---|---|---|---|
| 1 | AM | Mean | 487 | | 588 | 591 | | 0.892 |
| | n = 28 | % CV | 82 | | 109 | 108 | | 35 |
| | | Median | 325 | 0.50 | 352 | 354 | | 0.810 |
| | | Min | 52.1 | 0.33 | 59.4 | 61.0 | | 0.520 |
| | | Max | 1400 | 1.50 | 3087 | 3087 | | 1.96 |
| 1 | PM | Mean | 187 | | 385 | 388 | 978 | 1.11 |
| | n = 28 | % CV | 132 | | 138 | 137 | 115 | 62 |
| | | Median | 114 | 1.50 | 204 | 207 | 579 | 0.861 |
| | | Min | 21.1 | 0.33 | 37.4 | 40.3 | 101 | 0.593 |
| | | Max | 1290 | 4.00 | 2315 | 2315 | 5402 | 3.89 |
| 9 | AM | Mean | 1584 | | 2778 | 2779 | | 1.26 |
| | n = 28 | % CV | 39 | | 46 | 45 | | 25 |
| | | Median | 1560 | 0.50 | 2586 | 2586 | | 1.18 |
| | | Min | 384 | 0.17 | 874 | 879 | | 0.83 |
| | | Max | 3520 | 1.50 | 5841 | 5841 | | 1.80 |
| 9 | PM | Mean | 810 | | 1990 | 2066 | 4911 | 1.46[a] |
| | n = 28 | % CV | 59 | | 57 | 53 | 42 | 34 |
| | | Median | 749 | 1.00 | 2090 | 2159 | 5488 | 1.38 |
| | | Min | 13.7 | 0.33 | 21.7 | 342 | 1519 | 0.75 |
| | | Max | 1970 | 8.00 | 4956 | 4956 | 9770 | 2.91 |

[a] n = 27

TABLE 8

Summary of Esomeprazole Pharmacokinetic Parameters by Study Day and Dose Time for Treatment B (PN 400/E20)

| Day | Dose Time | StatisTics | $C_{max}$ (ng/mL) | $t_{max}$ (hr) | $AUC_{0-t}$ (hr * ng/mL) | $AUC_{0-10,am}$ or $AUC_{0-14,pm}$ (hr * ng/mL) | $AUC_{0-24}$ (hr * ng/mL) | $t^{1/2}$ (hr) |
|---|---|---|---|---|---|---|---|---|
| 1 | AM | Mean | 292 | | 348 | 350 | | 0.846 |
| | n = 28 | % CV | 77 | | 114 | 113 | | 42 |
| | | Median | 209 | 0.50 | 245 | 248 | | 0.696 |
| | | Min | 47.1 | 0.20 | 57.0 | 58.1 | | 0.434 |
| | | Max | 916 | 1.50 | 1971 | 1971 | | 1.90 |

TABLE 8-continued

Summary of Esomeprazole Pharmacokinetic Parameters by Study Day and Dose Time for Treatment B (PN 400/E20)

| Day | Dose Time | StatisTics | $C_{max}$ (ng/mL) | $t_{max}$ (hr) | $AUC_{0-t}$ (hr * ng/mL) | $AUC_{0-10,am}$ or $AUC_{0-14,pm}$ (hr * ng/mL) | $AUC_{0-24}$ (hr * ng/mL) | $t\frac{1}{2}$ (hr) |
|---|---|---|---|---|---|---|---|---|
| 1 | PM | Mean | 96.6 | | 203 | 206 | 556 | 0.994 |
| | n = 28 | % CV | 104 | | 144 | 141 | 119 | 55 |
| | | Median | 71.7 | 1.49 | 106 | 108 | 362 | 0.844 |
| | | Min | 16.0 | 0.33 | 24.3 | 28.6 | 86.7 | 0.410 |
| | | Max | 439 | 3.00 | 1459 | 1459 | 3429 | 2.82 |
| 9 | AM | Mean | 715 | | 1215 | 1216 | | 1.12 |
| | n = 27 | % CV | 52 | | 70 | 69 | | 33 |
| | | Median | 700 | 0.50 | 947 | 948 | | 1.03 |
| | | Min | 112 | 0.17 | 186 | 188 | | 0.485 |
| | | Max | 1300 | 1.50 | 2931 | 2931 | | 1.82 |
| 9 | PM | Mean | 428 | | 914 | 919 | 2134 | 1.31 |
| | n = 27 | % CV | 73 | | 85 | 84 | 74 | 42 |
| | | Median | 373 | 0.75 | 603 | 642 | 1727 | 1.32 |
| | | Min | 30.5 | 0.33 | 59.3 | 63.5 | 288 | 0.686 |
| | | Max | 1300 | 3.00 | 2931 | 2931 | 5737 | 3.10 |

TABLE 9

Summary of Esomeprazole Pharmacokinetic Parameters by Study Day and Dose Time for Treatment C (PN 400/E10)

| Day | Dose Time | StatisTics | $C_{max}$ (ng/mL) | $t_{max}$ (hr) | $AUC_{0-t}$ (hr * ng/mL) | $AUC_{0-10,am}$ or $AUC_{0-14,pm}$ (hr * ng/mL) | $AUC_{0-24}$ (hr * ng/mL) | $t\frac{1}{2}$ (hr) |
|---|---|---|---|---|---|---|---|---|
| 1 | AM | Mean | 138 | | 143 | 148 | | 0.810 |
| | n = 27 | % CV | 71 | | 115 | 111 | | 48 |
| | | Median | 123 | 0.33 | 84.8 | 105 | | 0.703 |
| | | Min | 24.4 | 0.17 | 35.0 | 36.1 | | 0.454 |
| | | Max | 370 | 3.10 | 882 | 882 | | 2.21 |
| 1 | PM | Mean | 35.3 | | 80.6 | 85.7[b] | 237[b] | 0.878[a] |
| | n = 27 | % CV | 84 | | 188 | 179 | 133 | 50 |
| | | Median | 32.1 | 1.50 | 41.8 | 48.7 | 155 | 0.734 |
| | | Min | 4.2 | 0.33 | 8.40 | 9.80 | 45.9 | 0.593 |
| | | Max | 141 | 3.00 | 818 | 818 | 1700 | 2.67 |
| 9 | AM | Mean | 278 | | 366 | 368 | | 0.860 |
| | n = 27 | % CV | 57 | | 90 | 89 | | 41 |
| | | Median | 242 | 0.33 | 223 | 224 | | 0.653 |
| | | Min | 33.0 | 0.17 | 41.0 | 42.6 | | 0.526 |
| | | Max | 594 | 1.00 | 1284 | 1284 | | 1.85 |
| 9 | PM | Mean | 97.6 | | 215 | 223[b] | 602[b] | 1.09[b] |
| | n = 27 | % CV | 136 | | 137 | 134 | 103 | 47 |
| | | Median | 42.2 | 1.00 | 69.9 | 76.9 | 306 | 0.944 |
| | | Min | 11.0 | 0.33 | 17.3 | 18.8 | 63.7 | 0.370 |
| | | Max | 554 | 2.00 | 1076 | 1080 | 2186 | 2.79 |

[a] n = 25;
[b] n = 26

TABLE 10

Summary of Esomeprazole Pharmacokinetic Parameters by Study Day and Dose Time for Treatment D (EC E20 + Naproxen)

| Day | Dose Time | StatisTics | $C_{max}$ (ng/mL) | $t_{max}$ (hr) | $AUC_{0-t}$ (hr * ng/mL) | $AUC_{0-10,pm}$ (hr * ng/mL) | $AUC_{0-24}$ (hr * ng/mL) | $t\frac{1}{2}$ (hr) |
|---|---|---|---|---|---|---|---|---|
| 1 | AM | Mean | 282 | | 567 | 540[b] | 580[b] | 1.09[b] |
| | n = 28 | % CV | 66 | | 68 | 60 | 67 | 44 |
| | | Median | 231 | 1.50 | 466 | 471 | 471 | 0.931 |
| | | Min | 1.1 | 1.00 | 143 | 143 | 144 | 0.633 |
| | | Max | 678 | 16.0 | 1777 | 1359 | 1777 | 2.56 |

TABLE 10-continued

Summary of Esomeprazole Pharmacokinetic Parameters by Study Day and Dose Time for Treatment D (EC E20 + Naproxen)

| Day | Dose Time | StatisTics | $C_{max}$ (ng/mL) | $t_{max}$ (hr) | $AUC_{0-t}$ (hr * ng/mL) | $AUC_{0-10,pm}$ (hr * ng/mL) | $AUC_{0-24}$ (hr * ng/mL) | $t^{1/2}$ (hr) |
|---|---|---|---|---|---|---|---|---|
| 9 | AM | Mean | 435 | | 1136 | 1046 | 1212[b] | 1.27[a] |
| | n = 28 | % CV | 48 | | 52 | 54 | 47 | 36 |
| | | Median | 453 | 1.50 | 1056 | 859 | 1123 | 1.16 |
| | | Min | 98.0 | 1.00 | 292 | 289 | 429 | 0.755 |
| | | Max | 939 | 14.0 | 2279 | 2217 | 2279 | 2.46 |

[a]n = 25;
[b]n = 26

Naproxen

Table 11 summarizes the results from the PK analysis that was performed for naproxen plasma concentration vs. time data for the 28 subjects who completed PN 400/E30 and EC E20+naproxen treatments and 27 subjects who completed the PN 400/E10 treatment on Days 1 and 9, and 28, and 27 subjects who completed PN 400/E20 treatment on Day 1 and Day 9, respectively.

variability in naproxen AUC between AM and PM doses was less on Day 9 than on Day 1, reflecting that naproxen levels are approximately at steady state with repeat dosing. $C_{max}$ values were somewhat more variable between the AM and PM doses on Day 1 compared to Day 9, with mean AM levels being lower than mean PM levels for all treatments on Day 1 and mean AM levels slightly higher than mean PM levels for all treatments on Day 9.

TABLE 11

Naproxen Pharmacokinetic Parameters

| Treatment | Day/Dose Time | $C_{max}$ (µg/mL) | $t_{max}$ (hr) | $AUC_{0-10,am}$ or $AUC_{0-14,pm}$ (hr * µg/mL) | $AUC_{0-24}$ (hr * µg/mL) | $t^{1/2}$ (hr) |
|---|---|---|---|---|---|---|
| A | 1 | 48.1 | 4.00 | 259 | | 8.52 |
| PN 400/E30 | AM | (53) | (2.00-10.0) | (56) | | (25) |
| | 1 | 68.9 | 14.0 | 471 | 730 | 12.1 |
| | PM | (28) | (0.50-14.0) | (30) | (32) | (30) |
| | 9 | 80.9 | 3.00 | 603 | | 9.17 |
| | AM | (23) | (0.00-8.00) | (21) | | (21) |
| | 9 | 76.2 | 10.4 | 648 | 1251 | 12.3 |
| | PM | (23) | (0.00-14.0) | (20) | (16) | (27) |
| B | 1 | 44.4 | 4.00 | 231 | | 8.75 |
| PN 400/E20 | AM | (68) | (2.00-10.0) | (70) | | (33) |
| | 1 | 71.5 | 14.0 | 450 | 680 | 11.8 |
| | PM | (26) | (0.00-14.0) | (33) | (36) | (28) |
| | 9 | 86.2 | 3.00 | 607 | | 9.42 |
| | AM | (22) | (0.00-8.05) | (19) | | (23) |
| | 9 | 76.8 | 10.0 | 678 | 1275 | 11.3 |
| | PM | (18) | (0.00-14.0) | (16) | (15) | (28) |
| C | 1 | 57.0 | 4.00 | 310 | | 9.24 |
| PN 400/E10 | AM | (31) | (2.00-10.0) | (35) | | (42) |
| | 1 | 68.6 | 10.0 | 508 | 819 | 12.7 |
| | PM | (26) | (0.00-14.0) | (29) | (21) | (23) |
| | 9 | 87.1 | 2.50 | 637 | | 9.91 |
| | AM | (21) | (0.00-8.00) | (17) | | (26) |
| | 9 | 78.6 | 14.0 | 672 | 1309 | 10.5 |
| | PM | (17) | (1.50-14.0) | (19) | (15) | (23) |
| D | 1 | 65.5 | 1.50 | 409 | | 8.85 |
| EC E20 + | AM | (25) | (0.75-6.00) | (16) | | (22) |
| naproxen | 1 | 81.5 | 1.50 | 685 | 1094 | 15.4 |
| | PM | (14) | (0.50-2.50) | (10) | (12) | (31) |
| | 9 | 90.0 | 1.50 | 617 | | 9.32 |
| | AM | (19) | (0.50-4.00) | (12) | | (23) |
| | 9 | 86.5 | 1.50 | 769 | 1387 | 14.4 |
| | PM | (13) | (0.75-4.00) | (10) | (10) | (17) |

Values are mean (% CV) for all parameters, except for $t_{max}$, which are median (range).

Following oral administration of PN 400 on Day 1, the first measurable naproxen concentrations occurred at about 2 hrs post AM dose. Plasma exposure to naproxen was comparable among the three PN 400 treatments. Following repeated doses of PN 400, the Day 9 to Day 1 naproxen concentration ratio was consistent with the expected accumulation based on the half-life estimates of naproxen. The Following the first (AM) dose of Treatment D on Day 1, plasma naproxen concentrations were measurable in all subjects at the first sampling time, i.e., 10 minutes post-dose and then up to 24 hours post AM dose (or 14 hours post PM dose), demonstrating typical performance of non-enteric coated naproxen.

Figure 5:
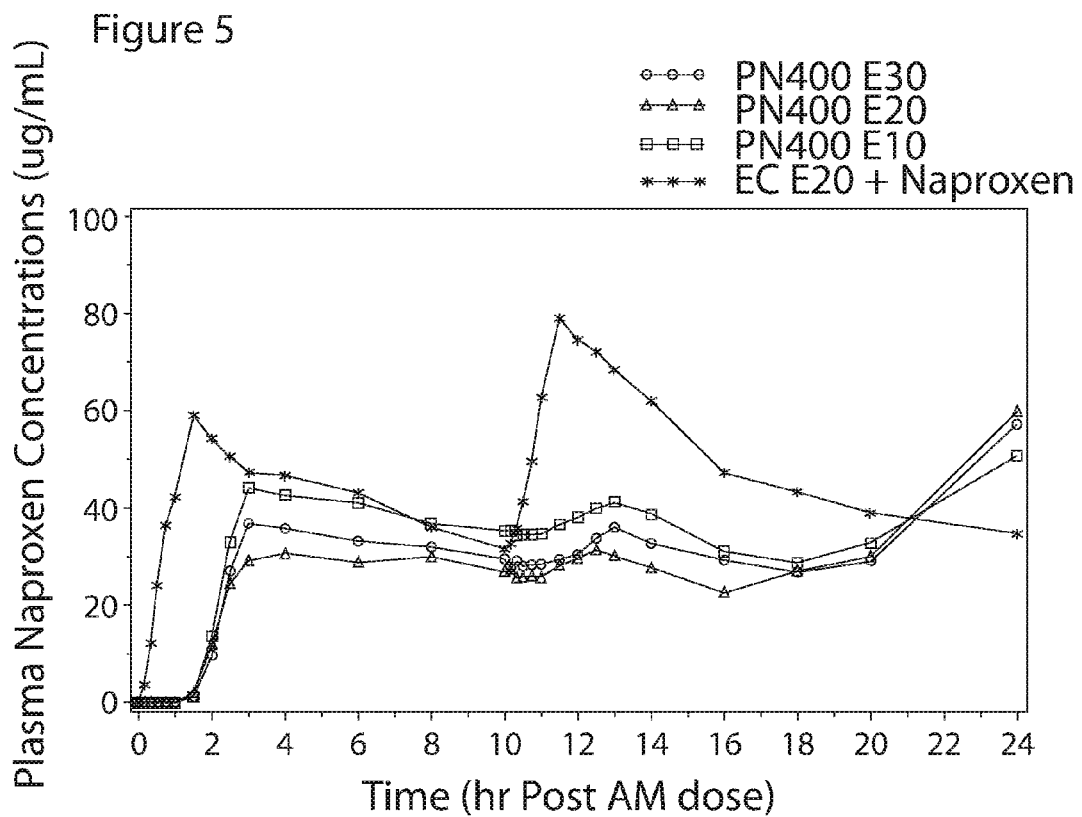
FIG. 5: Mean plasma naproxen concentration vs. time curves on day 1.
Figure 6:
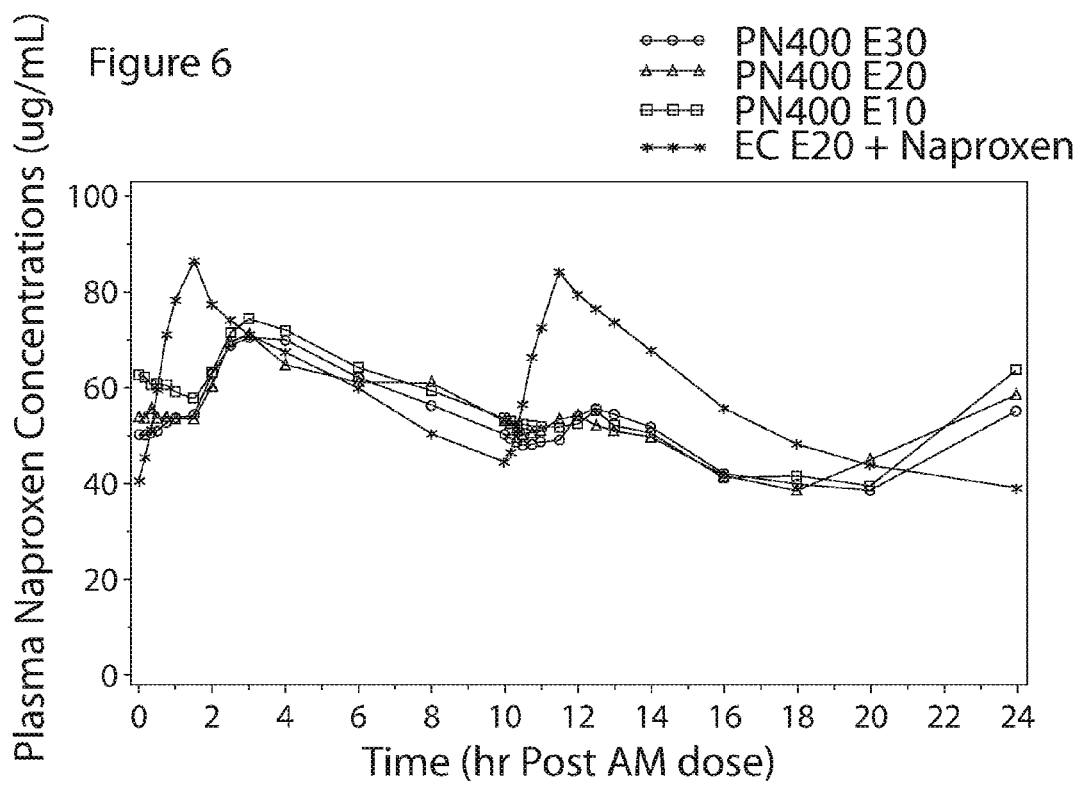
FIG. 6: Mean plasma naproxen concentration vs. time curves on day 9.

Mean and median plasma naproxen concentration vs time profiles following all 4 treatments are presented in FIGS. 5 and 6.

The PK parameters of naproxen following administration of the AM and PM doses on Day 1 and Day 9 of each treatment are summarized in Tables 12 to 15 below.

TABLE 12

Summary of Naproxen Pharmacokinetic Parameters by Study Day and Dose Time for Treatment A (PN 400/E30)

| Day | Dose Time | StatisTics | $C_{max}$ (μg/mL) | $t_{max}$ (hr) | $AUC_{0-t}$ (hr * μg/mL) | $AUC_{0-10,am}$ or $AUC_{0-14,pm}$ (hr * μg/mL) | $AUC_{0-24}$ (hr * μg/mL) | $t^{1/2}$ (hr) |
|---|---|---|---|---|---|---|---|---|
| 1 | AM | Mean | 48.1 | | 259 | 259 | | 8.52[a] |
| | n = 28 | % CV | 53 | | 56 | 56 | | 25 |
| | | Median | 53.2 | 4.00 | 339 | 339 | | 7.86 |
| | | Min | 0.0 | 2.00 | 0.0 | 0.0 | | 6.07 |
| | | Max | 82.5 | 10.0 | 428 | 428 | | 13.8 |
| 1 | PM | Mean | 68.9 | | 471 | 471 | 730 | 12.1[b] |
| | n = 28 | % CV | 28 | | 30 | 30 | 32 | 30 |
| | | Median | 68.5 | 14.0 | 464 | 464 | 780 | 10.8 |
| | | Min | 31.9 | 0.50 | 190 | 190 | 190 | 7.16 |
| | | Max | 114 | 14.0 | 716 | 716 | 1092 | 19.2 |
| 9 | AM | Mean | 80.9 | | 603 | 603 | | 9.17[c] |
| | n = 28 | % CV | 23 | | 21 | 21 | | 21 |
| | | Median | 80.0 | 3.00 | 568 | 568 | | 9.31 |
| | | Min | 44.5 | 0.00 | 345 | 345 | | 5.32 |
| | | Max | 139 | 8.00 | 944 | 944 | | 13.2 |
| 9 | PM | Mean | 76.2 | | 648 | 648 | 1251 | 12.3[d] |
| | n = 28 | % CV | 23 | | 20 | 20 | 16 | 27 |
| | | Median | 69.7 | 10.4 | 635 | 635 | 1269 | 12.0 |
| | | Min | 53.9 | 0.00 | 384 | 384 | 729 | 6.56 |
| | | Max | 127 | 14.0 | 932 | 932 | 1744 | 22.1 |

[a] n = 17;
[b] n = 21;
[c] n = 26.
[d] n = 24.

TABLE 13

Summary of Naproxen Pharmacokinetic Parameters by Study Day and Dose Time for Treatment B (PN 400/E20)

| Day | Dose Time | StatisTics | $C_{max}$ (μg/mL) | $t_{max}$ (hr) | $AUC_{0-t}$ (hr * μg/mL) | $AUC_{0-10,am}$ or $AUC_{0-14,pm}$ (hr * μg/mL) | $AUC_{0-24}$ (hr * μg/mL) | $t^{1/2}$ (hr) |
|---|---|---|---|---|---|---|---|---|
| 1 | AM | Mean | 44.4 | | 231 | 231 | | 8.75[a] |
| | n = 28 | % CV | 68 | | 70 | 70 | | 33 |
| | | Median | 50.1 | 4.00 | 291 | 291 | | 7.72 |
| | | Min | 0.00 | 2.00 | 0.00 | 0.0 | | 6.07 |
| | | Max | 94.4 | 10.0 | 490 | 490 | | 15.1 |
| 1 | PM | Mean | 71.5 | | 450 | 450 | 680 | 11.8[b] |
| | n = 28 | % CV | 26 | | 33 | 33 | 36 | 28 |
| | | Median | 69.4 | 14.0 | 443 | 443 | 756 | 10.9 |
| | | Min | 45.1 | 0.00 | 159 | 157 | 157 | 6.70 |
| | | Max | 110 | 14.0 | 831 | 831 | 977 | 18.7 |
| 9 | AM | Mean | 86.2 | | 607 | 607 | | 9.42[b] |
| | n = 27 | % CV | 22 | | 19 | 19 | | 23 |
| | | Median | 85.1 | 3.00 | 577 | 577 | | 8.65 |
| | | Min | 53.5 | 0.00 | 378 | 378 | | 5.48 |
| | | Max | 137 | 8.05 | 856 | 856 | | 13.9 |
| 9 | PM | Mean | 76.8 | | 668 | 678 | 1275 | 11.3[c] |
| | n = 27 | % CV | 18 | | 16 | 16 | 15 | 28 |
| | | Median | 73.0 | 10.0 | 661 | 661 | 1306 | 10.9 |
| | | Min | 51.2 | 0.00 | 458 | 458 | 939 | 7.97 |
| | | Max | 116 | 14.0 | 847 | 847 | 1659 | 19.2 |

[a] n = 15,
[b] n = 22,
[c] n = 20

TABLE 14

Summary of Naproxen Pharmacokinetic Parameters by Study Day and Dose Time for Treatment C (PN 400/E10)

| Day | Dose Time | StatisTics | $C_{max}$ (µg/mL) | $t_{max}$ (hr) | $AUC_{0-t}$ (hr * µg/mL) | $AUC_{0-10,am}$ or $AUC_{0-14,pm}$ (hr * µg/mL) | $AUC_{0-24}$ (hr * µg/mL) | $t^{1/2}$ (hr) |
|---|---|---|---|---|---|---|---|---|
| 1 | AM | Mean | 57.0 | | 310 | 310 | | 9.24[a] |
| n = 27 | | % CV | 31 | | 35 | 35 | | 42 |
| | | Median | 60.3 | 4.00 | 339 | 339 | | 7.88 |
| | | Min | 6.90 | 2.00 | 50.5 | 50.5 | | 3.36 |
| | | Max | 88.2 | 10.0 | 488 | 488 | | 21.8 |
| 1 | PM | Mean | 68.6 | | 508 | 508 | 819 | 12.7[b] |
| n = 27 | | % CV | 26 | | 29 | 29 | 21 | 23 |
| | | Median | 70.0 | 10.0 | 512 | 512 | 805 | 12.5 |
| | | Min | 30.0 | 0.00 | 271 | 271 | 454 | 6.93 |
| | | Max | 97.2 | 14.0 | 791 | 791 | 1225 | 20.2 |
| 9 | AM | Mean | 87.1 | | 637 | 637 | | 9.91[c] |
| n = 27 | | % CV | 21 | | 17 | 17 | | 26 |
| | | Median | 83.9 | 2.50 | 654 | 654 | | 9.29 |
| | | Min | 45.0 | 0.00 | 332 | 332 | | 6.88 |
| | | Max | 120 | 8.00 | 787 | 787 | | 16.1 |
| 9 | PM | Mean | 78.6 | | 672 | 672 | 1309 | 10.5[b] |
| n = 27 | | % CV | 17 | | 19 | 19 | 15 | 23 |
| | | Median | 73.5 | 14.0 | 687 | 687 | 1328 | 9.98 |
| | | Min | 62.4 | 1.50 | 349 | 349 | 681 | 7.17 |
| | | Max | 109 | 14.0 | 953 | 953 | 1647 | 16.1 |

[a]n = 22;
[b]n = 25;
[c]n = 23.

TABLE 15

Summary of Naproxen Pharmacokinetic Parameters by Study Day and Dose Time for Treatment D (EC E20 + Naproxen)

| Day | Dose Time | Statistics | $C_{max}$ (µg/mL) | $t_{max}$ (hr) | $AUC_{0-t}$ (hr * µg/mL) | $AUC_{0-10,am}$ or $AUC_{0-14,pm}$ (hr * µg/mL) | $AUC_{0-24}$ (hr * µg/mL) | $t^{1/2}$ (hr) |
|---|---|---|---|---|---|---|---|---|
| 1 | AM | Mean | 65.5 | | 409 | 409 | | 8.85[a] |
| n = 28 | | % CV | 25 | | 16 | 16 | | 22 |
| | | Median | 67.0 | 1.50 | 411 | 411 | | 8.44 |
| | | Min | 39.9 | 0.75 | 293 | 293 | | 6.17 |
| | | Max | 113 | 6.00 | 562 | 562 | | 14.1 |
| 1 | PM | Mean | 81.5 | | 685 | 685 | 1094 | 15.4 |
| n = 28 | | % CV | 14 | | 10 | 10 | 12 | 31 |
| | | Median | 80.8 | 1.50 | 662 | 662 | 1068 | 14.7 |
| | | Min | 58.2 | 0.50 | 592 | 592 | 909 | 9.04 |
| | | Max | 107 | 2.50 | 855 | 855 | 1398 | 32.8 |
| 9 | AM | Mean | 90.0 | | 617 | 617 | | 9.32 |
| n = 28 | | % CV | 19 | | 12 | 12 | | 23 |
| | | Median | 87.0 | 1.50 | 619 | 619 | | 9.39 |
| | | Min | 59.4 | 0.50 | 493 | 493 | | 5.77 |
| | | Max | 126 | 4.00 | 793 | 793 | | 15.4 |
| 9 | PM | Mean | 86.5 | | 769 | 769 | 1387 | 14.4 |
| n = 28 | | % CV | 13 | | 10 | 10 | 10 | 17 |
| | | Median | 89.6 | 1.50 | 760 | 760 | 1371 | 14.7 |
| | | Min | 67.3 | 0.75 | 619 | 619 | 1130 | 10.5 |
| | | Max | 123 | 4.00 | 930 | 930 | 1723 | 21.1 |

[a]n = 27.

Drug Concentrations or Pharmacokinetics in Relation to Pharmacodynamic Measurements As shown in FIG. 7, the relationship between the mean total plasma exposure to esomeprazole, i.e., $AUC_{0-24}$ on Day 9 (representing steady-state exposure), and the mean percent time with intragastric pH>4.0 on Day 9 (the primary PD endpoint) can be described by a typical pharmacological maximal response ($E_{max}$) model defined below:

Effect=$(E_{max}*AUC_{0-24})/(EC50+AUC_{0-24})$, where

Effect=Mean percent time intragastric pH>4.0 on Day 9 (assuming zero time intragastric pH>4.0 when esomeprazole $AUC_{0-24}$ equals zero)
Emax=Maximal Effect
EC50=Plasma mean $AUC_{0-24}$ required to produce 50% of the Maximal Effect The $E_{max}$ was estimated to be 90.4% of time with intragastric pH>4.0 over the daily interval at steady state. The $AUC_{0-24}$ value required to achieve half (or 50%) of the maximal response was estimated to be 713 hr*ng/mL. Following PN 400/E20, the PD response had achieved about 80% of the maximal response, which was only slightly less than that (85% of $E_{max}$) achieved by PN 400/E30.

Repeat doses of PN 400/E30 and PN 400/E20 resulted in faster onset of increased intragastric pH (at about 1 hour post dose) than EC E20+naproxen, which was at about 1.5 hours post-dose (FIG. 1).

Figure 8A:
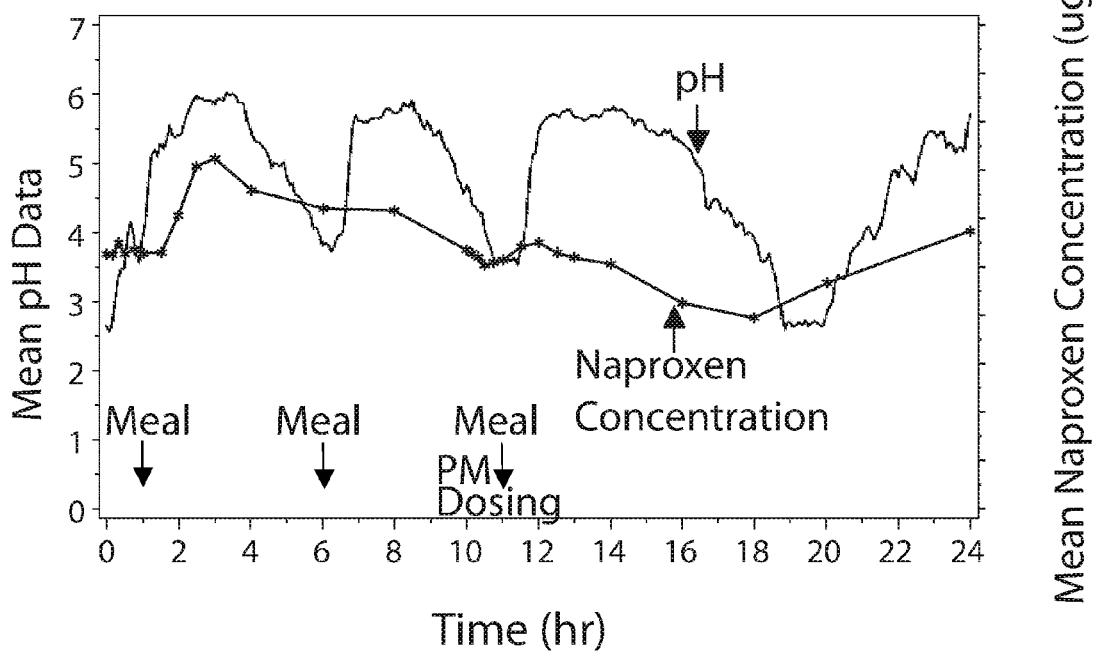
FIG. 8A: Mean pH data and mean naproxen concentration vs. time profiles over a 24-hour period on day 9: Treatment B (PN 400/E20).

As shown in the FIG. 8A, the release of naproxen from PN 400 occurred 1.5 to 2 hours post AM dose. Before naproxen was absorbed to peak concentrations following PN 400 treatment, intragastric pH had already achieved high levels, well above pH 4.0 (FIG. 8A). In fact, with the BID regimen of PN 400/E20, given 1 hour before a meal, the intragastric pH was maintained at above 4.0 for greater than 70% of time over a 24-hour period, which would encompass any rise in plasma naproxen concentrations throughout the day.

Figure 8B:
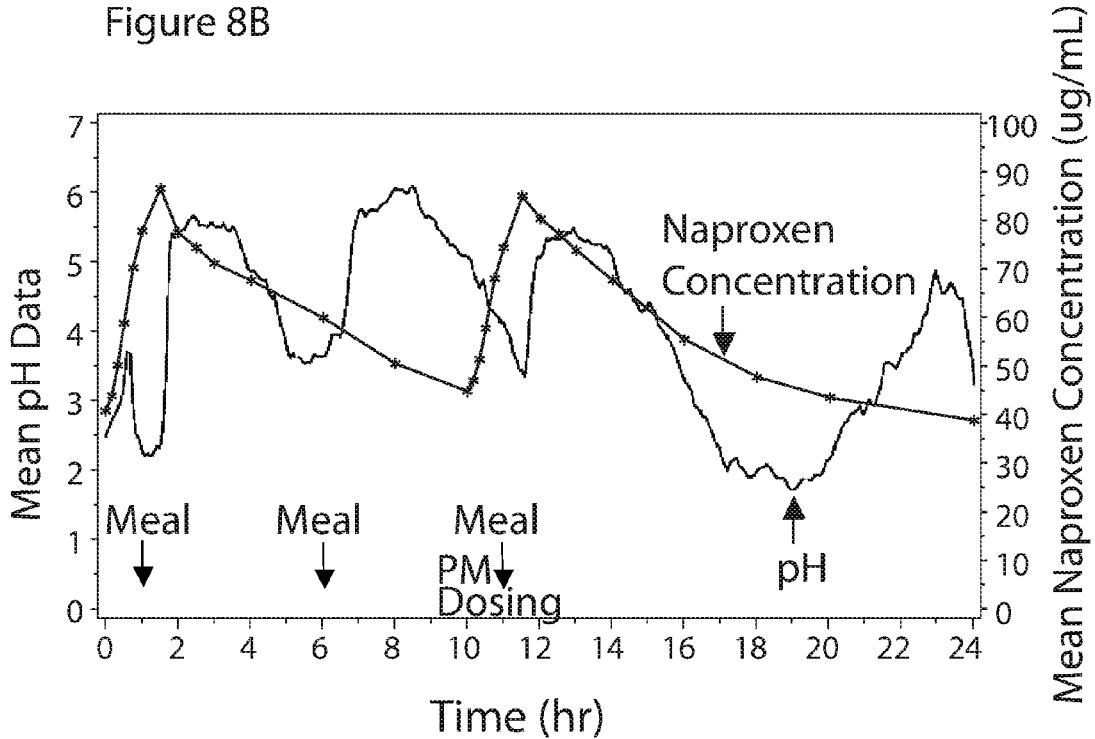
FIG. 8B: Mean pH data and mean naproxen concentration vs. time profiles over a 24-hour period on day 9: Treatment D (EC E20+naproxen).
Figure 11:
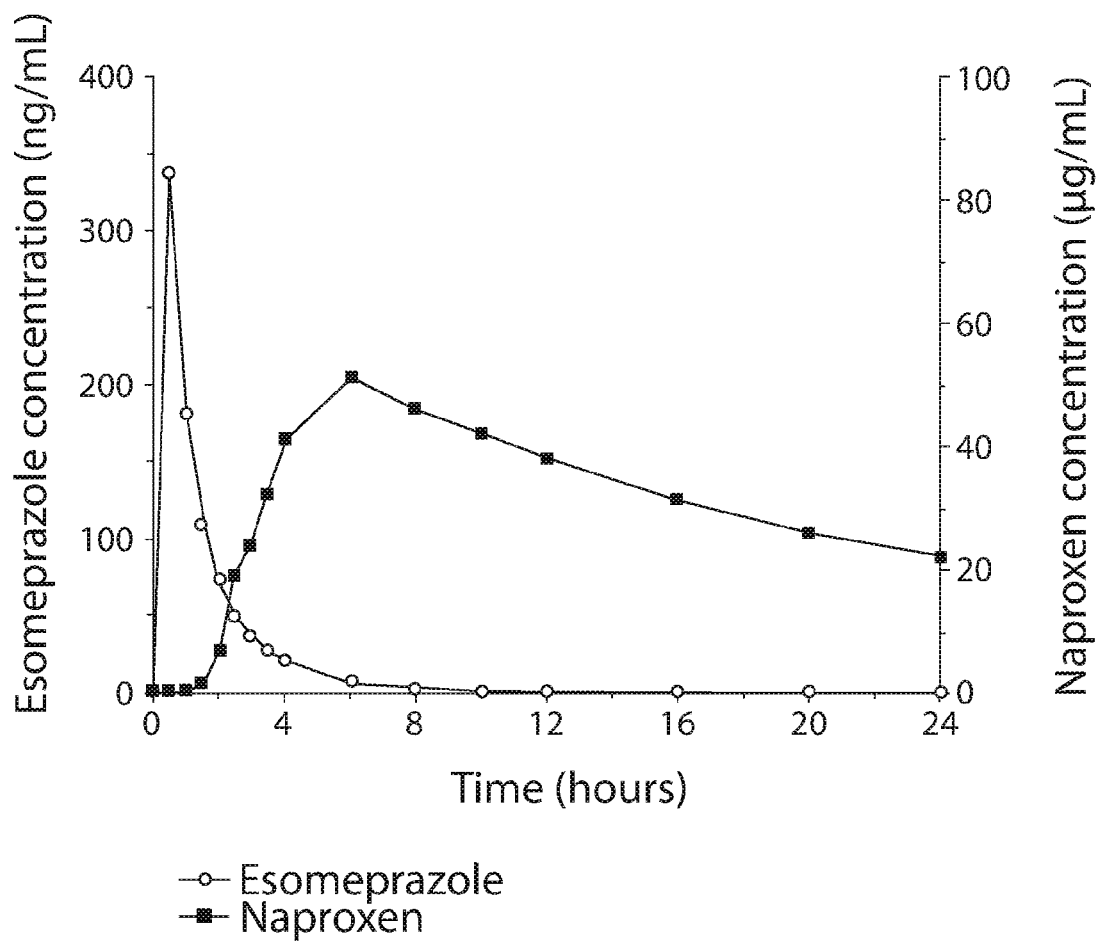
FIG. 11: Time course of esomeprazole and naproxen concentrations.

In contrast, EC E20+naproxen produced peak naproxen concentrations that preceded the increase in intragastric pH (FIG. 8B). In fact, peak naproxen concentrations occurred 1 to 2 hours post dose, which coincided with the time period when intragastric pH was lowest (FIG. 8B).

What is claimed is:

1. A method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater to target:
   a) a mean % time at which intragastric pH remains at about 4.0 or greater for about a 24 hour period of at least about 41%.

2. The method according to claim 1, wherein the mean % time at which intragastric pH remains at about 4.0 or greater for about a 24 hour period is at least about 60%.

3. The method according to claim 1, wherein the mean % time at which intragastric pH remains at about 4.0 or greater for about a 24 hour period is at least about 71%.

4. The method according to claim 1, wherein the mean % time at which intragastric pH remains at about 4.0 or greater for about a 24 hour period is at least about 77%.

5. The method according to claim 1, wherein said pharmaceutical composition in unit dose form comprises about 500 mg of said naproxen, or pharmaceutically acceptable salt thereof, and about 20 mg of said esomeprazole, or pharmaceutically acceptable salt thereof.

6. The method according to claim 1, wherein said patient in need thereof is an at risk patient.

7. The method according to claim 6, wherein said at risk patient is being treated for a disease or disorder selected from pain and inflammation.

8. The method according to claim 6, wherein said at risk patient is being treated for osteoarthritis, rheumatoid arthritis, ankylosing spondylitis, or a combination thereof.

9. A method for delivering a pharmaceutical composition to a patient in need thereof, comprising: administering to said patient a pharmaceutical composition in unit dose form comprising naproxen, or pharmaceutically acceptable salt thereof, and esomeprazole, or pharmaceutically acceptable salt thereof, wherein said esomeprazole, or pharmaceutically acceptable salt thereof, is released from said unit dose form at a pH of from about 0 or greater, wherein one unit dose form is administered as an AM dose and a second dose administered about 10 hours later as a PM dose to target:
   i) a pharmacokinetic (pk) profile for naproxen where:
      a) the AM dose has a mean $C_{max}$ of about 81 µg/mL and a median time to maximum concentration ($T_{max}$) of from about 2.5 to about 4 hours, and
      b) the PM dose has a mean $C_{max}$ of about 76.2 µg/mL and a median $T_{max}$ of from about 10 to about 14 hours; and
   ii) a pharmacokinetic (pk) profile for esomeprazole where:
      a) the AM dose has a mean area under the plasma concentration-time curve from time zero when the AM dose is administered to about 10 hours after the AM dose is administered ($AUC_{0-10,am}$) of about 850 hr*ng/mL, and
      b) the PM dose has a mean area under the plasma concentration-time curve from time zero when the PM dose is administered to about 14 hours after the PM dose is administered ($AUC_{0-14,pm}$) of about 650 hr*ng/mL.

10. The method according to claim 9, wherein the pharmaceutical composition further targets a mean % time at which intragastric pH remains at about 4.0 or greater for about a 24 hour period of at least about 41%.

11. The method according to claim 10, wherein the mean % time at which intragastric pH remains at about 4.0 or greater for about a 24 hour period is at least about 60%.

12. The method according to claim 10, wherein the mean % time at which intragastric pH remains at about 4.0 or greater for about a 24 hour period is at least about 71%.

13. The method according to claim 10, wherein the mean % time at which intragastric pH remains at about 4.0 or greater for about a 24 hour period is at least about 77%.

14. The method according to claim 9, wherein said pharmaceutical composition in unit dose form comprises about 500 mg of said naproxen and about 20 mg of said esomeprazole.

15. The method according to claim 9, wherein said patient in need thereof is an at risk patient.

16. The method according to claim 15, wherein said at risk patient is being treated for a disease or disorder selected from pain and inflammation.

17. The method according to claim 15, wherein said at risk patient is being treated for osteoarthritis, rheumatoid arthritis, ankylosing spondylitis, or a combination thereof.

18. The method according to claim 1, wherein said unit dose form is a multilayer tablet comprising at least one core and at least a first layer and a second layer, wherein:
   i) said core comprises naproxen, or pharmaceutically acceptable salt thereof;
   ii) said first layer is a coating that at least begins to release the naproxen, or pharmaceutically acceptable salt thereof, when the pH of the surrounding medium is about 3.5 or greater; and
   iii) said second layer is esomeprazole, wherein said esomeprazole is released at a pH of from about 0 or greater.

19. The method according to claim 18, wherein at least a portion of said esomeprazole, or pharmaceutically acceptable salt thereof, is not coated with an enteric coating.

20. The method according to claim 18, wherein said first layer is an enteric coating.

* * * * *

UNITED STATES PATENT AND TRADEMARK OFFICE
CERTIFICATE OF CORRECTION

PATENT NO.        : 9,801,824 B2
APPLICATION NO.   : 15/207623
DATED             : October 31, 2017
INVENTOR(S)       : Brian Ault et al.

Page 1 of 1

It is certified that error appears in the above-identified patent and that said Letters Patent is hereby corrected as shown below:

On the Title Page

Item (72) Inventors, Line 1, delete "Wilmington (DE)" and insert --Wilmington, DE (US)-- therefor.

In the Claims

In Claim 9, Column 48, Line 4, delete "C$_{max}$," and insert --C$_{max}$-- therefor.

Signed and Sealed this
Twentieth Day of February, 2018

Andrei Iancu
*Director of the United States Patent and Trademark Office*